US008404866B2

(12) United States Patent
Schwartz et al.

(10) Patent No.: US 8,404,866 B2
(45) Date of Patent: Mar. 26, 2013

(54) SUBSTITUTED HETEROCYCLIC MERCAPTOSULFONAMIDE METALLOPROTEASE INHIBITORS

(75) Inventors: Martin A. Schwartz, Tallahassee, FL (US); Yonghao Jin, Tallahassee, FL (US); Qing-Xiang (Amy) Sang, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 0 days.

(21) Appl. No.: 12/936,842

(22) PCT Filed: Sep. 2, 2009

(86) PCT No.: PCT/US2009/055742
§ 371 (c)(1),
(2), (4) Date: Feb. 26, 2011

(87) PCT Pub. No.: WO2010/028051
PCT Pub. Date: Mar. 11, 2010

(65) Prior Publication Data
US 2011/0144179 A1 Jun. 16, 2011

Related U.S. Application Data

(60) Provisional application No. 61/093,742, filed on Sep. 3, 2008.

(51) Int. Cl.
*C07D 207/16* (2006.01)
*A61K 31/40* (2006.01)
(52) U.S. Cl. ....................... 548/540; 514/423
(58) Field of Classification Search ............... 548/540; 514/423
See application file for complete search history.

(56) References Cited

U.S. PATENT DOCUMENTS

| | | | |
|---|---|---|---|
| 5,455,262 | A | 10/1995 | Schwartz et al. |
| 6,624,196 | B2 | 9/2003 | Purchase, Jr. et al. |
| 6,747,027 | B1 | 6/2004 | DeCrescenzo et al. |
| 6,790,860 | B2 * | 9/2004 | Aebi et al. ............ 514/423 |
| 2006/0211730 | A1 | 9/2006 | Levin et al. |

FOREIGN PATENT DOCUMENTS

| | | | |
|---|---|---|---|
| GB | 589040 | * | 6/1945 |
| WO | 2005/032541 A1 | | 4/2005 |
| WO | 2007/050522 A1 | | 5/2007 |
| WO | 2008/075070 A1 | | 6/2008 |

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chapters 9-10 provided.*
Zhang et al. (Bioorg. Med. Chem. Lett. 18 (2008) 409-413).*
Boyle et al. (CAPLUS Abstract of WO 9706138).*
International Search Report for PCT/US2009/055742, dated May 14, 2010, 4 pages.
Brinckerhoff et al, Matrix metalloproteinases: a tail of a frog that became a prince, Nature Reviews Molecular Cell Biology, 2002, 3, 207-214.
Chun et al., A Pericellular Collagenase Directs the 3-Dimensional Development of White Adipose Tissue, Cell, May 6, 2006, 125, 577-591.
Coussens et al., Matrix Metalloproteinase Inhibitors and Cancer: Trials and Tribulations, Science; Mar. 29, 2002, 295(5564), 2387-2292.
Cudic et al., Extracellular Proteases as Targets for Drug Development, Current Protein and Peptide Science, 2009, 10, 297-307.
Demedts et al., Matrix metalloproteinases in asthma and COPD, Current Opinion in Pharmacology, 2005, 5, 257-263.
Egeblad et al., New Functions for the Matrix Metalloproteinases in Cancer Progression, Nature Reviews Cancer, Mar. 2002, 2, 29 pages.
Golubkov et al., Membrane Type-1 Matrix Metalloproteinase Confers Aneuploidy and Tumorigenicity on Mammary Epithelial Cells, Cancer Research, 2006, 66, 10460-10465.
Holmbeck et al., MT1-MMP-Deficient Mice Develop Dwarfism, Osteopenia, Arthritis, and Connective Tissue Disease due to Inadequate Collagen Turnover, Cell, 1999, 99, 81-92.
Hotary et al., Membrane Type I Matrix Metalloproteinase Usurps Tumor Growth Control Imposed by the Three-Dimensional Extracellular Matrix, Cell, 2003, 114, 33-45.
Hu et al., Matrix metalloproteinase inhibitors as therapy for inflammatory and vascular diseases, Nature Reviews Drug Discovery, 2007, 6, 480-498.
Hurst et al., Inhibition of enzyme activity of and cell-mediated substrate cleavage by membrane type 1 matrix metalloproteinase by newly developed mercaptosulphide inhibitors, Biochem. J., 2005 392, 527-536.
Kawasaki et al., Distinct roles of matrix metalloproteases in the early- and late-phase development of neuropathic pain, Nature Medicine, 2008, 14, 331-336.
Mercer et al., Extracellular Regulated Kinase/Mitogen Activated Protein Kinase Is Up-regulated in Pulmonary Emphysema and Mediates Matrix Metalloproteinase-1 Induction by Cigarette Smoke, The Journal of Biological Chemistry, 2004, 279(17), 17690-17696.
Morrison et al., Matrix metalloproteinase proteomics: substrates, targets, and therapy, 2009, Current Opinion in Cell Biology, 21, 645-653.
Muroski et al., Matrix Metalloproteinase-9/Gelatinase B is a Putative Therapeutic Target of Chronic Obstructive Pulmonary Disease and Multiple Sclerosis, Current Pharmaceutical Biotechnology, 2008, 9, 34-46.

(Continued)

*Primary Examiner* — Robert Havlin
(74) *Attorney, Agent, or Firm* — Bryan Cave LLP

(57) ABSTRACT

The present invention generally relates to substituted heterocyclic mercaptosulfonamide compounds, precursors, and derivatives as well as methods for the preparation of and pharmaceutical compositions comprising these compounds. These compounds are designed to be potent selective inhibitors of matrix metalloproteinases (MMPs), including, for example, gelatinases, collagenases, matrilysins, metalloelastase, stromelysin, and membrane-type 1 matrix metalloproteinase. These inhibitors may be used for the control of physiological and pathological processes and disease conditions in which MMPs are believed to play significant functions.

29 Claims, 7 Drawing Sheets

OTHER PUBLICATIONS

Pfefferkorn et al., Closure of the Blood-Brain Barrier by Matrix Metalloproteinase Inhibition Reduces rtPA—Mediated Mortality in Cerebral Ischemia With Delayed Reperfusion, Stroke, 2003, 34, 2025-2030.

Roycik et al., A Fresh Prospect of Extracellular Matrix Hydrolytic Enzymes and Their Substrates, Current Pharmaceutical Design, 2009, 15, 1295-1308.

Overall et al., Strategies for MMP inhibition in cancer: innovations for the post-trial era, Nature Reviews: Cancer, 2002, 2, 657-672.

Overall, C. M., Molecular Determinants of Metalloproteinase Substrate Specificity, Molecular Biotechnology, 2002, 22, 51-86.

Radichev et al., Biochemical evidence of the interactions of membrane type-1 matrix metalloproteinase (MT1-MMP) with adenine nucleotide translocator (ANT): potential implications linking proteolysis with energy metabolism in cancer cells, Biochemical Journal, 2009, 420, 37-47.

Sang et al., Matrix Metalloproteinase Inhibitors as Prospective Agents for the Prevention and Treatment of Cardiovascular and Neoplastic Diseases, Current Topics in Medicinal Chemistry, 2006, 6, 289-316.

Sternlicht et al., How matrix metalloproteinases regulate cell behavior, Annual Review Cell Development Biology 2001, 17, 463-516.

* cited by examiner

SUBSTITUTED HETEROCYCLIC MERCAPTOSULFONAMIDE METALLOPROTEASE INHIBITORS

This application claims priority from U.S. patent application Ser. No. 61/093,742, filed Sep. 3, 2008, the entire contents of which are incorporated herein by reference.

FIELD OF THE INVENTION

The present invention generally relates to substituted heterocyclic mercaptosulfonamide compounds, precursors, and derivatives as well as methods for the preparation of and pharmaceutical compositions comprising these compounds. These compounds are designed to be potent selective inhibitors of matrix metalloproteinases (MMPs), including, for example, gelatinase A and B (MMP-2 & -9), collagenases (MMP-1, -8, & -13), matrilysins (MMP-7 & -26), metalloelastase (MMP-12), stromelysin-1 (MMP-3), and membrane-type 1 matrix metalloproteinase (MT1-MMP or MMP-14). These inhibitors may be used for the control of physiological and pathological processes and disease conditions in which MMPs are believed to play significant functions.

BACKGROUND OF THE INVENTION

Mercaptosulfide inhibitors and other MMP inhibitors have been identified as potential modulators of the physiological and pathological processes and disease conditions in which matrix metalloproteinases (MMPs) are believed to play significant functions (Sternlicht, M. D., Werb Z. How matrix metalloproteinases regulate cell behavior. *Annu Rev Cell Dev Biol.* 2001; 17, 463-516; Mercer B. A., Kolesnikova N., Sonett J., D'Armiento J. Extracellular regulated kinase/mitogen activated protein kinase is up-regulated in pulmonary emphysema and mediates matrix metalloproteinase-1 induction by cigarette smoke. *J. Biol. Chem.* 2004. 279:17690-17696; Pfefferkorn, T., Rosenberg, G. A. Closure of the blood-brain barrier by matrix metalloproteinase inhibition reduces rtPA-mediated mortality in cerebral ischemia with delayed reperfusion. *Stroke.* 2003; 34, 2025-2530; M. A. Schwartz and H. E. Van Wart, 1995, U.S. Pat. No. 5,455,262, Mercaptosulfide metalloproteinase inhibitors; C. F. Purchase, Jr., B. D. Roth, and A. D. White, 2003, U.S. Pat. No. 6,624, 196 B2, Benzene butyric acids and their derivatives as inhibitors of matrix metalloproteinases; Schwartz, M. A., Jin, Y., Hurst, D. R., Sang, Q.-X. Patent Cooperation Treaty (PCT) International Application Pub. No. WO 2005/032541 A1, Substituted Heterocyclic mercaptosulfide Inhibitors; De Crescenzo G., Abbas Z. S., Freskos, J. N., Getman, D. P., Heintz, R. M., Mischke, B. V., McDonald, J. J. 2004, U.S. Pat. No. 6,747,027 B1, Thiol sulfonamide metalloprotease Inhibitors; Levin, J. I., Li, Z., Diamantidis, G., Lovering, F. E., Wang, W., Condon J. S., Lin, Y. I., Skotnicki, J. S., and Park, K., U.S. Patent Application Pub. No. US 2006/0211730 A1, Beta-sulfonamide hydroxamic acid inhibitors of TACE/matrix metalloproteinase; D. R. Hurst, M. A. Schwartz, Y. Jin, M. A. Ghaffari, P. Kozarekar, J. Cao, and Q.-X. Sang. Inhibition of enzyme activity and cell-mediated substrate cleavage of membrane type 1-matrix metalloproteinase by newly developed mercaptosulphide inhibitors. *Biochem. J.* 2005; 392, 527-536; Sang, Q. X., Jin, Y., Newcomer, R. G., Monroe, S. C., Fang, X., Hurst, D. R., Lee, S., Cao, Q., Schwartz, M. A. Matrix Metalloproteinase Inhibitors as Prospective Agents for the Prevention and Treatment of Cardiovascular and Neoplastic Diseases. *Curr. Top. Med. Chem.* 2006; 6, 289-316; Hu, J., Van den Steen, P. E., Sang, Q. X., Opdenakker, G. Matrix metalloproteinase inhibitors as therapy for inflammatory and vascular diseases. *Nat. Rev. Drug Discov.* 2007; 6, 480-498; M. E. Muroski, M. D. Roycik, R. G. Newcomer, P. E. Van den Steen, G. Opdenakker, H. R. Monroe, Z. J. Sahab, and Q.-X. Sang. Matrix Metalloproteinase-9/Gelatinase B is a Putative Therapeutic Target of Chronic Obstructive Pulmonary Disease and Multiple Sclerosis. *Current Pharmaceutical Biotechnology,* 2008; 9, 34-46; Kawasaki, Y., Xu, Z. Z., Wang, X., Park, J. Y., Zhuang, Z. Y., Tan, P. H., Gao, Y. J., Roy, K., Corfas, G., Lo, E. H., Ji, R. R. Distinct roles of matrix metalloproteases in the early- and late-phase development of neuropathic pain. *Nat. Med.* 2008; 14, 331-336). For example, such physiological and pathological processes and disease conditions include the prevention and treatment of (1) cancer invasion, angiogenesis, and metastasis; (2) stroke and chronic cerebral vascular dementia; (3) cardiovascular diseases such as myocardial infarction, atherosclerosis, and restenosis; (4) neuroinflammatory diseases; (5) neurodegenerative diseases such as Alzheimer's; (6) autoimmune diseases; (7) multiple sclerosis; (8) spinal cord injury; (9) arthritic diseases; (10) psoriasis; (11) periodontal disease, as inhibitors may be added to toothpastes and mouthwashes; (12) inflammation disorders; (13) Crohn's disease and irritable bowel syndrome; (14) pain and pain-related pathologies; (15) cartilage and bone diseases; (16) skin/muscular skeletal injuries and disorders; (17) corneal ulceration and other eye diseases (where MMP inhibitors may be used in eye drops or as drugs put into/onto contact lenses); (18) diabetic retinopathy and other complications; (19) adipogenesis and obesity; (20) tissue ulceration; (21) wound healing and regeneration disorders; (22) kidney diseases such as glomerulonephritis; (23) respiratory and lung diseases and disorders such as allergies, asthma, chronic obstructive pulmonary disorders, and emphysema; (24) infection of human immunodeficiency virus (HIV) and acquired immunodeficiency syndrome (AIDS); (25) septic shock syndromes; (26) cachexia and anorexia; (27) organ preservation for transplantation; (28) control of fertility and reproductive capabilities, such as fertilization, implantation, uterine bleeding, birth control, and contraception; (28) blister formation; (29) bone remodeling; (30) osteoporosis; (31) meningitis; (32) malaria; (33) mycobaterial infection; (34) aging and rheumatic disorders; (35) connective tissue degradation and degeneration; (36) bacterial activities and infections, including lethal factor and other bacterial toxins; (37) viral and other microbial proteases and infections; (38) snake venom and other toxins; (39) industrial manufacturing of extracellular matrix/collagen products; and (40) cosmetics and beauty products, which would include combining MMP inhibitors with collagen and gelatin gel injections to facilitate a youthful and beautiful appearance. These compounds, which can be used for human beings, animals, and other organisms, will also be conjugated to a variety of materials (e.g. fluorescent dyes, radioactive materials, quantum dots, etc.) for uses in applications ranging from drug-targeting to cell, tissue, and whole-body imaging.

Matrix metalloproteinases (MMPs, matrixins) are a family of zinc-endopeptidase enzymes that are believed to participate in numerous processes, some of which include angiogenesis, embryonic development, morphogenesis, tissue resorption and remodeling, reproduction, arthritis, and the growth, progression, invasion, and metastasis of cancerous tumors (Brinckerhoff, C. E., Matrisian, L. M. Matrix metalloproteinases: a tail of a frog that became a prince. *Nature Rev. Mol. Cell. Biol.* 2002; 3, 207-214; Egeblad, M., Werb, Z. New functions for the matrix metalloproteinases in cancer progression. *Nature Rev. Cancer* 2002; 2, 163-175; Overall, C. M., López-Otín, C. Strategies for MMP inhibition in cancer: innovations for the post-trial era. *Nat. Rev. Cancer.* 2002; 2, 657-672; Coussens, L. M., Fingleton, B., Matrisian, L. M. Matrix metalloproteinase inhibitors and cancer: trials and tribulations. *Science.* 2002; 295, 2387-2392). The contribution of matrix metalloproteinases to these processes is achieved through their digestion of the extracellular matrix (ECM), proteolytic cleavage of cell surface proteins, and the processing of various growth factors, cytokines, and chemokines (Overall, C. M. Molecular determinants of metalloproteinase substrate specificity: matrix metalloproteinase substrate binding domains, modules, and exosites. *Molec. Biotech.* 2002; 22, 51-86). At least twenty-five MMPs have been reported in humans and other vertebrates. Many MMPs have been reported to play multiple functions in ECM remodeling, development, growth, morphogenesis, and various pathologies. For example, mice deficient for membrane-type 1 matrix metalloproteinase (MT1-MMP) developed dwarfism, osteopenia, arthritis, craniofacial dysmorphism, and soft-tissue fibrosis due to the ablation of a collagenolytic activity that is essential for the modeling of skeletal and extraskeletal connective tissues (Holmbeck, K., Bianco, P., Caterina, J., Yamada, S., Kromer, M., Kuznetsov, S. A., Mankani, M., Robey, P. G., Poole, A. R., Pidoux, I., Ward, J. M., Birkedal-Hansen, H. MT1-MMP-deficient mice develop dwarfism, osteopenia, arthritis, and connective tissue disease due to inadequate collagen turnover. *Cell,* 1999; 99, 81-92). In contrast to a constructive role for MT1-MMP in embryo development, this MMP is essential for promoting 3-dimensional tumor growth and invasion in vitro and in vivo with aberrant expression suggesting a deleterious role (Hotary, K. B., Allen, E. D., Brooks, P. C., Datta, N. S., Long, M. W., Weiss, S. J. Membrane type I matrix metalloproteinase usurps tumor growth control imposed by the three-dimensional extracellular matrix. *Cell,* 2003; 114, 33-45). MT1-MMP may be involved in oncogenesis and energy metabolism in cancer cells (Golubkov, V. S., Chekanov, A. V., Savinov, A. Y., Rozanov, D. V., Golubkova, N. V., Strongin, A. Y. Membrane type-1 matrix metalloproteinase confers aneuploidy and tumorigenicity on mammary epithelial cells. *Cancer Res.* 2006; 66, 10460-10465; Radichev, I. A., Remacle, A. G., Sounni, N. E., Shiryaev, S. A., Rozanov, D. V., Zhu, W., Golubkova, N. V., Postnova, T. I., Golubkov, V. S., Strongin, A. Y. Biochemical evidence of the interactions of membrane type-1 matrix metalloproteinase (MT1-MMP) with adenine nucleotide translocator (ANT): potential implications linking proteolysis with energy metabolism in cancer cells. *Biochem J.* 2009; 420, 37-47). MT1-MMP also controls the white adipose tissue formation in vivo and may be a target for obesity treatment (Chun, T. H., Notary, K. B., Sabeh, F., Saltiel, A. R., Allen, E. D., and Weiss, S. J. A pericellular collagenase directs the 3-dimensional development of white adipose tissue. *Cell.* 2006; 125, 577-591). Increasing evidence has indicated that MMPs, especially MMP-9, are involved in the pathogenesis of asthma, chronic obstructive pulmonary disease, and multiple sclerosis (Demedts, I. K., Brusselle, G. G., Bracke, K. R., Vermaelen, K. Y., Pauwels, R. A. Matrix metalloproteinases in asthma and COPD. *Curr. Opin. Pharmacol.* 2005; 5, 257-263; M. E. Muroski, M. D. Roycik, R. G. Newcomer, P. E. Van den Steen, G. Opdenakker, H. R. Monroe, Z. J. Sahab, and Q.-X. Sang. Matrix Metalloproteinase-9/Gelatinase B is a Putative Therapeutic Target of Chronic Obstructive Pulmonary Disease and Multiple Sclerosis. *Curr. Pharma. Biotechnol.,* 2008; 9, 34-46). It is reported that many new extracellular protease inhibitors are under clinical investigation and new therapies based on protease inhibition will be in fruition in the future (Cudic, M., Fields, G. B. Extracellular proteases as targets for drug development. *Curr. Protein Pept. Sci.* 2009; 10, 297-307; M. D. Roycik, X. Fang, and Q.-X. Sang. A fresh prospect of extracellular matrix hydrolytic enzymes and their substrates. *Curr. Pharmaceutical Design.* 2009; 15, 1295-1308; Morrison C J, Butler G S, Rodriguez D, Overall C M. Matrix metalloproteinase proteomics: substrates, targets, and therapy. *Curr. Opin. Cell Biol.* 2009 Jul. 16. [Epub ahead of print]). Thus, selective inhibition of certain MMP family members, specifically those modulating certain pathophysiologies and disease conditions, are highly desirable.

SUMMARY OF THE INVENTION

Among the various aspects of the present invention is the provision of substituted heterocyclic mercaptosulfonamide inhibitors and the salts thereof.

Briefly, therefore, the present invention is directed to substituted heterocyclic mercaptosulfonamides corresponding to Formula 1:

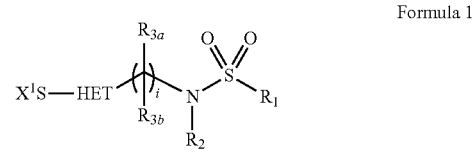

Formula 1 wherein

HET is a five- or six-membered heterocycle containing, as heteroatoms, one ring nitrogen atom, two ring nitrogen atoms, or a ring nitrogen atom and a ring oxygen atom, and 4 or 5 carbon atoms;

i is 0 or 1;

$R_1$ is hydrocarbyl, substituted hydrocarbyl, or heterocyclo;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl; and $X^1$ is a cation, hydrogen, or acyl.

The present invention is further directed to substituted heterocyclic mercaptosulfonamides corresponding to Formula 2:

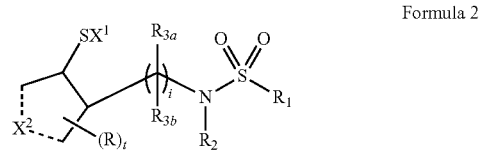

Formula 2 wherein $A^-$ is a counteranion;

i is 0 or 1;

each R is independently hydrocarbyl, substituted hydrocarbyl, heterocyclo, or carbonyl (=O);

$R_1$ is hydrocarbyl, substituted hydrocarbyl, or heterocyclo;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$R_{22}$ and $R_{23}$ are independently hydrogen, hydrocarbyl, substituted hydrocarbyl, or heterocyclo, or, $R_{22}$ and $R_{23}$, in combination, are carbonyl (=O);

t is an integer from 0 to 4, inclusive;

$X^1$ is a cation, hydrogen or acyl;

$X^2$ is $-N(X^{20})-$, $-N(X^{20})O-$, $-N(X^{20})C(R_{22})(R_{23})-$, $-N(X^{20})N(X^{25})-$ or $-N^+(X^{26})(X^{27})-A^-$;

$X^{20}$ is hydrogen, hydrocarbyl, substituted hydrocarbyl, heterocyclo, acyl, sulfonyl, phosphonyl, $-OX^{21}$, $-NX^{23}X^{24}$, thionyl, or $-C(S)X^{28}$;

$X^{21}$ is hydrogen, hydrocarbyl, substituted hydrocarbyl or heterocyclo;

$X^{23}$ and $X^{24}$ are independently hydrogen, hydrocarbyl or heterocyclo, or, in combination with the nitrogen atom to which they are attached, form a heterocyclo ring;

$X^{26}$ and $X^{27}$ are independently hydrogen, hydrocarbyl, substituted hydrocarbyl, or in combination with the nitrogen atom to which they are attached, form a heterocyclo ring; and $X^{28}$ is hydrogen, hydrocarbyl, substituted hydrocarbyl, or heterocyclo.

The present invention is further directed to substituted heterocyclic mercaptosulfonamides corresponding to Formula 3:

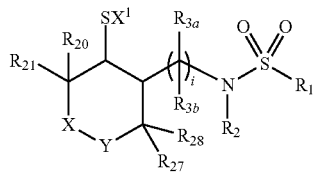

Formula 3 wherein

designates the point of attachment of the segment, —X—Y—, to the remainder of the heterocyclic ring;

i is 0 or 1;

$R_1$ is hydrocarbyl, substituted hydrocarbyl, or heterocyclo;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$R_{20}$, $R_{21}$, $R_{22}$, $R_{23}$, $R_{27}$ and $R_{28}$ are independently hydrogen, hydrocarbyl, substituted hydrocarbyl, or heterocyclo, or, $R_{20}$ and $R_{21}$, in combination, are carbonyl (=O), or, $R_{22}$ and $R_{23}$, in combination, are carbonyl (=O), or, $R_{27}$ and $R_{28}$, in combination, are carbonyl (=O);

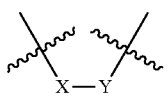

is $-N(X^{20})O-$, $-ON(X^{20})-$, $-N(X^{20})C(R_{22})(R_{23})-$, $-C(R_{22})(R_{23})N(X^{20})-$, or $-N(X^{20})N(X^{25})-$;

$X^1$ is a cation, hydrogen or acyl;

$X^{20}$ is hydrogen, hydrocarbyl, substituted hydrocarbyl, heterocyclo, acyl, sulfonyl, phosphonyl, $-OX^{21}$, $-NX^{23}X^{24}$, thionyl, or $-C(S)X^{28}$;

$X^{21}$ is hydrogen, hydrocarbyl, substituted hydrocarbyl or heterocyclo;

$X^{23}$ and $X^{24}$ are independently hydrogen, hydrocarbyl or heterocyclo, or, in combination with the nitrogen atom to which they are attached, form a heterocyclo ring;

$X^{25}$ is hydrogen, hydrocarbyl, substituted hydrocarbyl, heterocyclo, acyl, sulfonyl, phosphonyl, $-OX^{21}$, $-NX^{23}X^{24}$, thionyl, or $-C(S)X^{28}$; and $X^{28}$ is hydrogen, hydrocarbyl, substituted hydrocarbyl, or heterocyclo.

The present invention is further directed to substituted heterocyclic mercaptosulfonamides corresponding to Formula 4:

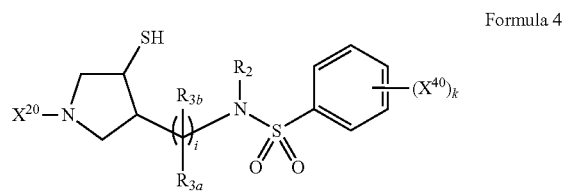

Formula 4 wherein i is 0 or 1;

k is an integer from 1 to 5, inclusive;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$X^{20}$ is hydrogen, hydrocarbyl, substituted hydrocarbyl, heterocyclo, acyl, sulfonyl, phosphonyl, $-OX^{21}$, $-NX^{23}X^{24}$, thionyl, or $-C(S)X^{28}$;

$X^{21}$ is hydrogen, hydrocarbyl, substituted hydrocarbyl or heterocyclo;

$X^{23}$ and $X^{24}$ are independently hydrogen, hydrocarbyl or heterocyclo, or, in combination with the nitrogen atom to which they are attached, form a heterocyclo ring;

$X^{28}$ is hydrogen, hydrocarbyl, substituted hydrocarbyl, or heterocyclo; and each $X^{40}$ is independently hydrocarbyl, substituted hydrocarbyl, halo, amino, nitro, hydroxy, alkoxy, acyl, or heterocyclo.

The present invention is further directed to substituted heterocyclic mercaptosulfonamides corresponding to Formula 5:

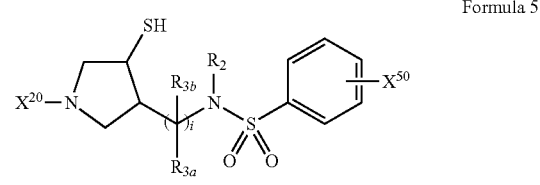

Formula 5 wherein i is 0 or 1;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$X^{20}$ is hydrogen, hydrocarbyl, substituted hydrocarbyl, heterocyclo, acyl, sulfonyl, phosphonyl, $-OX^{21}$, $-NX^{23}X^{24}$, thionyl, or $-C(S)X^{28}$;

$X^{21}$ is hydrogen, hydrocarbyl, substituted hydrocarbyl or heterocyclo;

$X^{23}$ and $X^{24}$ are independently hydrogen, hydrocarbyl or heterocyclo, or, in combination with the nitrogen atom to which they are attached, form a heterocyclo ring;

$X^{28}$ is hydrogen, hydrocarbyl, substituted hydrocarbyl, or heterocyclo; and $X^{50}$ is hydrocarbyl, substituted hydrocarbyl, halo, amino, nitro, hydroxy, alkoxy, acyl, or heterocyclo.

The present invention is further directed to substituted heterocyclic mercaptosulfonamides corresponding to Formula 6:

Formula 6

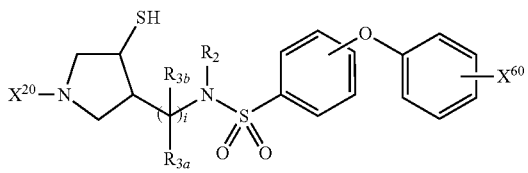

wherein i is 0 or 1;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$X^{20}$ is hydrogen, hydrocarbyl, substituted hydrocarbyl, heterocyclo, acyl, sulfonyl, phosphonyl, —$OX^{21}$, —$NX^{23}X^{24}$, thionyl, or —$C(S)X^{28}$;

$X^{21}$ is hydrogen, hydrocarbyl, substituted hydrocarbyl or heterocyclo;

$X^{23}$ and $X^{24}$ are independently hydrogen, hydrocarbyl or heterocyclo, or, in combination with the nitrogen atom to which they are attached, form a heterocyclo ring;

$X^{28}$ is hydrogen, hydrocarbyl, substituted hydrocarbyl, or heterocyclo;

$X^{60}$ is hydrocarbyl, substituted hydrocarbyl, halo, amino, nitro, hydroxy, alkoxy, acyl, or —$C(O)X^{61}$; and $X^{61}$ is hydroxy, amino or alkoxy.

Other objects and features will be in part apparent and in part pointed out hereinafter.

Abbreviations and Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrogen, hydrocarbyl, heterosubstituted hydrocarbyl, or heterocyclo, and $R^2$ is hydrogen, hydrocarbyl or substituted hydrocarbyl.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxy" as used herein alone or as part of another group denotes the moiety —$OR^1$— wherein $R^1$ is an alkyl.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "amino" as used herein alone or as part of another group denotes the moiety —$NR^1R^2$ wherein $R^1$ and $R^2$ are hydrocarbyl, substituted hydrocarbyl or heterocyclo.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "DCM" as used herein denotes the moiety dichloromethane.

The term "DEAD" as used herein denotes the moiety diethylazodicarboxylate.

The term "DMF" as used herein denotes the moiety dimethylformamide.

The terms "halogen" or "halo" as used herein alone or as part of another group denote chlorine, bromine, fluorine, and iodine.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, acyl, acyloxy, alkoxy, alkenoxy, alkynoxy, aryloxy, halogen, amido, amino, nitro, cyano, thiol, ketals, acetals, esters and ethers.

Unless otherwise indicated, the terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics and saturated heterocyclics such as pyrrolinyl, tetrahydrofuranyl, tetrahydrothiophenyl piperidinyl, tetrahydropyranyl, thianyl, piperazinyl, oxazinyl, dithianyl, and dioxanyl and the like. Exemplary substituents include one or more of the following groups: hydrocarbyl, substituted hydrocarbyl, keto, hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein denote organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "pharmaceutically acceptable" as used herein denotes that the modified noun is appropriate for use in a pharmaceutical product; that is, the "pharmaceutically acceptable" material is relatively safe and/or non-toxic, though not necessarily providing a separable therapeutic benefit by itself. Pharmaceutically acceptable cations include metallic ions and organic ions. More preferred metallic ions include, but are not limited to appropriate alkali metal salts, alkaline earth metal salts and other physiologically acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

The term "phosphonyl" as used herein alone or as part of another group denotes the moiety corresponding to the formula $Z^2P(O)(OH)$— wherein $Z^2$ is hydrocarbyl, substituted hydrocarbyl, heterocyclo, $R^1R^2N$—, or $R^1O$—, where $R^1$ is hydrogen, hydrocarbyl, substituted hydrocarbyl, or heterocyclo, and $R^2$ is hydrogen, hydrocarbyl, substituted hydrocarbyl or heterocyclo.

The term "substituted hydrocarbyl," "substituted alkyl," "substituted alkenyl," "substituted alkynyl," "substituted aryl," "substituted heterocyclo," or "substituted heteroaryl" as used herein denotes hydrocarbyl, alkyl, alkenyl, aryl, heterocyclo, or heteroaryl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, amino, amido, nitro, cyano, thiol, ketals, acetals, esters and ethers.

The term "sulfonyl" as used herein alone or as part of another group denotes the moiety corresponding to the formula $Z^1SO_2$— wherein $Z^1$ is hydrocarbyl, substituted hydrocarbyl, heterocyclo, $R^1R^2N$—, or $R^1O$—, where $R^1$ is hydrogen, hydrocarbyl, substituted hydrocarbyl, or heterocyclo, and $R^2$ is hydrogen, hydrocarbyl, substituted hydrocarbyl or heterocyclo.

The term "TCEP" as used herein denotes the moiety tris (2-carboxyethyl)phosphine.

The term "TEA" as used herein denotes the moiety triethylamine.

The term "THF" as used herein denotes the moiety tetrahydrofuran.

The term "thiol" as used herein alone or as part of another group denotes the moiety —SH.

The term "thionyl" as used herein alone or as part of another group denotes the moiety $Z^3SO$—, wherein $Z^3$ is hydrogen, hydrocarbyl, substituted hydrocarbyl or heterocyclo.

DETAILED DESCRIPTION OF THE PREFERRED EMBODIMENTS

Figure 1:
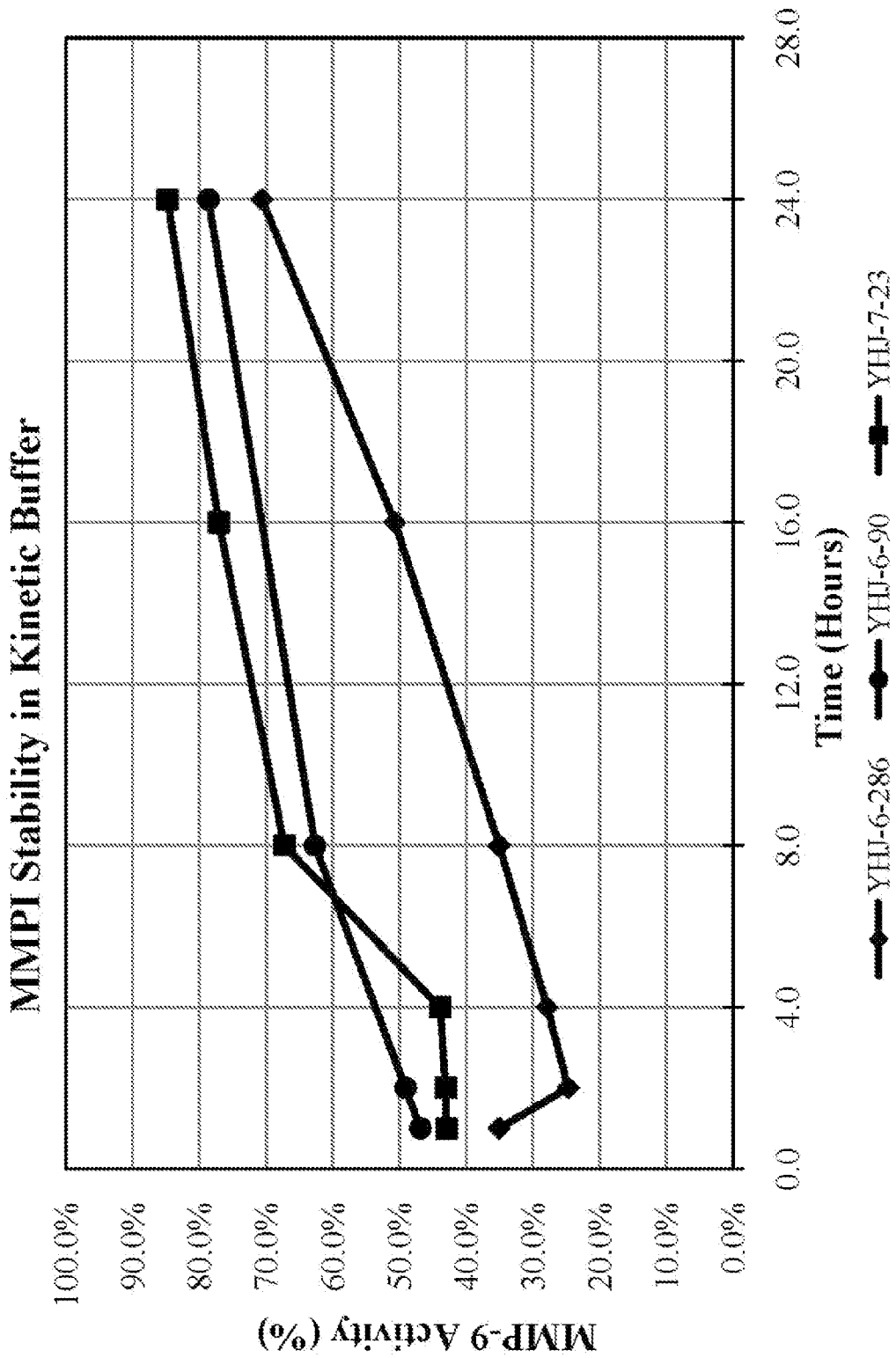
FIG. 1 is a graph showing the stability of three heterocyclic mercaptosulfonamide MMPIs incubated with human MMP-9 in HEPES buffer at various times points, as further described in Example 16.

The present invention is generally directed to substituted heterocyclic mercaptosulfonamide compounds, their precursors, and their derivatives, the methods for preparation, and pharmaceutical compositions as described in this invention. These small, synthetic compounds are potent and relatively selective inhibitors of matrix metalloproteinases (MMPs), e.g. gelatinases, collagenases, matrilysins, metalloelastase, stromelysin-1, and membrane-type 1 MMP. Specifically, these inhibitors can be used for the control of aberrant metalloprotease activity in a multitude of physiological and pathological processes. For example, they may be used for the prevention of and/or treatments for: (1) cancer invasion, angiogenesis, and metastasis; (2) stroke and chronic cerebral vascular dementia; (3) cardiovascular diseases such as myocardial infarction, atherosclerosis, and restenosis; (4) neuroinflammatory diseases; (5) neurodegenerative diseases such as Alzheimer's; (6) autoimmune diseases; (7) multiple sclerosis; (8) spinal cord injury; (9) arthritic diseases; (10) psoriasis; (11) periodontal disease, as inhibitors may be added to toothpastes and mouthwashes; (12) inflammation disorders; (13) Crohn's disease and irritable bowel syndrome; (14) pain and pain-related pathologies; (15) cartilage and bone diseases; (16) skin/muscular skeletal injuries and disorders; (17) corneal ulceration and other eye diseases (where MMP inhibitors may be used in eye drops or as drugs put into/onto contact lenses); (18) diabetic retinopathy and other complications; (19) adipogenesis and obesity; (20) tissue ulceration; (21) wound healing and regeneration disorders; (22) kidney diseases such as glomerulonephritis; (23) respiratory and lung diseases and disorders such as allergies, asthma, chronic obstructive pulmonary disorders, and emphysema; (24) infection of human immunodeficiency virus (HIV) and acquired immunodeficiency syndrome (AIDS); (25) septic shock syndromes; (26) cachexia and anorexia; (27) organ preservation for transplantation; (28) control of fertility and reproductive capabilities, such as fertilization, implantation, uterine bleeding, birth control, and contraception; (28) blister formation; (29) bone remodeling; (30) osteoporosis; (31) meningitis; (32) malaria; (33) mycobaterial infection; (34) aging and rheumatic disorders; (35) connective tissue degradation and degeneration; (36) bacterial activities and infections, including lethal factor and other bacterial toxins; (37) viral and microbial protease infections; (38) snake venom and other toxins; (39) industrial manufacturing of extracellular matrix/collagen products; and (40) cosmetics and beauty products, which would include combining MMP inhibitors with collagen and gelatin gel injections to facilitate a youthful and beautiful appearance. These compounds, which can be used for human beings, animals, and other organisms, will also be conjugated to a variety of materials (e.g. fluorescent dyes, radioactive materials, quantum dots, etc.) for uses in applications ranging from drug-targeting to cell, tissue, and whole-body imaging.

The substituted heterocyclic mercaptosulfonamides of the present invention generally correspond to Formula 1:

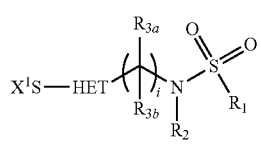

Formula 1 wherein HET is a five- or six-membered heterocycle containing, as heteroatoms, one ring nitrogen atom, two ring nitrogen atoms, or a ring nitrogen atom and a ring oxygen atom, and 4 or 5 carbon atoms; i is 0 or 1; $R_1$ is hydrocarbyl, substituted hydrocarbyl, or heterocyclo; $R_2$ is hydrogen, hydrocarbyl, substituted hydrocarbyl, or heterocyclo; $R_{3a}$ and $R_{3b}$, when i is 1, are independently hydrogen, hydrocarbyl, or substituted hydrocarbyl; and $X^1$ is a cation, hydrogen or acyl.

As noted, $X^1$ may be a cation, hydrogen, or acyl. In one preferred embodiment, $X^1$ is hydrogen. In another preferred embodiment, $X^1$ may be an alkali metal; for example, $X^1$ may be sodium or potassium. In a further embodiment, $X^1$ may be an alkaline earth metal; for example, $X^1$ may be magnesium or calcium. In other embodiments, $X^1$ may be aluminum or ammonium. In a further embodiment $X^1$ may be acyl; for example, $X^1$ may be RC(O)—, wherein R is $R^1$, $R^1O$—, $R^1R^2N$—, or $R^1S$—, wherein $R^1$ is hydrocarbyl, heterosubstituted hydrocarbyl, or heterocyclo and $R^2$ is hydrogen, hydrocarbyl or substituted hydrocarbyl. In an embodiment, $X^1$ is acetyl. In another embodiment $X^1$ is $SX^{11}$, wherein $X^{11}$ is hydrocarbyl, substituted hydrocarbyl, heterocyclo or acyl.

The nitrogen atom of the sulfonamide moiety of the substituted heterocyclic mercaptosulfonamides of Formula 1 may be attached directly (i=0) to the heterocyclic ring, or via a linker carbon (i=1). When i is 1 and the sulfonamide nitrogen is attached via the carbon linker, the carbon atom may be substituted by a hydrocarbyl or substituted hydrocarbyl. Stated differently, when i is 1, $R_{3a}$ and $R_{3b}$ are independently hydrogen, hydrocarbyl, or substituted hydrocarbyl. Exemplary hydrocarbyl include lower alkyl, e.g., methyl, ethyl, propyl, or butyl. Exemplary substituted hydrocarbyl include substituted lower alkyl, e.g., substituted methyl, ethyl, propyl or butyl. In one embodiment, $R_{3a}$ and $R_{3b}$ are each hydrogen.

As noted, $R_1$ may be hydrocarbyl, substituted hydrocarbyl, or heterocyclo. In a preferred embodiment, $R_1$ is alkyl, aryl, heteroaryl, or substituted heteroaryl. In general, however, $R_1$ will be optionally substituted carbocyclic or heterocyclic. For example, $R_1$ may be an optionally substituted 5-membered or 6-membered carbocyclic or heterocyclic ring. In addition, such 5-membered and 6-membered rings may be fully saturated, partially unsaturated or (hetero)aromatic. In one embodiment, $R_1$ is optionally substituted cyclopentyl or cyclohexyl. In another embodiment, $R_1$ is optionally substituted phenyl. In another embodiment, $R_1$ is optionally substituted tetrahydrofuryl, tetrahydrothiophenyl, tetrahydropyrrolyl, piperidinyl, tetrahydropyranyl, or thianyl, piperazinyl, oxazinyl, dithianyl, dioxanyl, or triazinyl. In another embodiment, $R_1$ is optionally substituted pyrrolyl, furyl, thienyl, pyridinyl, pyranyl, thienyl, diazinyl, triazinyl, or thiazinyl. In one preferred embodiment, $R_1$ is phenyl or substituted phenyl. In another preferred embodiment, $R_1$ is diphenyl or diphenyl ether.

In general, $R_2$ may be selected from hydrogen, hydrocarbyl, substituted hydrocarbyl, and heterocyclo. Typically, however, $R_2$ will be hydrogen or lower alkyl, more typically hydrogen. In one embodiment, $R_2$ is methyl, ethyl, propyl, or butyl. In another embodiment, $R_2$ is substituted lower alkyl, e.g., substituted methyl, ethyl, propyl or butyl.

In one embodiment in which the substituted heterocyclic mercaptosulfonamide corresponds to Formula 1, "i" is zero; and the sulfonamide is directly bonded to the heterocycle as depicted in Formula 1A:

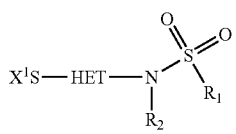

Formula 1A wherein HET is a five- or six-membered heterocycle containing, as heteroatoms, one ring nitrogen atom, two ring nitrogen atoms, or a ring nitrogen atom and a ring oxygen atom, and 4 or 5 carbon atoms; $R_1$ is hydrocarbyl, substituted hydrocarbyl, or heterocyclo; $R_2$ is hydrogen, hydrocarbyl, substituted hydrocarbyl, or heterocyclo; and $X^1$ is a cation, hydrogen or acyl.

For example, the substituted heterocyclic mercaptosulfonamide may correspond to Formula 1A and $X^1$ is hydrogen. By way of further example, the substituted heterocyclic mercaptosulfonamide may correspond to Formula 1A and $R_1$ is aryl, substituted aryl, or heterocyclo. By way of further example, the substituted heterocyclic mercaptosulfonamide may correspond to Formula 1A and $R_2$ is hydrogen, alkyl or substituted alkyl. By way of further example, the substituted heterocyclic mercaptosulfonamide may correspond to Formula 1A, $X^1$ is hydrogen, and $R_1$ is aryl, substituted aryl, or heterocyclo. By way of further example, the substituted heterocyclic mercaptosulfonamide may correspond to Formula 1A, $X^1$ is hydrogen and $R_2$ is hydrogen, alkyl or substituted alkyl. By way of further example, the substituted heterocyclic mercaptosulfonamide may correspond to Formula 1A, $R_1$ is aryl, substituted aryl, or heterocyclo, and $R_2$ is hydrogen, alkyl or substituted alkyl. By way of further example, the substituted heterocyclic mercaptosulfonamide may correspond to Formula 1A, $X^1$ is hydrogen, $R_1$ is aryl, substituted aryl, or heterocyclo, and $R_2$ is hydrogen, alkyl or substituted alkyl.

The substituted heterocyclic mercaptosulfonamides comprise a heterocyclic moiety, identified as "HET" in Formulae 1 and 1A. In general, HET is a five- or six-membered heterocycle containing, as heteroatoms, one ring nitrogen atom, two ring nitrogen atoms, or a ring nitrogen atom and a ring oxygen atom, and 4 or 5 carbon atoms. In one embodiment, the mercaptosulfonamides of the present invention generally correspond to Formula 1 and HET corresponds to formula HET-1:

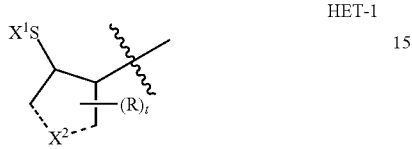

HET-1 wherein

designates the point of attachment of the heterocyclic ring to the remainder of the mercaptosulfonamide of Formula 1;

$A^-$ is a counteranion;

each R is independently hydrocarbyl, substituted hydrocarbyl, heterocyclo, or carbonyl (=O);

$R_{22}$ and $R_{23}$ are independently hydrogen, hydrocarbyl, substituted hydrocarbyl, or heterocyclo, or, $R_{22}$ and $R_{23}$, in combination, are carbonyl (=O);

t is an integer from 0 to 4, inclusive;

$X^1$ is a cation, hydrogen or acyl;

$X^2$ is —N($X^{20}$)—, —N($X^{20}$)O—, —N($X^{20}$)C($R_{22}$)($R_{23}$)—, —N($X^{20}$)N($X^{25}$)— or —N$^+$($X^{26}$)($X^{27}$)—A$^-$;

$X^{20}$ and $X^{25}$ are independently hydrogen, hydrocarbyl, substituted hydrocarbyl, heterocyclo, acyl, sulfonyl, phosphonyl, —O$X^{21}$, or —N$X^{23}X^{24}$, thionyl, or —C(S)$X^{28}$;

$X^{21}$ is hydrogen, hydrocarbyl, substituted hydrocarbyl or heterocyclo;

$X^{23}$ and $X^{24}$ are independently hydrogen, hydrocarbyl or heterocyclo, or, in combination with the nitrogen atom to which they are attached, form a heterocyclo ring;

$X^{26}$ and $X^{27}$ are independently hydrogen, hydrocarbyl, substituted hydrocarbyl, or in combination with the nitrogen atom to which they are attached, form a heterocyclo ring; and $X^{28}$ is hydrogen, hydrocarbyl, substituted hydrocarbyl, or heterocyclo.

In general, A- may be any pharmaceutically acceptable anion. It may be derived, for example, from inorganic acids, such as hydrochloric, hydrobromic, phosphoric, metaphosphoric, nitric, sulfonic, and sulfuric acids, organic acids such as acetic, benzenesulfonic, benzoic, citric, ethanesulfonic, fumaric, gluconic, glycolic, isothionic, lactic, lactobionic, maleic, malic, methanesulfonic, succinic, toluenesulfonic, tartaric, and trifluoroacetic acids, or any of the other acids mentioned herein to provide a pharmaceutically acceptable salt of the heterocyclic mercaptosulfonamide.

When the substituted heterocyclic mercaptosulfonamide corresponds to Formula 1 or 1A and "HET" is a five- or six-membered heterocycle corresponding to Formula HET-1, the substituted heterocyclic mercaptosulfonamide corresponds to Formula 2 or 2A, respectively,

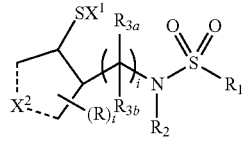

Formula 2

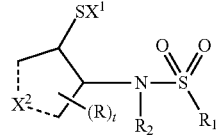

Formula 2A wherein i, R, $R_1$, $R_2$, $R_{3a}$, $R_{3b}$, t, $X^1$, and $X^2$ are as defined in connection with Formulae 1, 1A and HET-1. For example, the substituted heterocyclic mercaptosulfonamide may correspond to Formula 2 or 2A and $X^1$ is hydrogen. By way of further example, the substituted heterocyclic mercaptosulfonamide may correspond to Formula 2 or 2A and $R_1$ is aryl, substituted aryl, or heterocyclo. By way of further example, the substituted heterocyclic mercaptosulfonamide may correspond to Formula 2 or 2A and $R_2$ is hydrogen, alkyl or substituted alkyl. By way of further example, the substituted heterocyclic mercaptosulfonamide may correspond to Formula 2 or 2A, $X^1$ is hydrogen, and $R_1$ is aryl, substituted aryl, or heterocyclo. By way of further example, the substituted heterocyclic mercaptosulfonamide may correspond to Formula 2 or 2A, $X^1$ is hydrogen and $R_2$ is hydrogen, alkyl or substituted alkyl. By way of further example, the substituted heterocyclic mercaptosulfonamide may correspond to Formula 2 or 2A, $R_1$ is aryl, substituted aryl, or heterocyclo, and $R_2$ is hydrogen, alkyl or substituted alkyl. By way of further example, the substituted heterocyclic mercaptosulfonamide may correspond to Formula 2 or 2A, $X^1$ is hydrogen, $R_1$ is aryl, substituted aryl, or heterocyclo, and $R_2$ is hydrogen, alkyl or substituted alkyl. In each of these examples, i, R, $R_{3a}$, $R_{3b}$, t, and $X^2$ may be as defined in connection with Formula 1, 1A and HET-1.

As noted, the heterocyclic ring of Formulae 1, 1A, 2, 2A and HET-1 is a five or six-membered ring containing, as heteroatoms, one ring nitrogen atom, two ring nitrogen atoms, or a ring nitrogen atom and a ring oxygen atom, and 4 or 5 carbon atoms. When HET-1 is a five-membered ring, $X^2$ is preferably —N($X^{20}$)— or —N$^+$($X^{26}$)($X^{27}$)—A$^-$ wherein $X^{20}$, $X^{26}$, $X^{27}$ and A$^-$ are as defined in connection with Formula HET-1. When HET-1 is a six-membered ring, $X^2$ is preferably —N($X^{20}$)O—, —N($X^{20}$)C($R_{22}$)($R_{23}$)—, or —N($X^{20}$)N($X^{25}$)— wherein $R_{22}$, $R_{23}$, $X^{20}$, and $X^{25}$ are as defined in connection with Formula HET-1. In addition, when the heterocyclic ring is a six-membered ring, the chain atoms may be attached in either orientation, e.g., —N($X^{20}$)O— or —ON($X^{20}$)—, or —N($X^{20}$)C($R_{22}$)($R_{23}$)— or —C($R_{22}$)($R_{23}$)N($X^{20}$)—. Thus, for example, in a preferred embodiment HET-1 may correspond to any of Formulae HET-5, HET-5+, HET-6NN, HET-6NC, HET-6CN, HET-6NO, or HET-6ON:

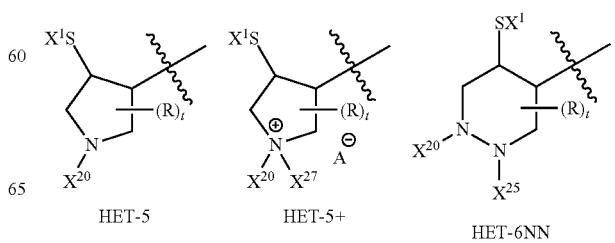

HET-5

HET-5+

HET-6NN

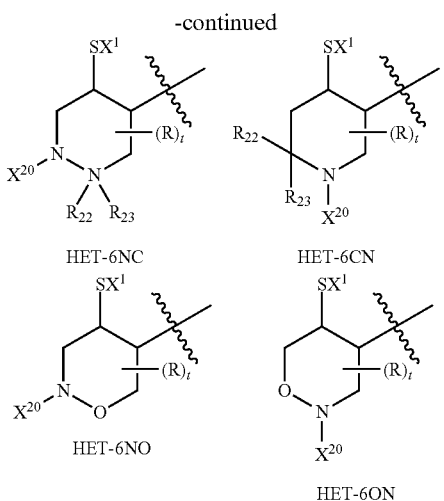

HET-6NC

HET-6CN

HET-6NO

HET-6ON wherein $A^-$, R, $R_{22}$, $R_{23}$, t, $X^1$, $X^{20}$, $X^{25}$, $X^{26}$, and $X^{27}$ are as defined in connection with Formula HET-1. For example, in one embodiment, the substituted heterocyclic mercaptosulfonamide corresponds to Formula 1 or 1A, HET corresponds to one of Formulae HET-5, HET-5+, HET-6NN, HET-6NC, HET-6CN, HET-6NO, and HET-6ON, and t is 0. By way of further example, in one embodiment the substituted heterocyclic mercaptosulfonamide corresponds to Formula 1 or 1A, HET corresponds to one of Formulae HET-5, HET-5+, HET-6NN, HET-6NC, HET-6CN, HET-6NO, and HET-6ON and $X^1$ is hydrogen. By way of further example, in one embodiment the substituted heterocyclic mercaptosulfonamide corresponds to Formula 1 or 1A, HET corresponds to one of Formulae HET-5, HET-5+, HET-6NN, HET-6NC, HET-6CN, HET-6NO, and HET-6ON, t is 0 and $X^1$ is hydrogen.

In general, in each of Formulae 1, 1A, 2, 2A, HET-1, HET-5, HET-5+, HET-6NN, HET-6NC, HET-6CN, HET-6NO, and HET-6ON, $X^{20}$ may be selected from hydrogen, hydrocarbyl, substituted hydrocarbyl, heterocyclo, acyl, sulfonyl, phosphonyl, —$OX^{21}$, —$NX^{23}X^{24}$, thionyl, or —C(S)$X^{28}$, where $X^{21}$, $X^{23}$, $X^{24}$, and $X^{28}$ are as defined in connection with Formula HET-1. For example, in one embodiment, $X^{20}$ is selected from hydrogen, hydrocarbyl, substituted hydrocarbyl, heterocyclo, acyl, sulfonyl, phosphonyl, or —$NX^{23}X^{24}$. By way of further example, $X^{20}$ may be selected from acyl, sulfonyl, and phosphonyl. In one preferred embodiment, $X^{20}$ is acyl. In another embodiment, $X^{20}$ is hydrogen. In another embodiment, $X^{20}$ is alkyl or substituted alkyl. In another embodiment, $X^{20}$ is a substituted hydrocarbyl such as polyethylene glycol or an optionally substituted hydrocarbyl linker, linking the heterocycle to a dye, radioactive label, paramagnetic moiety or other reporter group.

In another embodiment, the substituted heterocyclic mercaptosulfonamide corresponds to Formula 1 or 1A, HET corresponds to one of Formulae HET-5, HET-6NN, HET-6NC, HET-6CN, HET-6NO, and HET-6ON, and $X^{20}$ is acyl; for example, $X^{20}$ may be $X^{200}$C(O)— wherein $X^{200}$ is alkyl, substituted alkyl, $R^1R^2N$—, or $R^1O$—, where $R^1$ is hydrogen, hydrocarbyl, substituted hydrocarbyl, or heterocyclo, and $R^2$ is hydrogen, hydrocarbyl, substituted hydrocarbyl or heterocyclo. By way of further example, $X^{20}$ may be $X^{200}$C(O)— wherein $X^{200}$ is a heterocyclo ring such as furyl, thienyl, pyridyl, oxazolyl, pyrrolyl, inodolyl, quinolinyl, isoquinolinyl and the like. Exemplary substituents for $X^{200}$ where $X^{200}$ is a heterocyclo include, but are not limited to, hydrocarbyl, substituted hydrocarbyl, halo, amino, nitro, alkoxy, keto, hydroxy, protected hydroxy and acyl. In an embodiment, $X^{200}$ is acyl. In another embodiment, $X^{200}$ is alkyl or substituted alkyl. In a further embodiment, $X^{200}$ is a substituted hydrocarbyl such as polyethylene glycol or an optionally substituted hydrocarbyl linker, linking the heterocycle to a dye, radioactive label, paramagnetic moiety or other reporter group.

In another embodiment, the substituted heterocyclic mercaptosulfonamide corresponds to Formula 1 or 1A, HET corresponds to one of Formulae HET-5, HET-6NN, HET-6NC, HET-6CN, HET-6NO, and HET-6ON, and $X^{20}$ may be —$OX^{21}$ wherein $X^{21}$ is hydrogen, hydrocarbyl, substituted hydrocarbyl, or heterocyclo. In one such embodiment, $X^{21}$ is hydrogen. In another embodiment, $X^{21}$ is alkyl or substituted alkyl. In another embodiment, $X^{21}$ is aryl, preferably phenyl or substituted phenyl. In a further embodiment, $X^{21}$ is a substituted hydrocarbyl such as polyethylene glycol or an optionally substituted hydrocarbyl linker, linking the heterocycle to a dye, radioactive label, paramagnetic moiety or other reporter group.

In another embodiment, the substituted heterocyclic mercaptosulfonamide corresponds to Formula 1 or 1A, HET corresponds to Formula HET-5+, and $X^{20}$ is —$N^+(X^{26})(X^{27})$—$A^-$ wherein $X^{26}$ and $X^{27}$ are independently hydrogen, hydrocarbyl, substituted hydrocarbyl, or heterocyclo, or $X^{26}$ and $X^{27}$ in combination with the nitrogen atom to which they are attached form a heterocyclo ring such as morpholine, azepine, piperidine, or pyrrolidine. In one embodiment, $X^{26}$ and $X^{27}$ are aryl. In addition, $A^-$ is any pharmaceutically acceptable counteranion, including without limitation chloride, bromide, sulphate, phosphate, acid phosphate, acetate, maleate, fumarate, lactate, tartrate, citrate, gluconate, formate and ascorbate. For example, in one embodiment, $A^-$ may be chloride.

In another preferred embodiment, $X^{20}$ is a sulfonyl group. In one such embodiment, $X^{20}$ is sulfonyl, corresponding to the formula $Z^1SO_2$— wherein $Z^1$ is hydrocarbyl, substituted hydrocarbyl, heterocyclo, $R^1R^2N$—, or $R^1O$—, where $R^1$ is hydrogen, hydrocarbyl, substituted hydrocarbyl, or heterocyclo, and $R^2$ is hydrogen, hydrocarbyl, substituted hydrocarbyl or heterocyclo. In one such embodiment, $Z^1$ is alkyl. In another embodiment, $Z^1$ is phenyl or substituted phenyl. In a further embodiment, $Z^1$ is a substituted hydrocarbyl such as polyethylene glycol or an optionally substituted hydrocarbyl linker, linking the heterocycle to a dye, radioactive label, paramagnetic moiety or other reporter group. By way of further example, $X^{20}$ may be $Z^1SO_2$— wherein $Z^1$ is a heterocyclo ring such as furyl, thienyl, pyridyl, oxazolyl, pyrrolyl, inodolyl, quinolinyl, isoquinolinyl and the like. Exemplary substitutents for $Z^1$ where $Z^1$ is a heterocyclo include, but are not limited to, hydrocarbyl, substituted hydrocarbyl, halo, amino, nitro, alkoxy, keto, hydroxy, protected hydroxy and acyl.

In another preferred embodiment, $X^{20}$ is a phosphonyl group, corresponding to the formula $Z^2P(O)(OH)$— wherein $Z^2$ is hydrocarbyl, substituted hydrocarbyl, heterocyclo, $R^1R^2N$—, or $R^1O$—, where $R^1$ is hydrogen, hydrocarbyl, substituted hydrocarbyl, or heterocyclo, and $R^2$ is hydrogen, hydrocarbyl, substituted hydrocarbyl or heterocyclo. In one such embodiment, $Z^2$ is alkyl or substituted alkyl. In another embodiment, $Z^2$ is phenyl or substituted phenyl. In a further embodiment, $Z^2$ is a substituted hydrocarbyl such as polyethylene glycol or an optionally substituted hydrocarbyl linker, linking the heterocycle to a dye, radioactive label, paramagnetic moiety or other reporter group. By way of further example, $X^{20}$ may be $Z^2P(O)(OH)$— wherein $Z^2$ is a heterocyclo ring such as furyl, thienyl, pyridyl, oxazolyl, pyrrolyl, inodolyl, quinolinyl, isoquinolinyl and the like. Exemplary substitutents for $Z^2$ where $Z^2$ is a heterocyclo include, but are not limited to, hydrocarbyl, substituted hydrocarbyl, halo, amino, nitro, alkoxy, keto, hydroxy, protected hydroxy and acyl.

When the substituted heterocyclic mercaptosulfonamide corresponds to Formula 1 or 1A, HET corresponds to Formula HET-6NN, and $X^2$ is —N($X^{20}$) N($X^{25}$)—, $X^{25}$ may be selected from hydrogen, hydrocarbyl, substituted hydrocarbyl, heterocyclo, acyl, sulfonyl, phosphonyl, —$OX^{21}$, —$NX^{23}X^{24}$, thionyl, or —C(S)$X^{28}$ as previously defined in connection with $X^{20}$. Thus, for example, $X^{20}$ and $X^{25}$ may be the same or different. Preferably, $X^{20}$ and $X^{25}$ are the same.

In one embodiment in which the heterocyclic moiety, HET, corresponds to Formula HET-1, the mercaptosulfonamide corresponds to Formula 2B:

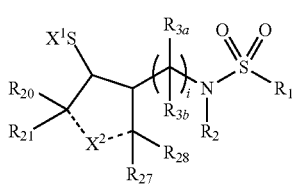

Formula 2B wherein
$A^-$ is a pharmaceutically acceptable counteranion;
i is 0 or 1;
$R_1$ is hydrocarbyl, substituted hydrocarbyl, or heterocyclo;
$R_2$ is hydrogen, hydrocarbyl, substituted hydrocarbyl, or heterocyclo;
$R_{3a}$ and $R_{3b}$, when i is 1, are independently hydrogen, hydrocarbyl, or substituted hydrocarbyl;
$R_{20}$, $R_{21}$, $R_{22}$, $R_{23}$, $R_{27}$ and $R_{28}$ are independently hydrogen, hydrocarbyl, substituted hydrocarbyl, or heterocyclo, or, $R_{20}$ and $R_{21}$, in combination, are carbonyl (=O), or, $R_{22}$ and $R_{23}$, in combination, are carbonyl (=O), or, $R_{27}$ and $R_{28}$, in combination, are carbonyl (=O);
$X^1$ is a cation, hydrogen or acyl;
$X^2$ is —N($X^{20}$)—, —N($X^{20}$)O—, —N($X^{20}$)C($R_{22}$)($R_{23}$)—, —N($X^{20}$)N($X^{25}$)—, or —$N^+$($X^{26}$)($X^{27}$)— $A^-$;
$X^{20}$ and $X^{25}$ are independently hydrogen, hydrocarbyl, heterocyclo, acyl, —$OX^{21}$, —$NX^{23}X^{24}$, thionyl, or —C(S)$X^{28}$;
$X^{21}$ is hydrogen, hydrocarbyl, substituted hydrocarbyl or heterocyclo;
$X^{23}$ and $X^{24}$ are independently hydrogen, hydrocarbyl or heterocyclo, or, in combination with the nitrogen atom to which they are attached, form a heterocyclo ring;
$X^{26}$ and $X^{27}$ are independently hydrogen, hydrocarbyl, substituted hydrocarbyl, or in combination with the nitrogen atom to which they are attached, form a heterocyclo ring; and
$X^{28}$ is hydrogen, hydrocarbyl, substituted hydrocarbyl, or heterocyclo.

The nitrogen atom of the sulfonamide moiety of the substituted heterocyclic mercaptosulfonamides of Formula 2B may be attached directly (i=0) to the heterocyclic ring, or via a linker carbon (i=1). When i is 1 and the sulfonamide nitrogen is attached via the carbon linker, the carbon atom may be substituted by a hydrocarbyl or substituted hydrocarbyl. Stated differently, when i is 1, $R_{3a}$ and $R_{3b}$ are independently hydrogen, hydrocarbyl, or substituted hydrocarbyl. Exemplary hydrocarbyl include lower alkyl, e.g., methyl, ethyl, propyl or butyl. In one embodiment, $R_{3a}$ and $R_{3b}$ are each hydrogen.

As noted, $R_1$ of the substituted heterocyclic mercaptosulfonamides of Formula 2B may be hydrocarbyl, substituted hydrocarbyl, or heterocyclo. In a preferred embodiment, $R_1$ is alkyl, aryl, heteroaryl, or substituted heteroaryl. In general, however, $R_1$ will be optionally substituted carbocyclic or heterocyclic. For example, $R_1$ may be an optionally substituted 5-membered or 6-membered carbocyclic or heterocyclic ring. In addition, such 5-membered and 6-membered rings may be fully saturated, partially unsaturated or (hetero) aromatic. In one embodiment, $R_1$ is optionally substituted cyclopentyl or cyclohexyl. In another embodiment, $R_1$ is optionally substituted phenyl. In another embodiment, $R_1$ is optionally substituted tetrahydrofuryl, tetrahydrothiophenyl, tetrahydropyrrolyl, piperidinyl, tetrahydropyranyl, or thianyl, piperazinyl, oxazinyl, dithianyl, dioxanyl, or triazinyl. In another embodiment, $R_1$ is optionally substituted pyrrolyl, furyl, thienyl, pyridinyl, pyranyl, thienyl, diazinyl, triazinyl, or thiazinyl. In one preferred embodiment, $R_1$ is phenyl or substituted phenyl. In another preferred embodiment, $R_1$ is diphenyl or diphenyl ether.

In general, $R_2$ of the substituted heterocyclic mercaptosulfonamides of Formula 2B may be selected from hydrogen, hydrocarbyl, substituted hydrocarbyl, and heterocyclo. Typically, however, $R_2$ will be hydrogen or lower alkyl, more typically hydrogen. In one embodiment, $R_2$ is methyl, ethyl, propyl, or butyl. In another embodiment, $R_2$ is substituted lower alkyl, e.g., substituted methyl, ethyl, propyl or butyl.

As previously noted, $X^1$ of the substituted heterocyclic mercaptosulfonamides of Formula 2B is a cation, hydrogen, or acyl. Typically, $X^1$ is hydrogen. In another embodiment, $X^1$ may be an alkali metal; for example, $X^1$ may be sodium or potassium. In a further embodiment, $X^1$ may be an alkaline earth metal; for example, $X^1$ may be magnesium or calcium. In other embodiments, $X^1$ may be aluminum or ammonium. In a further embodiment $X^1$ may be acyl; for example, $X^1$ may be RC(O)—, wherein R is $R^1$, $R^1$O—, $R^1R^2$N—, or $R^1$S—, wherein $R^1$ is hydrocarbyl, heterosubstituted hydrocarbyl, or heterocyclo and $R^2$ is hydrogen, hydrocarbyl or substituted hydrocarbyl. In another embodiment $X^1$ is $SX^{11}$, wherein $X^{11}$ is hydrocarbyl, substituted hydrocarbyl, heterocyclo or acyl.

As depicted in Formula 2B, the heterocyclic ring contains $X^2$ and at least four carbon atoms, one of which is substituted by $SX^1$, one of which is substituted by $R_{20}$ and $R_{21}$, and one of which is substituted by $R_{27}$ and $R_{23}$. In an embodiment, $R_{20}$ is hydrogen. In another embodiment, $R_{21}$ is hydrogen. In a further embodiment, $R_{20}$ and $R_{21}$ are both hydrogen. In an embodiment, $R_{27}$ is hydrogen. In another embodiment, $R_{28}$ is hydrogen. In a further embodiment, $R_{27}$ and $R_{28}$ are both hydrogen. The single dashed lines linking $X^2$ to the two carbons in the alpha position relative to $X^2$ indicate that $X^2$ may be directly bonded to each of these carbon atoms (in which case the heterocyclic ring is five membered), or that $X^2$ may be indirectly bonded to these carbon atoms by means of another ring atom (in which case the ring is a six membered ring).

As previously noted, $X^2$ of the substituted heterocyclic mercaptosulfonamides of Formula 2B may be —N($X^{20}$)—, —N($X^{20}$)O—, —N($X^{20}$)C($R_{22}$)($R_{23}$)—, —N($X^{20}$)N ($X^{25}$)—, or —$N^+$($X^{26}$)($X^{27}$)— $A^-$, wherein $A^-$, $R_{22}$, $R_{23}$, $X^{20}$, $X^{25}$, $X^{26}$ and $X^{27}$ are as previously defined. In one embodiment, $X^2$ is part of a five-membered saturated ring and $X^2$ is —N($X^{20}$)—, where $X^{20}$ is as previously defined in connection with Formulae 1, 1A, 2, 2A, HET-1, HET-5, HET-5+, HET-6NN, HET-6NC, HET-6CN, HET-6NO, and HET-6ON. In another embodiment, $X^2$ is part of a six-membered saturated ring and $X^2$ is —N($X^{20}$)O—, where $X^{20}$ is as previously defined in connection with Formulae 1, 1A, 2, 2A, HET-1, HET-5, HET-5+, HET-6NN, HET-6NC, HET-6CN, HET-6NO, and HET-6ON. In another embodiment, $X^2$ is part of a six-membered saturated ring and $X^2$ is —N($X^{20}$)C($R_{22}$)($R_{23}$)—, where $X^{20}$, $R_{22}$, and $R_{23}$ are as previously defined in connection with Formulae 1, 1A, 2, 2A, HET-1, HET-5, HET-5+, HET-6NN, HET-6NC, HET-6CN, HET-6NO, and HET-6ON. In another embodiment, $X^2$ is part of a six-membered saturated ring and $X^2$ is —N($X^{20}$)N($X^{25}$)—, where $X^{20}$ and $X^{25}$ are as previously defined in connection with Formulae 1, 1A, 2, 2A, HET-1, HET-5, HET-5+, HET-6NN, HET-6NC, HET-6CN, HET-6NO, and HET-6ON. In another embodiment, $X^2$ is part of a five-membered saturated ring and $X^2$ is —N$^+$($X^{26}$)($X^{27}$)— A$^-$, where $X^{26}$, $X^{27}$ and A$^-$ are as previously defined in connection with Formula HET-1. In each of these embodiments, when $X^2$ is part of a five-membered saturated ring, $X^2$ is covalently bonded directly to the carbon atoms linked to $X^2$ by the dashed lines in Formula 2B. When $X^2$ is part of a six-membered saturated ring, $X^2$ is covalently bonded directly to one of the two carbon atoms linked to $X^2$ by the dashed lines in Formula 2B, and indirectly bonded to the other by means of another ring atom. In each of these embodiments, the ring of which $X^2$ is a part is fully saturated.

When $X^2$ of the substituted heterocyclic mercaptosulfonamides of Formula 2B is —N($X^{20}$)—, $X^{20}$ may be selected from hydrogen, hydrocarbyl, substituted hydrocarbyl, heterocyclo, acyl, sulfonyl, phosphonyl, —O$X^{21}$, —N$X^{23}X^{24}$, thionyl, or —C(S)$X^{28}$; where $X^{21}$, $X^{23}$, $X^{24}$ and $X^{28}$ are as previously defined in connection with Formulae HET-5, HET-6NN, HET-6NC, HET-6CN, HET-6NO, and HET-6ON. In one embodiment, $X^{20}$ is hydrogen. In another embodiment, $X^{20}$ is acyl as described in connection with Formulae HET-5, HET-6NN, HET-6NC, HET-6CN, HET-6NO, and HET-6ON.

In one preferred embodiment, i is 0; stated differently, in this embodiment, the nitrogen atom of the sulfonamide moiety is bonded directed to the heterocyclic ring as depicted in Formula 2C:

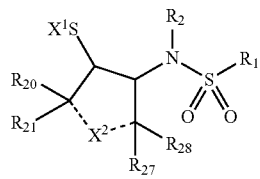

Formula 2C wherein $R_1$, $R_2$, $R_{20}$, $R_{21}$, $R_{27}$, $R_{28}$, $X^1$, and $X^2$ are as defined in connection with Formula 2B. In this embodiment, for example, the heterocyclic ring may be pyrrolidinyl or piperidinyl.

In general, when the heterocyclic ring corresponds to Formula HET-1 and is a 5-membered pyrrolyl ring, $X^2$ is —N($X^{20}$)— or —N$^+$($X^{26}$)($X^{27}$)— A$^-$, and the substituted heterocyclic mercaptosulfonamide corresponds to Formulae 2D or 2E:

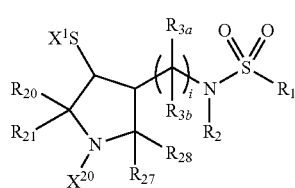

Formula 2D

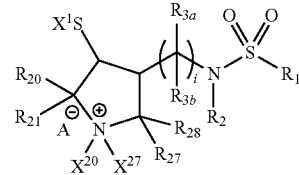

Formula 2E wherein A$^-$, i, $R_1$, $R_2$, $R_{3a}$, $R_{3b}$, $R_{20}$, $R_{21}$, $R_{27}$, $R_{28}$, $X^1$, $X^{20}$, $X^{26}$ and $X^{27}$ are as defined in connection with Formula 2B.

In one preferred embodiment, the mercaptosulfonamides of the present invention correspond to Formula 2D or Formula 2E, and i is 0; stated differently, in this embodiment, the nitrogen atom of the sulfonamide moiety is bonded directed to the heterocyclic ring. In this embodiment, the mercaptosulfonamides correspond to Formulae 2F or 2G:

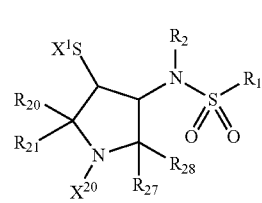

Formula 2F

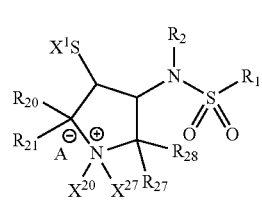

Formula 2G wherein A$^-$, $R_1$, $R_2$, $R_{20}$, $R_{21}$, $R_{27}$, $R_{28}$, $X^1$, $X^{20}$, $X^{26}$, $X^{27}$ and A$^-$ are as defined in connection with Formula 2B.

In general, when the heterocyclic ring corresponds to Formula 1 and HET-1 is a 6-membered ring, $X^2$ is —N($X^{20}$)C($R_{22}$)($R_{23}$)—, —C($R_{22}$)($R_{23}$)N($X^{20}$)—, —N($X^{20}$)O—, —ON($X^{20}$)—, or —N($X^{20}$)N($X^{25}$)—, and the mercaptosulfonamide corresponds to Formulae 3A, 3B, 3C, 3D, or 3E, respectively:

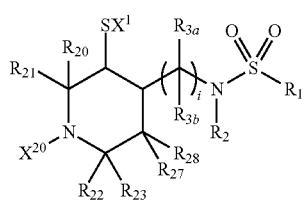

Formula 3A

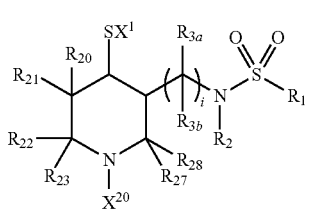

Formula 3B

Formula 3C
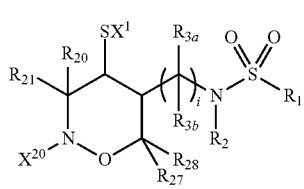

Formula 3D
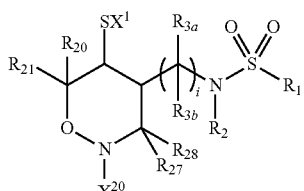

Formula 3E
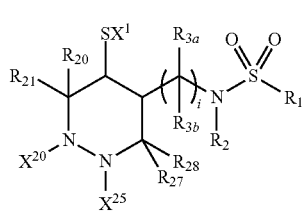

wherein i, $R_1$, $R_2$, $R_{3a}$, $R_{3b}$, $R_{20}$, $R_{21}$, $R_{27}$, $R_{28}$, $X^1$, $X^{20}$, $X^{21}$, $X^{23}$, $X^{24}$ and $X^{28}$ are as defined in connection with Formula 2B; $R_{22}$ and $R_{23}$ are independently hydrogen, hydrocarbyl, substituted hydrocarbyl or heterocyclo, or in combination, are carbonyl (=O); and $X^{25}$ is hydrogen, hydrocarbyl, substituted hydrocarbyl, heterocyclo, acyl, sulfonyl, phosphonyl, —$OX^{21}$, —$NX^{23}X^{24}$, thionyl or —$C(S)X^{28}$.

The nitrogen atom of the sulfonamide moiety of the substituted heterocyclic mercaptosulfonamides of Formulae 3A, 3B, 3C, 3D and 3E may be attached directly (i=0) to the heterocyclic ring, or via a linker carbon (i=1). When i is 1 and the sulfonamide nitrogen is attached via the carbon linker, the carbon atom may be substituted by a hydrocarbyl or substituted hydrocarbyl. Stated differently, when i is 1, $R_{3a}$ and $R_{3b}$ are independently hydrogen, hydrocarbyl, or substituted hydrocarbyl. Exemplary hydrocarbyl include lower alkyl, e.g., methyl, ethyl, propyl, etc. In one embodiment, $R_{3a}$ and $R_{3b}$ are each hydrogen.

As noted, $R_1$ of the substituted heterocyclic mercaptosulfonamides of Formulae 3A, 3B, 3C, 3D and 3E may be hydrocarbyl, substituted hydrocarbyl, or heterocyclo. In a preferred embodiment, $R_1$ is alkyl, aryl, heteroaryl, or substituted heteroaryl. In general, however, $R_1$ will be optionally substituted carbocyclic or heterocyclic. For example, $R_1$ may be an optionally substituted 5-membered or 6-membered carbocyclic or heterocyclic ring. In addition, such 5-membered and 6-membered rings may be fully saturated, partially unsaturated or (hetero)aromatic. In one embodiment, $R_1$ is optionally substituted cyclopentyl or cyclohexyl. In another embodiment, $R_1$ is optionally substituted phenyl. In another embodiment, $R_1$ is optionally substituted tetrahydrofuryl, tetrahydrothiophenyl, tetrahydropyrrolyl, piperidinyl, tetrahydropyranyl, or thianyl, piperazinyl, oxazinyl, dithianyl, dioxanyl, or triazinyl. In another embodiment, $R_1$ is optionally substituted pyrrolyl, furyl, thienyl, pyridinyl, pyranyl, thienyl, diazinyl, triazinyl, or thiazinyl. In one preferred embodiment, $R_1$ is phenyl or substituted phenyl. In another preferred embodiment, $R_1$ is diphenyl or diphenyl ether.

In general, $R_2$ of the substituted heterocyclic mercaptosulfonamides of Formulae 3A, 3B, 3C, 3D and 3E may be selected from hydrogen, hydrocarbyl, substituted hydrocarbyl, and heterocyclo. Typically, however, $R_2$ will be hydrogen or lower alkyl, more typically hydrogen. In one embodiment, $R_2$ is methyl.

As previously noted, $X^1$ of the substituted heterocyclic mercaptosulfonamides of Formulae 3A, 3B, 3C, 3D and 3E is a cation, hydrogen, or acyl. Typically, $X^1$ is hydrogen. In another embodiment, $X^1$ may be an alkali metal; for example, $X^1$ may be sodium or potassium. In a further embodiment, $X^1$ may be an alkaline earth metal; for example, $X^1$ may be magnesium or calcium. In other embodiments, $X^1$ may be aluminum or ammonium. In a further embodiment $X^1$ may be acyl; for example, $X^1$ may be RC(O)—, wherein R is $R^1$, $R^1O$—, $R^1R^2N$—, or $R^1S$—, wherein $R^1$ is hydrocarbyl, heterosubstituted hydrocarbyl, or heterocyclo and $R^2$ is hydrogen, hydrocarbyl or substituted hydrocarbyl. In another embodiment $X^1$ is $SX^{11}$, wherein $X^{11}$ is hydrocarbyl, substituted hydrocarbyl, heterocyclo or acyl.

As depicted in Formulae 3A, 3B, 3C, 3D, and 3E, the heterocyclic ring contains four or five carbon atoms, one of which is substituted by $SX^1$, one of which is substituted by $R_{20}$ and $R_{21}$, and one of which is substituted by $R_{27}$ and $R_{28}$. In Formulae 3A and 3B, an additional carbon atom is substituted by $R_{22}$ and $R_{23}$. In an embodiment, $R_{20}$ is hydrogen. In another embodiment, $R_{21}$ is hydrogen. In a further embodiment, $R_{20}$ and $R_{21}$ are both hydrogen. In an embodiment, $R_{22}$ is hydrogen. In another embodiment, $R_{23}$ is hydrogen. In a further embodiment, $R_{22}$ and $R_{23}$ are both hydrogen. In an embodiment, $R_{27}$ is hydrogen. In another embodiment, $R_{28}$ is hydrogen. In a further embodiment, $R_{27}$ and $R_{28}$ are both hydrogen.

In one preferred embodiment, the mercaptosulfonamides of the present invention generally correspond to one of Formulae 3A-3E, i is 0; stated differently, in this embodiment, the nitrogen atom of the sulfonamide moiety is bonded directed to the heterocyclic ring, and the mercaptosulfonamides correspond to one of Formulae 3AA-3EE:

Formula 3AA
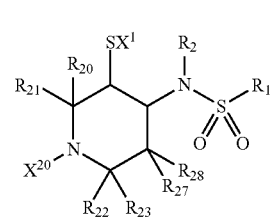

Formula 3BB
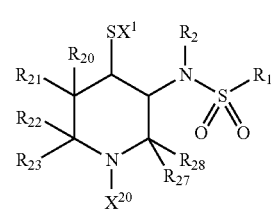

Formula 3CC
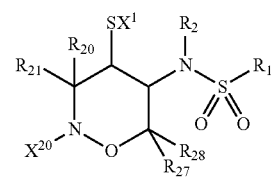

-continued

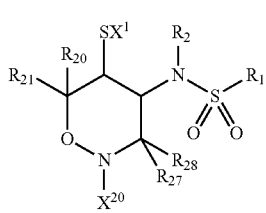

Formula 3DD

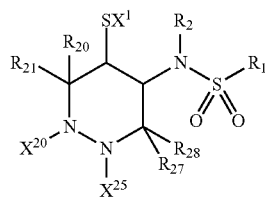

Formula 3EE wherein $R_1$, $R_2$, $R_{20}$, $R_{21}$, $R_{22}$, $R_{23}$, $R_{27}$, $R_{28}$, $X^1$, $X^{20}$ and $X^{25}$ are as defined in connection with Formulae 3A, 3B, 3C, 3D, and 3E.

In one preferred embodiment, the mercaptosulfonamides of the present invention generally correspond to Formula 4:

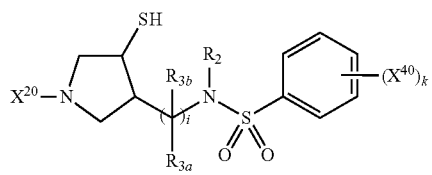

Formula 4 wherein i, $R_2$, $R_{3a}$, $R_{3b}$, and $X^{20}$ are as defined in connection with Formulae 2 and 2B. In this embodiment, k is an integer from 1 to 5, inclusive, and each $X^{40}$ is independently hydrocarbyl, substituted hydrocarbyl, halo, amino, nitro, hydroxy, alkoxy, acyl, or heterocyclo. Typically, k will be 1-3. In one embodiment, k is 3; for example, when k is 3, each $X^{40}$ may be halo (such as fluoro). In another embodiment, k will be 1. In one such embodiment, k is 1 and $X^{40}$ is hydrocarbyl such as alkyl or aryl, or alkoxy. In a preferred embodiment, $X^{40}$ is aryl, typically phenyl or substituted phenyl. In one preferred embodiment, $X^{20}$ is hydrogen, hydrocarbyl, substituted hydrocarbyl, heterocyclo, acyl, sulfonyl, phosphonyl, or —$NX^{23}X^{24}$ where $X^{23}$ and $X^{24}$ are as previously defined in connection with Formula HET-1. In one preferred embodiment, $X^{20}$ is hydrogen or acyl.

As previously noted, in one embodiment, the sulfonamide moiety is directly bonded to the heterocyclic ring; stated differently, i is 0, and the mercaptosulfonamide of Formula 4 corresponds to Formula 4A:

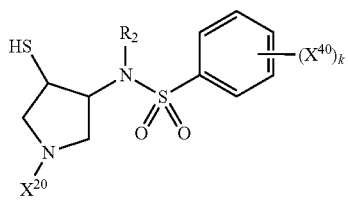

Formula 4A wherein k, $R_2$, $X^{20}$ and $X^{40}$ are as defined in connection with Formula 4.

In one preferred embodiment, the mercaptosulfonamides of the present invention generally correspond to Formula 5:

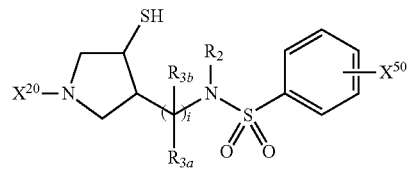

Formula 5 wherein i, $R_2$, $R_{3a}$, $R_{3b}$, and $X^{20}$ are as defined in connection with Formula 4. In this embodiment, $X^{50}$ is hydrocarbyl, substituted hydrocarbyl, halo, amino, nitro, hydroxy, alkoxy, acyl, or heterocyclo. In one such embodiment, $X^{50}$ is hydrocarbyl such as alkyl or aryl, or alkoxy. In a preferred embodiment, $X^{50}$ is phenyl or substituted phenyl. In one preferred embodiment, $X^{20}$ is hydrogen, acyl, hydrocarbyl, substituted hydrocarbyl, heterocyclo, sulfonyl, phosphonyl, or —$NX^{23}X^{24}$ where $X^{23}$ and $X^{24}$ are as previously defined in connection with Formula HET-1. In one preferred embodiment, $X^{20}$ is hydrogen or acyl.

As previously noted, in one embodiment, the sulfonamide moiety is directly bonded to the heterocyclic ring when i is 0, and in such an embodiment, the mercaptosulfonamide of Formula 5 corresponds to Formula 5A:

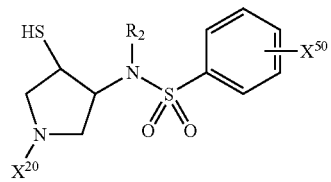

Formula 5A wherein $R_2$, $X^{20}$ and $X^{50}$ are as defined in connection with Formula 5.

In one preferred embodiment, the mercaptosulfonamides of the present invention generally correspond to Formula 6:

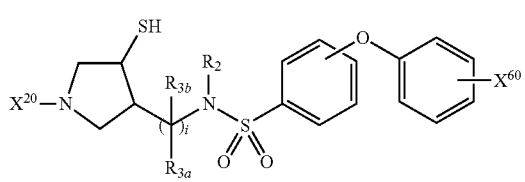

Formula 6 wherein i, $R_2$, $R_{3a}$, $R_{3b}$, and $X^{20}$ are as defined in connection with Formula 5. In this embodiment, $X^{60}$ is hydrocarbyl, substituted hydrocarbyl, halo, amino, nitro, hydroxy, alkoxy, acyl, or —$C(O)X^{61}$ and $X^{61}$ is hydroxy, amino or alkoxy. In one such embodiment, $X^{60}$ is hydrocarbyl such as alkyl, aryl or alkoxy. In one preferred embodiment, $X^{20}$ is hydrogen, acyl, hydrocarbyl, substituted hydrocarbyl, heterocyclo, sulfonyl, phosphonyl, or —$NX^{23}X^{24}$ where $X^{23}$ and $X^{24}$ are as previously defined in connection with Formula HET-1. In a further preferred embodiment, $X^{20}$ is hydrogen or acyl.

As previously noted, in one embodiment, i is 0 and the sulfonamide moiety is directly bonded to the heterocyclic ring, and the mercaptosulfonamide of Formula 6 corresponds to Formula 6A:

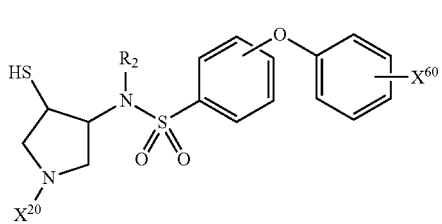

Formula 6A wherein $R_2$, $X^{20}$ and $X^{60}$ are as defined in connection with Formula 6.

In one preferred embodiment, the mercaptosulfonamides of the present invention generally correspond to Formula 7:

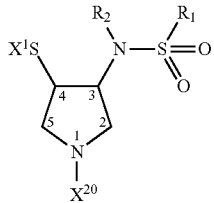

Formula 7 wherein $R_1$, $R_2$, $X^1$, and $X^{20}$ are as defined in connection with Formula 2, 2A, HET-5, and HET-5+, and the numbering scheme for the heterocyclo ring atoms corresponds to Formula 7.

In a preferred embodiment, the sulfonamide substituent and the sulfide substituent, on the 3-carbon and the 4-carbon of the heterocyclo ring respectively, as identified by number in Formula 7, have the trans stereochemical orientation, and the mercaptosulfonamides are exemplified by the following Formula 7a or Formula 7b:

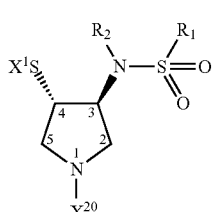

Formula 7a

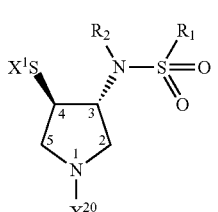

Formula 7b wherein $R_1$, $R_2$, $X^1$, and $X^{20}$ are as defined in connection with Formula 7.

In another embodiment, the sulfonamide substituent and the sulfide substituent, on the 3-carbon and the 4-carbon of the heterocyclo ring respectively, as identified by number in Formula 7, have the cis stereochemical orientation, and the mercaptosulfonamides are exemplified by the following Formula 8a or Formula 8b:

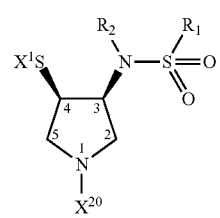

Formula 8a

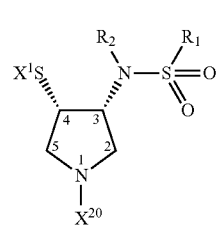

Formula 8b wherein $R_1$, $R_2$, $X^1$, and $X^{20}$ are as defined in connection with Formula 7. Similar to Formulae 7a, 7b, 8a and 8b, the cis- and trans-stereochemical orientation exists for each of Formulae 1-6 with respect to the corresponding ring carbons of the 5- or 6-membered heterocyclic rings substituted by the sulfonamide and the sulfide moieties. In the interests of brevity, each of these Formulae were presented without stereochemistry. Since the compounds of the present invention have several asymmetric carbons, it is known to those skilled in the art that the compounds of the present invention having asymmetric carbon atoms may exist in diastereometric, racemic, or optically active forms. All of these forms are contemplated within the scope of this invention. More specifically, the present invention includes the enantiomers, diastereomers, racemic mixtures, and other optically active mixtures of the compounds disclosed herein.

Synthesis

MMP inhibitors (MMPIs) of the general Formula 1 may be obtained according to the following schemes. In general, an epoxide of a five-membered or six-membered heterocycle (generally corresponding to HET-1) is treated with an azide, the reaction product is further derivatized to form an N-sulfonyl aziridine, the N-sulfonyl aziridine is treated with a mercaptan and further derivatized to provide the substituted heterocyclic mercaptosulfonamide compositions of the present invention. For example, a compound corresponding to Formula 2 (when i=0) or Formula 2a may be obtained according to Reaction Scheme 1 or Reaction Scheme 2:

Reaction Scheme 1. The synthesis of mercaptosulfonamide MMPIs with i=0, $R_2$=H.

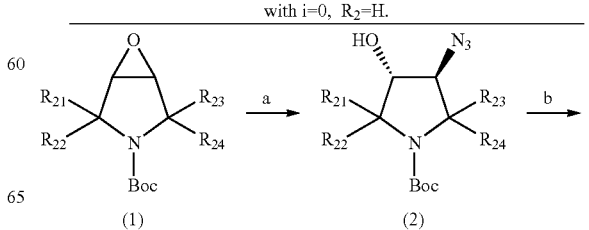

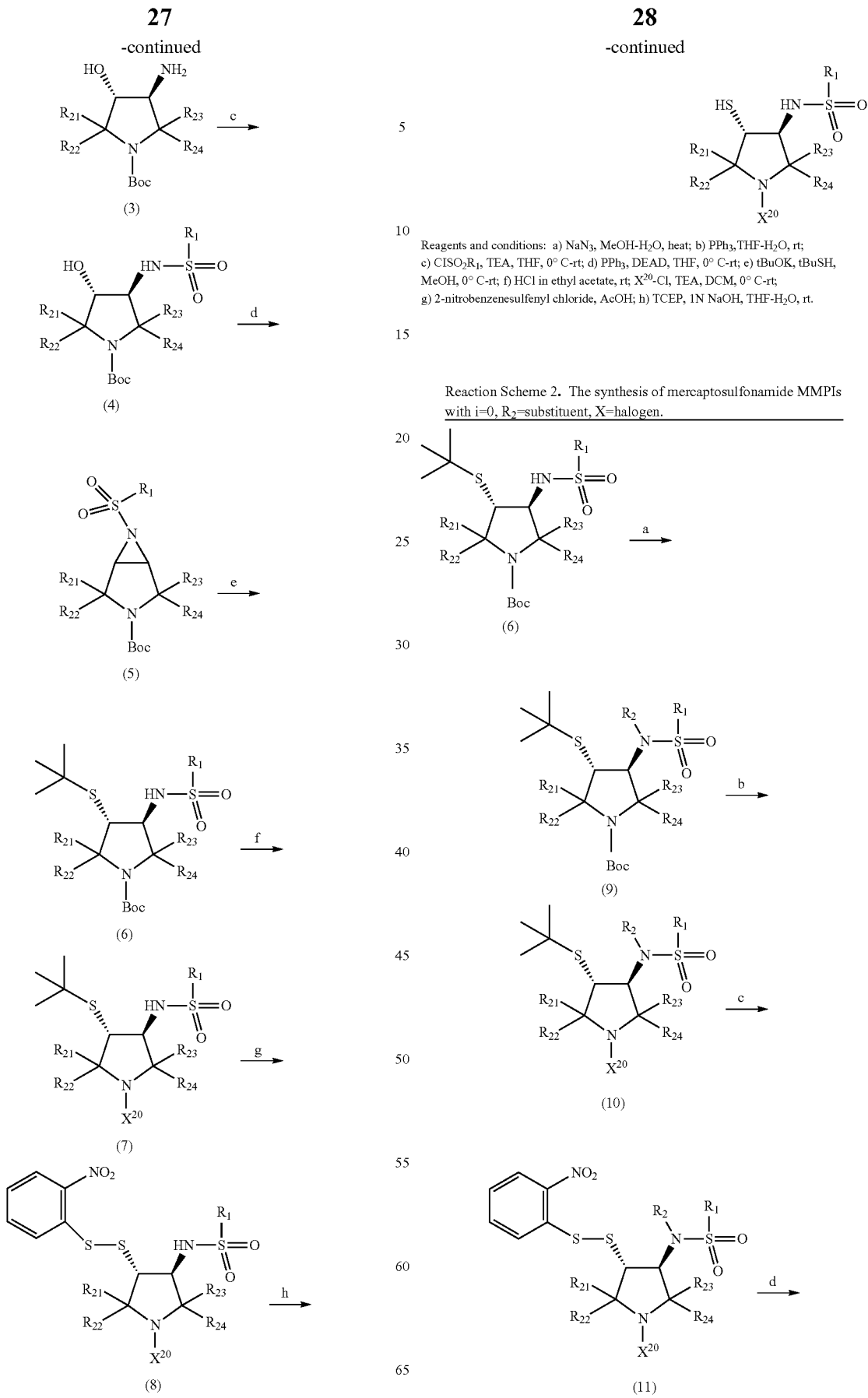
Reagents and conditions: a) NaN$_3$, MeOH-H$_2$O, heat; b) PPh$_3$, THF-H$_2$O, rt; c) ClSO$_2$R$_1$, TEA, THF, 0° C-rt; d) PPh$_3$, DEAD, THF, 0° C-rt; e) tBuOK, tBuSH, MeOH, 0° C-rt; f) HCl in ethyl acetate, rt; X$^{20}$-Cl, TEA, DCM, 0° C-rt; g) 2-nitrobenzenesulfenyl chloride, AcOH; h) TCEP, 1N NaOH, THF-H$_2$O, rt.
Reaction Scheme 2. The synthesis of mercaptosulfonamide MMPIs with i=0, R$_2$=substituent, X=halogen.

-continued

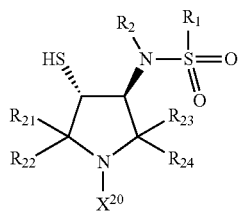

Reagents and conditions: a) R₂X, tBuOK, DMF, 0° C-rt; b) HCl in ethyl acetate, rt; X²⁰-Cl, TEA, DCM, 0° C-rt; c) 2-nitrobenzenesulfenyl chloride, AcOH, rt; d) TCEP, 1N NaOH, THF-H₂O, rt.

When the substituted heterocyclic mercaptosulfonamide compositions correspond to Formula 2 and i=1, MMPs of the general Formula 2 may be obtained according to the following Reaction Scheme 3:

Reaction Scheme 3. The synthesis of mercaptosulfonamide MMPIs with i = 1. Reagents and conditions: a) KCN, EtOH, heat; b) BH₃, THF; c) NaHCO₃, R₁SO₂Cl, 0° C. - rt; d) MeSO₂Cl, TEA, DCM, rt; (ii) AcOK, DMF, 100° C.; e) LiOH, THF—MeOH—H₂O, rt; thiolacetic acid, PPh₃, DEAD, 0° C. - rt; f) MeNH₂, MeOH, rt; 2-nitrobenzenesulfenyl chloride, DCM, rt; g) TFA, rt; X²⁰—Cl, TEA, DCM, 0° C. - rt; h) TCEP, 1N NaOH, THF—H₂O, rt.

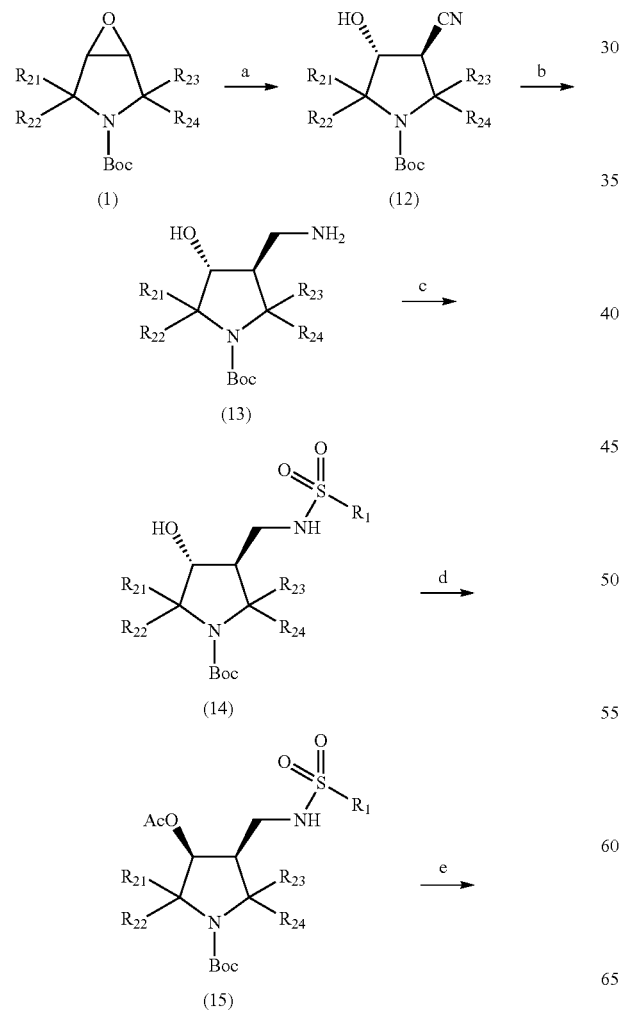

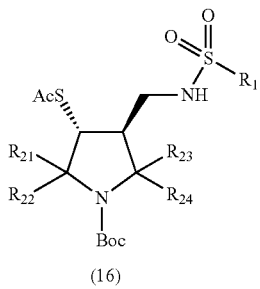

(16)

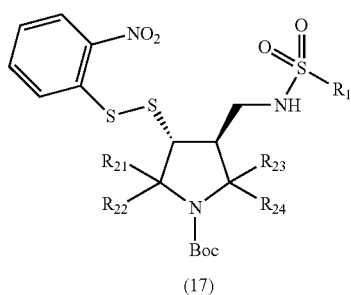

(17)

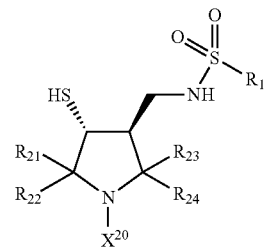

The synthesis of enantiopure mercaptosulfonamide MMPI's of the general Formula 1 may be obtained according to the Reaction Scheme 4:

Reaction Scheme 4. The synthesis of enantiopure mercaptosulfonamide MMPIs with i=0, R₂ & R₂₁-R₂₄=H.

A:

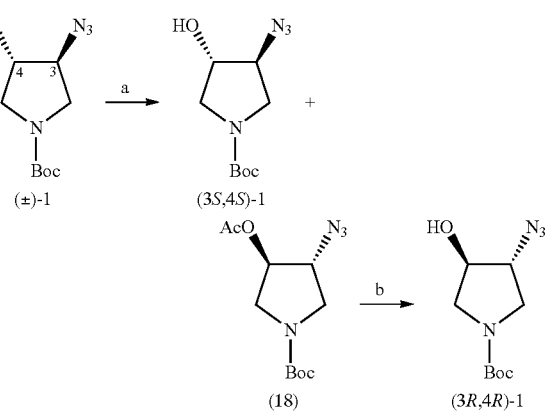

B:

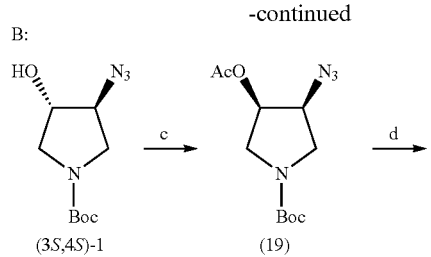

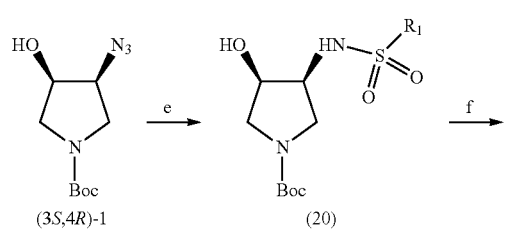

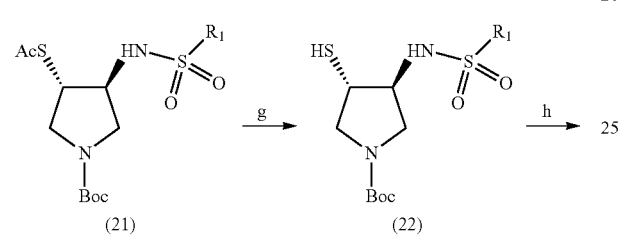

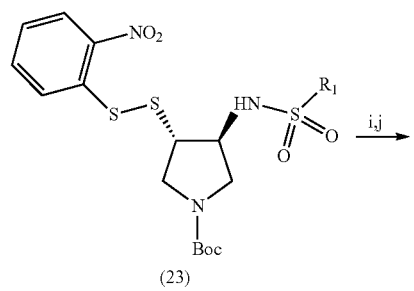

C:

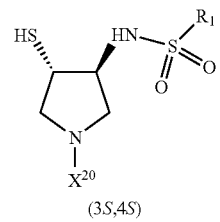

Reagents and conditions: a) Amano AK-20 lipase, *tert*-butyl methyl ether, isopropenyl acetate, rt; b) LiOH, THF-MeOH-H$_2$O, rt; c) (i) MeSO$_2$Cl, TEA, DCM, rt; (ii) AcOK, DMF, 100° C; d) LiOH, THF-MeOH-H$_2$O, rt; e) PPh$_3$, THF-H$_2$O; NaHCO$_3$, R$_1$SO$_2$Cl, 0° C-rt; f) thiolacetic acid, PPh$_3$, DEAD, 0° C-rt; g) MeNH$_2$, MeOH, rt; h) 2-nitrobenzenesulfenyl chloride, DCM, rt; i) TFA, rt; X$^{20}$-Cl, TEA, DCM, 0° C-rt; j) TCEP, 1N NaOH, THF-H$_2$O, rt.

The synthesis of six-membered heterocyclic mercaptosulfonamide MMPIs of the general Formula 1 may be obtained according to Reaction Scheme 5 (wherein X and Y in combination are —N—O—, —O—N—, —C—N—, —N—C—, or —N—N—):

Reaction Scheme 5. The synthesis of heterocyclic 6-membered ring MMPIs.

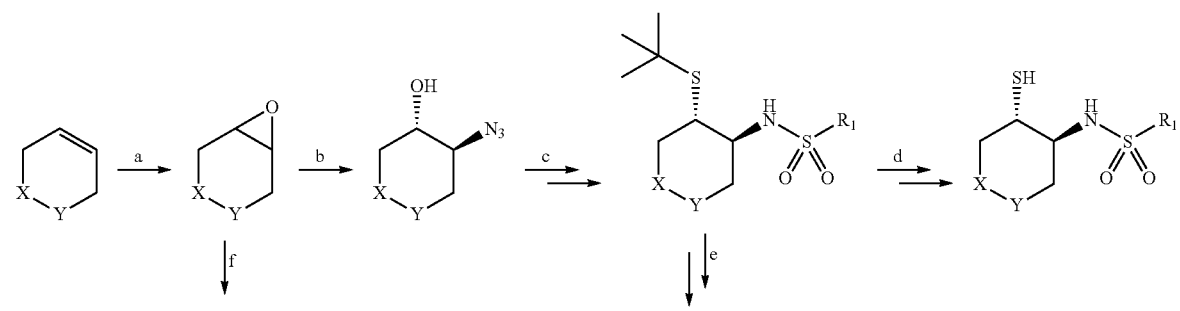

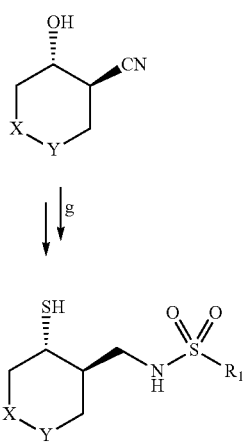
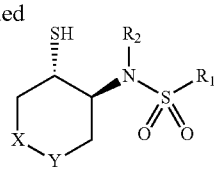

Reagents and conditions: a) m-chloroperbenzoic acid, DCM; b) NaN₃, MeOH-H₂O, heat; c) as in Scheme 1; d) as in Scheme 1; e) as in Scheme 2; f) KCN, EtOH, heat; g) as in Scheme 3.

Pharmaceutical Compositions

Compounds of the instant invention are useful for treating various diseases which may benefit from modulation of matrix metalloproteinases by heterocyclic mercaptosulfonamide inhibitors. Compounds of the instant invention may be used in mammals including humans, and are preferably administered in the form of a pharmaceutical composition comprising an effective amount of a compound of the instant invention in combination with at least one pharmaceutically or pharmacologically acceptable carrier. The carrier, also known in the art as an excipient, vehicle, auxiliary, adjuvant, or diluent, is any substance which is pharmaceutically inert, confers a suitable consistency or form to the composition, and does not diminish the therapeutic efficacy of the mercaptosulfonamide compounds. The carrier is "pharmaceutically or pharmacologically acceptable" if it does not produce an adverse, allergic or other untoward reaction when administered to a mammal or human, as appropriate.

The active agent prepared according to the present invention may thus be formulated into any suitable composition form for administration to a human or non-human animal patient.

The composition may consist of the active agent alone or may include the active agent and any suitable additional component, such as one or more pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier must be acceptable in the sense of being compatible with the other ingredients of the formulation and not injurious to the patient.

Excipients employed in the compositions of the present invention can be solids, semi-solids, liquids or combinations thereof. Preferably, the excipients are solids. Compositions of the invention containing excipients can be prepared by any known technique that comprises, for example, admixing an excipient with a substituted heterocyclic mercaptosulfonamide. A pharmaceutical, foodstuff, nutritional supplement, or nutraceutical composition of the invention contains a desired amount of mercaptosulfonamide and, optionally, an active pharmaceutical ingredient ("API") per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the present invention, such as tablets or capsules.

Compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colorcon™ 1500), clays (e.g., Veegum™ HV of R. T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; polyethylene glycol; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Compositions of the invention optionally comprise one or more pharmaceutically acceptable wetting agents such as surfactants. Such wetting agents are preferably selected to maintain a crystal in close association with water, a condition that is believed to improve bioavailability of the composition. Such wetting agents can also be useful in solubilizing or increasing the solubility of crystals.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees Ctoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

The composition may, for example, be a pharmaceutical composition (medicament), a foodstuff, food supplement or beverage. The terms "foodstuff", "food supplement", "nutritional supplement", and "beverage" used herein have the normal meanings for those terms, and are not restricted to pharmaceutical preparations. The appropriate pharmaceutical or edible grade of ingredients will be used, according to the desired composition form.

Pharmaceutical compositions according to the present invention include formulations suitable for oral, rectal, intranasal, topical (including transdermal, buccal and sublingual), vaginal, parental (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with a suitable carrier, such as liquid carriers or finely divided solid carriers or both, and then if necessary shaping the product. Formulations of the subject invention suitable for oral administration can be presented as discrete units such as capsules, cachets or tablets, each containing a predetermined amount of the active ingredient; or as an oil-in-water liquid emulsion, water-in-oil liquid emulsion, or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier; and chocolate comprising the active ingredients.

Formulations suitable for topical administration according to the subject invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Topical formulations preferably comprise compounds that facilitate absorption of the active ingredients through the skin and into the bloodstream.

Formulations suitable for intranasal administration, wherein the carrier is a solid, include a coarse powder having a particle size, for example, in the range of about 20 to about 500 microns, which is administered in the manner in which snuff is taken, i.e., by rapid inhalation through the nasal passage from a container of the powder held close up to the nose. Suitable formulations wherein the carrier is a liquid for administration by nebulizer include aqueous or oily solutions of the agent. Formulations preferably comprise compounds that facilitate absorption of the active ingredients through the skin and into the bloodstream.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose or multi-dose sealed containers, such as for example, ampoules and vials, and can be stored in a freeze-dried (lyophilized) condition requiring only the addition of the sterile liquid carrier, for example, water for injections, immediately prior to use. Extemporaneous injection solutions and suspensions can be prepared from sterile powders, granules and tablets of the kind previously described.

It should be understood that in addition to the ingredients particularly mentioned above, the formulations useful in the present invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known in the art and can be used to administer a therapeutic agent or composition of the invention, e.g., encapsulation in liposomes, microparticles, microcapsules, receptor-mediated endocytosis and the like. Methods of administration include, but are not limited to, parenteral, intra-arterial, intramuscular, intravenous, intranasal, and oral routes. The pharmaceutical compositions can be provided in the form of tablets, lozenges, granules, capsules, pills, ampoule, suppositories or aerosol form. The pharmaceutical compositions can also be provided in the form of suspensions, solutions, and emulsions of the active ingredient in aqueous or non-aqueous diluents, syrups, granulates or powders.

In one embodiment, the compositions of the present invention can be administered locally to the area in need of treatment; such local administration can be achieved, for example, by local infusion during surgery, by injection, or by means of a catheter. In another embodiment, a compound or composition of the invention is administered in a manner so as to achieve peak concentrations of the active compound at sites of the disease. Peak concentrations at disease sites can be achieved, for example, by intravenously injecting of the agent, optionally in saline, or orally administering, for example, a tablet, capsule or syrup containing the active ingredient.

Substituted heterocyclic mercaptosulfonamide compositions of the invention can be administered simultaneously or sequentially with other nutraceuticals, foodstuffs, drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, timerelease binders, anesthetics, steroids and corticosteroids.

Preferred unit dosage formulations are those containing a daily dose or unit, daily subdose, or an appropriate fraction thereof, of an agent. Therapeutic amounts can be empirically determined and will vary with the pathology being treated, the subject being treated, and the efficacy and toxicity of the agent. Similarly, suitable dosage formulations and methods of administering the agents can be readily determined by those of skill in the art. Having described the invention in detail, it will be apparent that modifications and variations are possible without departing the scope of the invention defined in the appended claims. Furthermore, it should be appreciated that all examples in the present disclosure are provided as non-limiting examples.

Salts

The MMP inhibitors utilized in the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, for example, the appropriate acid or base with the compound of any formula set forth herein.

Treatment of Conditions

The important utilities and applications of MMP inhibitors have been described previously in other MMP inhibitor patents, including but not limited to: M. A. Schwartz and H. E. Van Wart, 1995, U.S. Pat. No. 5,455,262, Mercaptosulfide metalloproteinase inhibitors; C. F. Purchase, Jr., B. D. Roth, and A. D. White, 2003, U.S. Pat. No. 6,624,196 B2, Benzene butyric acids and their derivatives as inhibitors of matrix metalloproteinases; Schwartz, M. A., Jin, Y., Hurst, D. R., Sang, Q.-X. Patent Cooperation Treaty (PCT) International Application Pub. No. WO 2005/032541 A1, Substituted Heterocyclic mercaptosulfide Inhibitors; De Crescenzo G., Abbas Z. S., Freskos, J. N., Getman, D. P., Heintz, R. M., Mischke, B. V., McDonald, J. J. 2004, U.S. Pat. No. 6,747,027 B1, Thiol sulfonamide metalloprotease Inhibitors; Levin, J. I., Li, Z., Diamantidis, G., Lovering, F. E., Wang, W., Condon J. S., Lin, Y. I., Skotnicki, J. S., and Park, K., U.S. Patent Application Pub. No. US 2006/0211730 A1, Beta-sulfonamide hydroxamic acid inhibitors of TACE/matrix metalloproteinase. The applications of our metalloproteinase inhibitors described in this invention include the utilities and applications described in the above patents, those detailed below, as well as all other physiological and pathological processes that involve metalloproteinase activities that are not described here.

MMP Inhibitors for Cancer Treatment: MMPs are the major endopeptidases that hydrolyze multiple connective tissue proteins and are likely to be targets for controlling the pathological catabolism of ECM proteins. Applications of our metalloproteinase inhibitors may include, but are not limited to, the control of multiple physiological and pathological processes and conditions described in this document. Prevention and treatments of cancer cell invasion, angiogenesis, and metastasis may be achieved by selective MMP inhibitors (Coussens, L. M., Fingleton, B., Matrisian, L. M. Matrix metalloproteinase inhibitors and cancer: trials and tribulations. *Science*. 2002. 295, 2387-2392; Egeblad, M. and Werb, Z. New functions for the matrix metalloproteinases in cancer progression. *Nature Rev. Cancer* 2002: 2, 163-175; Nemeth, J. A., Yousif, R., Herzog, M., Che, M., Upadhyay, J., Shekarriz, B., Bhagat, S., Mullins, C., Fridman, R., Cher., M. L. Matrix metalloproteinase activity, bone matrix turnover, and tumor cell proliferation in prostate cancer bone metastasis. *J. Natl. Cancer Inst.* 2002: 94, 17-25; Lein, M., Jung, K., Ortel, B., Stephan, C., Rothaug, W., Juchem, R., Johannsen, M., Deger, S., Schnorr, D., Loening, S., Krell, H. W. The new synthetic matrix metalloproteinase inhibitor (Roche 28-2653) reduces tumor growth and prolongs survival in a prostate cancer standard rat model. *Oncogene*. 2002: 21, 2089-2096). Furthermore, MMP inhibitors have shown some efficacy in tumor angiogenesis models (Benelli R., Adatia R., Ensoli B., Stetler-Stevenson W. G., Santi L., Albini A. Inhibition of AIDS-Kaposi's sarcoma cell induced endothelial cell invasion by TIMP-2 and a synthetic peptide from the metalloproteinase propeptide: implications for an anti-angiogenic therapy. *Oncol. Res.*, 1994: 6, 251-257; Brown, P. D., Giavazzi, R. Matrix metalloproteinase inhibition: a review of anti-tumour activity. *Ann. Oncol.* 1995: 6, 967-974; Gatto, C., Rieppi, M., Borsotti, P., Innocenti, S., Ceruti, R., Drudis, T., Scanziani. E., Casazza, A. M., Taraboletti, G., Giavazzi, R. BAY 12-9566, a novel inhibitor of matrix metalloproteinases with antiangiogenic activity. *Clin. Cancer Res.* 1999: 5, 3603-3607; Tosetti, F., Ferrari, N., De Flora, S., Albini, A. Angioprevention: angiogenesis is a common and key target for cancer chemopreventive agents. *FASEB J.* 2002: 16, 2-14). Recent evidence suggests that MT1-MMP may be a critical target for cancer treatment. This MMP is essential for promoting 3-dimensional tumor growth and invasion in vitro and in vivo with aberrant expression suggesting a deleterious role (Notary, K. B., Allen, E. D., Brooks, P. C., Datta, N. S., Long, M. W., Weiss, S. J. Membrane type I matrix metalloproteinase usurps tumor growth control imposed by the three-dimensional extracellular matrix. *Cell,* 2003; 114, 33-45). MT1-MMP may be involved in oncogenesis and energy metabolism in cancer cells (Golubkov, V. S., Chekanov, A. V., Savinov, A. Y., Rozanov, D. V., Golubkova, N. V., Strongin, A. Y. Membrane type-1 matrix metalloproteinase confers aneuploidy and tumorigenicity on mammary epithelial cells. *Cancer Res.* 2006; 66, 10460-10465; Radichev, I. A., Remacle, A. G., Sounni, N. E., Shiryaev, S. A., Rozanov, D. V., Zhu, W., Golubkova, N. V., Postnova, T. I., Golubkov, V. S., Strongin, A. Y. Biochemical evidence of the interactions of membrane type-1 matrix metalloproteinase (MT1-MMP) with adenine nucleotide translocator (ANT): potential implications linking proteolysis with energy metabolism in cancer cells. *Biochem J.* 2009; 420, 37-47).

MMP Inhibitors for Prevention and Treatment of Cardiovascular Diseases: Our MMP inhibitors described in this invention may be used for the prevention and treatment of cardiovascular diseases such as restenosis, cardiac hypertrophy, atherosclerotic plaque rupture, aortic aneurysm, and heart attacks (Loftus, I. M., Thompson, M. M. The role of matrix metalloproteinases in vascular disease. *Vasc. Med.* 2002: 7, 117-133). Cardiovascular diseases are the leading causes of death in Western society, and ECM turnover—mediated by MMPs—is important in many cardiovascular pathologies, such as arterial remodeling, plaque rupture, restenosis, aneurysm formation, and heart failure. Considering the positive outcomes after usage of MMP inhibitors in restenosis and arterial remodeling, MMP inhibitors are likely to be useful in the development of pharmacological approaches to reduce cardiovascular death (Sierevogel, M. J., Pasterkamp, G., De Kleijn, D. P., Strauss, B. H. Matrix metalloproteinases: a therapeutic target in cardiovascular disease. *Curr. Pharm. Des.* 2003: 9, 1033-1040). Enhanced MMP expression has been detected in the atherosclerotic plaque, with activation of these enzymes appearing to contribute to the plaque's vulnerability. In addition, circulating MMP levels are elevated in patients with acute myocardial infarction and unstable angina, and increased expression of these enzymes has also been observed after coronary angioplasty. Altogether, these observations suggest that MMP expression may not be only related to instability of atherosclerotic plaques, but also to the formation of restenotic lesions. The development of therapeutic drugs targeted specifically against MMPs may be useful in the prevention of atherosclerotic lesion development, plaque rupture, and restenosis (Ikeda, U., Shimada, K. Matrix metalloproteinases and coronary artery diseases. *Clin. Cardiol.* 2003: 26, 55-59).

Compared to placebo, a potent and broad spectrum MMP inhibitor, GM6001, significantly inhibited intimal hyperplasia and collagen content, while simultaneously increasing the lumen area in stented arteries without affecting the rates of proliferation. Stenting causes a more vigorous ECM and MMP response than a balloon angioplasty in which each layer of the vessel wall is affected. Selective inhibition by MMP blocks in-stent intimal hyperplasia and offers a novel approach to prevent instent restenosis (Li, C., Cantor, W. J., Nili, N., Robinson, R., Fenkell, L., Tran, Y. L., Whittingham, H. A., Tsui, W., Cheema, A. N., Sparkes, J. D., Pritzker, K., Levy, D. E., Strauss, B. H. Arterial repair after stenting and the effects of GM6001, a matrix metalloproteinase inhibitor. *J. Am. Coll. Cardiol.* 2002: 39, 1852-1858). MMP inhibitors may also be utilized to treat degenerative aortic disease, which is typically associated with a thinning of the medial aortic wall. Increased levels of the proteolytic activities of MMPs have been identified in patients with aortic aneurisms and aortic stenosis (Vine, N., Powell, J. T. Metalloproteinases in degenerative aortic diseases. *Clin. Sci.,* 1991: 81, 233-239). MMPs are also involved in the pathogenesis of cardiovascular disease, including atherosclerosis, dilated cardiomyopathy, and myocardial infarction. Administration of synthetic MMP inhibitors in experimental animal models of these cardiovascular disorders has significantly inhibited the progression of atherosclerotic lesion formation, neointima formation, left ventricular remodeling, pump dysfunction, and infarct healing. As such, MMP inhibitors are potential therapeutic agents for prevention and treatment of heart failure and may also be used for coating stents which will release the inhibitors at given time points to prevent restenosis (Creemers, E. E., Cleutjens, J. P., Smits, J. F., Daemen, M. J. Matrix metalloproteinase inhibition after myocardial infarction: a new approach to prevent heart failure? Circ. Res. 2001: 89, 201-210).

To prevent restenosis after percutaneous transluminal coronary angioplasty (PTCA) and/or stenting of atherosclerotic stenosed arteries, two water-soluble MMPs inhibitors have already been designed and developed by other groups (Masuda, T., Nakayama, Y. Development of a water-soluble matrix metalloproteinase inhibitor as an intra-arterial infusion drug for prevention of restenosis after angioplasty. J. Med. Chem. 2003: 46, 3497-3501). Myocardial infarction (MI) is associated with early MMP activation and ECM degradation. Preserving the original ECM of the infarcted left ventricle by use of early, short-term doxycycline treatment preserves cardiac structure and function. Early MMP inhibition after MI preserves left ventricle structure in addition to aiding global and local (in relation to the scar area) passive function, further supporting the concept that protecting the original ECM shortly after coronary occlusion lessens ventricular remodeling (Villarreal, F. J., Griffin, M., Omens, J., Dillmann, W., Nguyen, J., Covell, J. Early short-term treatment with doxycycline modulates postinfarction left ventricular remodeling. Circulation. 2003: 108, 1487-1492).

Congestive heart failure is a leading cause of death in developed countries with an increasing prevalence worldwide. Typically caused by progressive left ventricular dilation and contractile dysfunction, congestive heart failure can also be attributed to the activity of MMPs. In greater detail, MMPs, which are associated with ventricular dilation, may actually mediate this process. Because these enzymes are extracellular and are pharmacologic targets, MMP inhibition is a novel potential therapy for delaying or preventing heart failure (Lindsey, M., Lee, R. T. MMP inhibition as a potential therapeutic strategy for CHF. Drug News Perspect. 2000: 13, 350-354).

Metalloproteinase inhibitors may be used to treatment many other types of cardiovascular diseases (e.g. MMP-2 and -9 have been shown to play a role in the progression of hemorrhagic stroke), and may even be used to preserve organs during transplantation. A report has described the systemic activation of MMP-2 and -9 in donors with intracerebral hemorrhage and subsequent development of allograft vasculopathy (Yamani, M. H., Starling, R. C., Cook, D. J., Tuzcu, E. M., Abdo, A., Paul, P., Powell, K., Ratliff, N. B., Yu, Y., McCarthy, P. M., Young, J. B. Donor Spontaneous Intracerebral Hemorrhage Is Associated With Systemic Activation of Matrix Metalloproteinase-2 and Matrix Metalloproteinase-9 and Subsequent Development of Coronary Vasculopathy in the Heart Transplant Recipient. Circulation. 2003: 108, 1724-1728). Furthermore, MMP inhibitors may be useful for the transplantation of kidneys and other organs (Marti, H. P. The role of matrix metalloproteinases in the activation of mesangial cells. Transpl. Immunol. 2002: 9, 97-100).

MMP Inhibitors for Prevention and Treatment of Stroke and Other Cerebral Vascular Diseases: MMP inhibitors may be beneficial to the prevention and treatment of stroke (Lapchak, P. A., Araujo, D. M. Reducing bleeding complications after thrombolytic therapy for stroke: clinical potential of metalloproteinase inhibitors and spin trap agents. CNS Drugs. 2001: 15, 819-829). Animal models of stroke usually involve clipping or blocking the mid-cerebral artery in order to permanently or temporarily create occlusion and reperfusion. Alternatively, the injection of blood or bacterial collagenase into the brain can cause a local hemorrhage. In both models, an inflammatory infiltrate is associated with the damaged region. BB-1101 reduces the early phases of blood-brain barrier leakage in an ischemia reperfusion model in the rat and the secondary brain edema which occurs following hemorrhage (Pfefferkorn, T., Rosenberg, G. A. Closure of the blood-brain barrier by matrix metalloproteinase inhibition reduces rtPA-mediated mortality in cerebral ischemia with delayed reperfusion. Stroke. 2003: 34, 2025-2530; Gu, Z., Cui, J., Brown, S., Fridman, R., Mobashery, S., Strongin, A. Y., Lipton, S. A. A highly specific inhibitor of matrix metalloproteinase-9 rescues laminin from proteolysis and neurons from apoptosis in transient focal cerebral ischemia. J. Neurosci. 2005: 25, 6401-6408. Erratum in: J. Neurosci. 2005: 25, 10576; Matrix metalloproteinase-mediated disruption of tight junction proteins in cerebral vessels is reversed by synthetic matrix metalloproteinase inhibitor in focal ischemia in rat. Yang, Y., Estrada, E. Y., Thompson, J. F., Liu, W., Rosenberg, G. A. J. Cereb. Blood. Flow. Metab. 2007; 27, 697-709; Sood, R. R., Taheri, S., Candelario-Jalil, E., Estrada, E. Y., Rosenberg, G. A. Early beneficial effect of matrix metalloproteinase inhibition on blood-brain barrier permeability as measured by magnetic resonance imaging countered by impaired long-term recovery after stroke in rat brain. J. Cereb. Blood Flow Metab. 2008; 28, 431-438; Adibhatla, R. M., Hatcher, J. F. Tissue plasminogen activator (tPA) and matrix metalloproteinases in the pathogenesis of stroke: therapeutic strategies. CNS Neurol. Disord. Drug Targets. 2008; 7, 243-253).

MMP Inhibitors for Prevention of HIV-induced Neurodegeneration: Metalloproteinase inhibitors may prevent human immunodeficiency virus-induced neurodegeneration (Zhang, K., McQuibban, G. A., Silva, C., Butler, G. S., Johnston, J. B., Holden, J., Clark-Lewis, I., Overall, C. M., Power, C. HIV-induced metalloproteinase processing of the chemokine stromal cell derived factor-1 causes neurodegeneration. Nat. Neurosci. 2003: 6, 1064-1071). These inhibitors may be used to treat spinal cord injury and promote wound healing (Goussev, S., Hsu, J. Y., Lin, Y., Tjoa, T., Maida, N., Werb, Z., Noble-Haeusslein, L. J. Differential temporal expression of matrix metalloproteinases after spinal cord injury: relationship to revascularization and wound healing. J. Neurosurg. 2003: 99(2 Suppl), 188-197). Gelatinases, belonging to the matrix metalloproteases, contribute to tissue destruction in inflammatory demyelinating disorders of the central nervous system such as multiple sclerosis. Gijbels et al. used experimental autoimmune encephalomyelitis (EAE) as an animal model to evaluate the effect of a hydroxamate MMP inhibitor (GM6001) on inflammatory demyelination. When administered daily either from the time of disease induction or from the onset of clinical signs, GM6001 suppressed the development or reversed clinical signs of EAE in a dose-dependent way. This effect appears to be mediated mainly through restoration of the damaged blood-brain barrier in the inflammatory phase of the disease (Gijbels, K., Galardy, R. E., Steinman, L. Reversal of experimental autoimmune encephalomyelitis with a hydroxamate inhibitor of matrix metalloproteases. J. Clin. Invest. 1994: 94, 2177-2182). Overall, MMP inhibitors may have multiple functions against multiple diseases (Supuran, C. T., Casini, A., and Scozzafava, A. Protease inhibitors of the sulfonamide type: anticancer, antiinflammatory, and antiviral agents. *Med. Res. Rev.* 2003: 23, 535-558).

MMP Inhibitors for the Prevention and Treatment of Neuroinflammation: Neuroinflammation, which occurs in response to brain injury or autoimmune disorders, has been shown to cause the destruction of healthy tissues. Neuroinflammatory mechanisms are involved in many acute and chronic neurodegenerative disorders, including stroke, multiple sclerosis, head trauma, and Alzheimer's disease (McGeer, E. G., McGeer, P. L. Neurodegeneration and the immune system. In: Calne D. B., ed. *Neurodegenerative Diseases*, W. B. Saunders, 1994: pp 277-300). Other diseases that may implicate neuroinflammatory mechanisms include amyotrophic lateral sclerosis (Leigh, P. N. Pathogenic mechanisms in amyotrophic lateral sclerosis and other motor neuron disorders. In: Calne D. B., ed., *Neurodegenerative Diseases*, W. B. Saunders, 1994: pp 473-488), cerebral amyloid angiopathy (Mandybur, T. I., Balko, G., Cerebral amyloid angiopathy with granulomatous angiitis ameliorated by steroid-cytoxan treatment, *Clin. Neuropharm.* 1992: 15, 241-247), AIDS (Gendelman, H. E., Tardieu, M., Macrophages/microglia and the pathophysiology of CNS injuries in AIDS. *J. Leukocyte Biol.*, 1994: 56, 387-388), Parkinson's disease, Huntington's disease, prion diseases, and certain disorders involving the peripheral nervous system, such as myasthenia gravis and Duchenne's muscular dystrophy, as well as Alzheimer's disease (Aisen P. S., Anti-inflammatory therapy for Alzheimer's disease. *Dementia.* 1995: 9, 173-82). Metalloproteinase inhibitors may modulate these processes and slow the disease progression.

MMP Inhibitors for Treatment of Respiratory and Lung Problems: Airway inflammation and remodeling are key features of asthma, and MMPs, along with their inhibitors, are thought to contribute to the pathogenesis via contributions to the function and migration of inflammatory cells in addition to matrix deposition and degradation (Kelly, E. A., Jarjour, N. N. Role of matrix metalloproteinases in asthma. *Curr. Opin. Pulm. Med.* 2003: 9, 28-33; Chiappara, G., Gagliardo, R., Siena, A., Bonsignore, M. R., Bousquet, J., Bonsignore, G., Vignola, A. M. Airway remodelling in the pathogenesis of asthma. *Curr. Opin. Allergy Clin. Immunol.* 2001: 1, 85-93). Increasing evidence has indicated that MMPs, especially MMP-9, are involved in the pathogenesis of asthma, chronic obstructive pulmonary disease, and multiple sclerosis (Demedts, I. K., Brusselle, G. G., Bracke, K. R., Vermaelen, K. Y., Pauwels, R. A. Matrix metalloproteinases in asthma and COPD. *Curr. Opin. Pharmacol.* 2005: 5, 257-263; M. E. Muroski, M. D. Roycik, R. G. Newcomer, P. E. Van den Steen, G. Opdenakker, H. R. Monroe, Z. J. Sahab, and Q.-X. Sang. Matrix Metalloproteinase-9/Gelatinase B is a Putative Therapeutic Target of Chronic Obstructive Pulmonary Disease and Multiple Sclerosis. *Curr. Pharma. Biotechnol.*, 2008: 9, 34-46).

MMP Inhibitors for the Treatment of Arthritis: Our metalloproteinase inhibitors may also be useful for the treatment of different types of arthritis, as inhibition of MMPs has been a useful treatment in animal models of osteoarthritis (Janusz, M. J., Hookfin, E. B., Heitmeyer, S. A., Woessner, J. F., Freemont, A. J., Hoyland, J. A., Brown, K. K., Hsieh, L. C., Almstead, N. G., De, B., Natchus, M. G., Pikul, S., Taiwo, Y. O. Moderation of iodoacetate-induced experimental osteoarthritis in rats by matrix metalloproteinase inhibitors. *Osteoarthr. Cartil.* 2001:9, 751-760; Vincenti, M. P., Clark, I. M., Brinckerhoff, C. E. Using inhibitors of metalloproteinases to treat arthritis. Easier said than done? *Arthritis. Rheum.* 1994: 37, 1115-1126). Increased expression—when compared to controls—of stromelysin and collagenase in synovial fluids from osteo- and rheumatoid arthritis patients has been reported (Walakovits, L. A., Moore, V. L., Bhardwaj, N., Gallick, G. S., Lark, M. W. Detection of stromelysin and collagenase in synovial fluid from patients with rheumatoid arthritis and post-traumatic knee injury. *Arthritis Rheum.* 1992: 35, 35-42). Rheumatoid arthritis and osteoarthritis are chronic diseases that result in cartilage degradation and loss of joint function. As such, currently available drugs are predominantly directed towards the control of pain and/or the inflammation associated with joint synovitis and do little to mitigate joint destruction. It will be important to have MMP inhibitors that prevent the structural damage caused by the breakdown of bone and cartilage (Elliott, S., Cawston, T. The clinical potential of matrix metalloproteinase inhibitors in the rheumatic disorders. *Drugs Aging.* 2001: 18, 87-99; Bigg, H. F., Rowan, A. D. The inhibition of metalloproteinases as a therapeutic target in rheumatoid arthritis and osteoarthritis. *Curr. Opin. Pharmacol.* 2001: 1, 314-320).

MMP Inhibitors for the Treatment of Periodontal Diseases: Human gingival fibroblast collagenase and stromelysin levels are correlated to the severity of gum disease, and MMP inhibitors have been used to treat periodontal diseases (Overall, C. M., Wiebkin, O. W., Thonard, J. C. Demonstrations of tissue collagenase activity in vivo and its relationship to inflammation severity in human gingival. *J. Periodontal Res.* 1987: 22, 81-88; Ramamurthy, N. S., Rifkin, B. R., Greenwald, R. A., Xu, J. W., Liu, Y., Turner, G., Golub, L. M., Vernillo, A. T. Inhibition of matrix metalloproteinase-mediated periodontal bone loss in rats: a comparison of 6 chemically modified tetracyclines. *J. Periodontol.* 2002: 73, 726-734; Ciancio, S. G. Systemic medications: clinical significance in periodontics. *J. Clin. Periodontol.* 2002: Suppl. 2, 17-21).

MMP Inhibitors for the Treatment of Eye Problems: Hydrolysis of ECM proteins was reported in corneal ulceration following alkali burns and thiol-containing peptide inhibitors blocked the collagenases activity in animal models (Brown, S. I., Weller, C. A., Wasserman, H. E. Collagenolytic activity of alkali burned corneas. *Arch. Ophthalmol.*, 1969; 81, 370-373; Burns, F. R., Stack, M. S., Gray, R. D., Paterson, C. A. *Invest. Ophthalmol.* 1989: 30, 1569-1575). Thus, MMP inhibitors can be used to treat corneal ulceration and perhaps even control the progression of macular degeneration (Musarella, M. A. Molecular genetics of macular degeneration. *Doc. Ophthalmol.* 2001: 102, 165-177).

MMP Inhibitors for Wound Repair: MMP inhibitors may modulate wound healing process (Armstrong, D. G., Jude, E. B. The role of matrix metalloproteinases in wound healing. *J. Am. Podiatr. Med. Assoc.* 2002: 92, 12-18). Wound healing is a complex physiological process with many intricate biochemical reactions (Xue, M., Le, N. T., Jackson, C. J. Targeting matrix metalloproteinases to improve cutaneous wound healing. *Expert Opin. Ther. Targets.* 2006: 10, 143-155). Following tissue injury, a complex biomolecular mediated repair process starts the restoration of structure and function of the tissue. Skin wound repair starts with platelet aggregation, formation of fibrin clot, inflammatory response, and then, granulation tissue formation, new blood vessel formation, re-epithelialization, and finally, matrix formation and tissue remodeling. Cell migration, angiogenesis, degradation of the extracellular matrix (ECM), and remodeling of newly formed granulation tissue requires controlled degradation of ECM. Disturbance in the balance between ECM production and degradation leads to formation of chronic ulcers with excessive ECM degradation. As a family of zinc proteinases, MMPs can degrade numerous ECM components, including endothelial tight-junction proteins which compromise vessel integrity (Sang, Q. X., Jin, Y., Newcomer, R. G., Monroe, S. C., Fang, X., Hurst, D. R., Lee, S., Cao, Q. Schwartz, M. A. Matrix Metalloproteinase Inhibitors as Prospective Agents for the Prevention and Treatment of Cardiovascular and Neoplastic Diseases. *Curr. Top. Med. Chem.* 2006; 6, 289-316; Hu, J., Van den Steen, P. E., Sang, Q. X., Opdenakker, G. Matrix metalloproteinase inhibitors as therapy for inflammatory and vascular diseases. *Nat. Rev. Drug Discov.* 2007; 6, 480-498). Excessive MMP activity contributes to the development of chronic wounds (Xue, M., Le, N. T., Jackson, C. J. Targeting matrix metalloproteinases to improve cutaneous wound healing. *Expert Opin. Ther. Targets.* 2006: 10, 143-155). As such, the selective control of the activity of this family of enzymes by the selective MMP inhibitors may prove to be a valuable therapeutic approach to promote healing of acute wounds and chronic ulcers. Accordingly, therapeutic interventions that target MMPs, particularly with the goal of controlling local MMP activity offer promise in the treatment of open wounds.

MMP Inhibitors for Stem Cell Differentiation: MMPs play important roles in development, morphogenesis, tissue repair, and regeneration processes. MMP activity is associated with mesenchymal stem cell phenotype changes caused by microenvironmental factors such as mechanical stimulus (Kasper, G., Glaeser, J. D., Geissler, S., Ode, A., Tuischer, J., Matziolis, G., Perka, C., and Duda, G. N. Matrix metalloproteinase activity is an essential link between mechanical stimulus and mesenchymal stem cell behavior. *Stem Cells.* 2007, 25, 1985-1994). Regulation of MMP activity is also crucial for mesenchymal stem cell migration, invasion, and possibly differentiation (Neth, P., Ciccarella, M., Egea, V., Hoelters, J., Jochum, M., and Ries, C. Wnt signaling regulates the invasion capacity of human mesenchymal stem cells. *Stem Cells.* 2006, 24, 1892-1903; Ries, C.; Egea, V., Karow, M., Kolb, H., Jochum, M., and Neth, P. MMP-2, MT1-MMP, and TIMP-2 are essential for the invasive capacity of human mesenchymal stem cells: differential regulation by inflammatory cytokines. *Blood.* 2007, 109, 4053-4063). One may envision that synthetic MMP inhibitors, especially the highly selective inhibitors targeting specific members of the MMP family, may become powerful tools to control MMP activity and regulate the differentiation pathways of stem cells.

MMP Inhibitors for Skin Protection: Metalloproteinase inhibitors may be used in sun screens and skin lotions to prevent ultraviolet (UV) irradiation damage to the skin and prevent skin aging. UV irradiation acts as a broad activator of cell surface growth factor and cytokine receptors. UV-enhanced matrix degradation is accompanied with decreased collagen production. Several alterations to skin connective tissue that occur during aging are mediated by mechanisms that are similar to those that occur in response to UV irradiation. Thus, skin aging is associated with increased activator protein 1 activity, increased MMP expression, impaired transforming growth factor beta signaling, enhanced collagen degradation, and decreased collagen synthesis. Knowledge gained from examining molecular responses of human skin to UV irradiation provides a framework for understanding mechanisms involved in skin aging and may help in the development of new clinical strategies to impede chronological and UV-induced skin aging (Rittie, L, Fisher, G. J. UV-light-induced signal cascades and skin aging. *Ageing Res. Rev.* 2002: 1, 705-720).

Other Important Utilities and Applications of MMP Inhibitors: Many potential therapeutic applications of MMP inhibitors have been summarized previously (Whittaker, M., Floyd, C. D., Brown, P., Gearing, A. J. H. Design and Therapeutic Application of Matrix Metalloproteinase Inhibitors. *Chem. Rev.* 1999: 99, 2735-2776). MMP inhibitors block the activity of both MMPs and adamalysins (ADAMs) and have the potential utility in the prevention and treatment of multiple diseases, including, but not limited to, cancer, inflammation, arthritis, restensosis, aortic aneurysm, glomerulonephritis, Guillain Barré syndrome, Bacterial Meningitis, Uveoretinitis, Graft-versus-host disease, noninsulin-dependent diabetes mellitus, and numerous others. Tissue destruction and remodeling, angiogenesis, and the migration of leukocytes through connective tissue observed during various inflammatory diseases, mirror similar MMP-driven processes in cancer and as such, there is now a considerable body of evidence that inflammatory leukocytes in culture and inflamed tissues in vivo express multiple MMPs. The inhibition of the TNF-α converting enzyme (TACE or ADAM-17) also confers an added anti-inflammatory potential to some MMP inhibitors, such as BB-1101, and have been shown to be effective in a number of animal models of inflammatory disease. Glomerulonephritis is a nephritic syndrome which results in destruction and fibrosis of the kidneys. BB-1101 given prior to disease induction significantly reduced the inflammatory response and damage.

As described in the review paper (Whittaker, M., Floyd, C. D., Brown, P., Gearing, A. J. H. Design and Therapeutic Application of Matrix Metalloproteinase Inhibitors. *Chem. Rev.* 1999: 99, 2735-2776), in experimental autoimmune encephalomyelitis (EAE), a model of multiple sclerosis, rodents are immunized with myelin or one of its protein components in adjuvant, resulting in an autoimmune inflammation of the brain and spinal cord. Adoptive transfer of activated myelin-specific T cells can also result in a similar disease with recurrent episodes of paralysis. A multiple sclerotic-like lesion can also be induced in the brain by the generation of a delayed-type hypersensitivity response. Furthermore, Guillain Barré syndrome (GBS) is an acute inflammatory paralytic disease of the peripheral nervous system in which leukocytes infiltrate nerves causing demyelination and oedema. An animal model of GBS, experimental autoimmune neuritis (EAN), is induced in rodents by immunization with peripheral nerve myelin. This results in a T cell-dependent inflammation in peripheral nerves leading to paralysis. Inhibitor BB-1101 given from the initiation of EAN prevented the development of symptoms and reduced inflammation, demyelination, and weight loss. When given from the onset of symptoms, the compound significantly reduced disease severity.

As regard to the treatment of bacterial meningitis, rodents can develop bacterial meningitis following infection with bacteria. Batimastat was effective in reducing intracranial pressure and blood-brain barrier breakdown in a model of meningococcal meningitis. In addition, uveoretinitis is an autoimmune inflammatory disease of the eye. Rodent models of uveitis involve immunization with retinal antigens in adjuvant. Treatment with inhibitor BB-1101 was shown to reduce retinal damage in experimental autoimmune uveitis (Whittaker, M., Floyd, C. D., Brown, P., Gearing, A. J. H. Design and Therapeutic Application of Matrix Metalloproteinase Inhibitors. *Chem. Rev.* 1999: 99, 2735-2776). Moreover, graft-versus-host disease (GVHD) can be a major complication following allogeneic bone marrow transplantation. In a mouse model of lethal acute GVHD administration of inhibitor KB-R7785 reduced mortality. This effect was attributed to the inhibition of both tumor necrosis factor-alpha (TNF-α) and Fas ligand release by KB-R7785. TNF-α is a key mediator of insulin resistance in noninsulin-dependent diabetes mellitus. In a mouse model of insulin resistance, administration of KB-R7785 resulted in a significant decrease in both plasma glucose and insulin levels. It is suggested that KB-R7785 exerts its anti-diabetic effect by ameliorating insulin sensitivity through the inhibition of TNF-α production. Metalloproteinase inhibitors may have anti-bacterial activities (Scozzafava, A., Supuran, C. T. Protease inhibitors—part 5. Alkyl/arylsulfonyl- and arylsulfonylureido-/arylureido-glycine hydroxamate inhibitors of *Clostridium histolyticum* collagenase. *Eur. J. Med. Chem.* 2000: 35, 299-307).

MMPs and metalloproteinases play extremely important roles in reproduction, the control of fertility, and reproductive capabilities (e.g. contraception/birth control). Fertilization, the menstrual cycle, embryo implantation, uterine bleeding, and many other normal and pathological reproductive processes are controlled by metalloproteinases and their inhibitors (Bischof, P., Campana, A. Molecular mediators of implantation. *Baillieres Best Pract. Res. Clin. Obstet. Gynaecol.* 2000: 14, 801-814; Dong, J. C., Dong, H., Campana, A., Bischof, P. Matrix metalloproteinases and their specific tissue inhibitors in menstruation. *Reproduction.* 2002: 123, 621-631). Thus, in addition to controlling cancers, cardiovascular diseases, inflammation, pain, and arthritis, numerous other conditions may be prevented and treated by these inhibitors. Specifically, these may include: (1) corneal ulceration; (2) diabetic retinopathy and other diabetic complications; (3) wound healing; (4) osteoporosis; (5) kidney diseases; (6) neurodegenerative diseases including, Alzheimer's disease; (7) spinal cord injury and head trauma; (8) AIDS; (9) Parkinson's disease; (10) Huntington's disease; (11) prion diseases; (12) regulation of blister formation; (13) regulation of allergy; (14) modulation of bone remodeling and regeneration; (15) control of asthma, or other inflammatory or autoimmune disorders relying on tissue invasion by different types of cells including white blood cells, and many types of diseases involved in the immune system in the body (Whittaker, M., Floyd, C. D., Brown, P., and Gearing, A. J. H. Design and Therapeutic Application of Matrix Metalloproteinase Inhibitors. *Chem. Rev.* 1999: 99, 2735-2776; Sternlicht, M. D., Werb Z. How matrix metalloproteinases regulate cell behavior. *Annu Rev Cell Dev Biol.* 2001: 17, 463-516). MMP inhibitors may also be used for the treatment of Crohn's disease and irritable bowel syndrome (Mäkitalo, L., Sipponen, T., Kärkkäinen, P., Kolho, K. L., Saarialho-Kere, U. Changes in matrix metalloproteinase (MMP) and tissue inhibitors of metalloproteinases (TIMP) expression profile in Crohn's disease after immunosuppressive treatment correlate with histological score and calprotectin values. *Int. J. Colorectal Dis.* 2009 Aug. 4. [Epub ahead of print]).

Metalloproteinase inhibitors may be used for industrial manufacturing of extracellular matrix/collagen products, cosmetics, beauty, and skin protection and medication products. These inhibitors can be used for the prevention and treatments of conditions in human beings and in animals, such as dogs, horses, cats, pigs, birds, sheep, cattle, and in other organisms such as plants and bacteria.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

N-Boc-3-pyrroline oxide. To a stirred solution of N-Boc-3-pyrroline (1.69 g, 10 mmol) in $CH_2Cl_2$ (20 mL) was added m-chloroperbenzoic acid (MCPBA) (~85%, 5.2 g) in $CH_2Cl_2$ (20 mL) dropwise, and stirring was continued at room temperature overnight. The solution was extracted with saturated aqueous $NaHCO_3$, saturated aqueous $Na_2SO_3$ and saturated aqueous $NaHCO_3$ successively. The organic layer was dried over $Na_2SO_4$ and filtered. The solvent was evaporated and the residue was purified by flash chromatography (20% ethyl acetate in hexane) to give the product as an oil (1.54 g, 82%): $^1H$ NMR (300 MHz, $CDCl_3$) δ 3.77 (dd, J=22, 13 Hz, 2H), 3.66 (m, 2H), 3.31 (dd, J=13, 3 Hz, 2H), 1.44 (s, 9H).

(±)-N-Boc-trans-3-azido-4-hydroxypyrrolidine. A mixture of N-Boc-3-pyrroline oxide (0.925 g, 5.0 mmol), $NaN_3$ (0.65 g, 10 mmol), and $NH_4Cl$ (5.0 mmol) in MeOH—$H_2O$ (6:1, 16 mL) was stirred at 65° C. overnight. The reaction mixture was concentrated under reduced pressure and the residue was extracted thoroughly with ethyl acetate. The combined ethyl acetate extract was washed with water and sat. brine, dried over anhydrous $Na_2SO_4$, and evaporated. The crude azidoalcohol was purified by recrystallization from ether-hexane: mp 34-36° C.; $^1H$ NMR (300 MHz, $CD_3OD$) δ 4.16 (m, 1H), 3.95 (m, 1H), 3.62 (m, 1H), 3.51 (m, 1H), 3.35 (m, 2H), 1.47 (s, 9H).

(±)-N-Boc-trans-3-(4-phenoxybenzenesulfonamido)-4-hydroxypyrrolidine. To a stirred solution of the azidoalcohol (1.02 g, 4.45 mmol) in THF—$H_2O$ (10:1, 10 mL) was added $Ph_3P$ (1.28 g, 4.88 mmol), and the mixture was stirred at room temperature for 2 hours and at 65° C. for 2 hours. The solution was cooled with stirring to 0° C., triethylamine (0.74 mL, 5.34 mmol) was added, then a solution of 4-phenoxybenzenesulfonyl chloride (1.04 g, 4.45 mmol) in THF (5 mL) was added dropwise. The reaction mixture was warmed to room temperature and was stirred for 3 hours. The mixture was concentrated under reduced pressure, ethyl acetate was added to the residue and the organic layer was washed with 10% citric acid and saturated aqueous $NaHCO_3$, then it was dried over $Na_2SO_4$ and evaporated. The residue was purified by flash chromatography (50% ethyl acetate in hexane) to give the product as a solid (1.52 g, 79%): mp 98-99° C.; $^1H$ NMR (300 MHz, $CD_3OD$) δ 7.85 (d, J=8, 2H), 7.45 (m, 2H), 7.24 (t, J=7, 1H), 7.10 (m, 4H), 4.09 (m, 1H), 3.95 (m, 1H), 3.70 (m, 2H), 3.40 (m, 2H), 1.42 (s, 9H); MS, ESI m/e 434.1 (M+); HRMS (ESI) calculated for $C_{21}H_{26}N_2O_6SNa^+$ 457.1391. found 457.1391.

(±)-N-Boc-trans-3-(4-phenoxybenzenesulfonamido)-4-tertbutylmercaptopyrrolidine. To a stirred solution of $Ph_3P$ (0.88 g, 3.35 mmol) and (±)-N-Boc-trans-3-(4-phenoxybenzenesulfonamido)-4-hydroxypyrrolidine (1.316 g, 3.04 mmol) in THF (20 mL) at 0° C. was added diethyl azodicarboxylate (DEAD) (0.58 mL, 3.33 mmol) dropwise. The reaction mixture was stirred at room temperature overnight, then it was evaporated under reduced pressure. The residue was purified by flash chromatography (30% ethyl acetate in hexane) to give the N-(4-phenoxybenzenesulfonyl)aziridine as a solid (1.23 g, 98%): mp 136-138° C.; $^1H$ NMR (300 MHz, $CDCl_3$) δ 7.88 (m, 2H), 7.43 (m, 2H), 7.22 (m, 1H), 7.10 (m, 4H), 3.72 (m, 2H), 3.59 (m, 1H), 3.47 (m, 1H), 3.38 (m, 2H), 1.42 (s, 9H); MS, ESI m/e 416.1 (M+); HRMS (ESI) calcd for $C_{21}H_{24}N_2O_5SNa+$ 439.1290. found 439.1290.

To a stirred solution of the aziridine (416.5 mg, 1.0 mmol) and tert-butyl mercaptan (0.15 mL, 1.2 mmol) in anhydrous methanol (5 mL) at 0° C. was added t-BuOK (0.2 mmol). The mixture was stirred at room temperature for 4 hr, then it was evaporated under reduced pressure. Ethyl acetate was added to the residue and the solution was extracted with water and with sat. brine, then it was dried over $Na_2SO_4$ and evaporated. The residue was purified by flash chromatography (20% ethyl acetate in hexane) to give the product as a solid (506.4 mg, 98%): mp 85-86° C.; $^1$H NMR (300 MHz, $CD_3OD$) δ 7.85 (d, J=7, 2H), 7.45 (t, J=7, 2H), 7.25 (t, J=7, 1H), 7.09 (d, J=7, 4H), 3.81 (m, 2H), 3.58 (m, 1H) 3.47 (m, 1H), 3.22 (m, 1H), 3.09 (m, 1H), 1.45 (s, 9H), 1.29 (s, 9H); MS, ESI m/e 506.2 (M+); HRMS (ESI) calcd for $C_{25}H_{34}N_2O_5S_2Na+$ 529.1796. found 529.1795.

Example 1

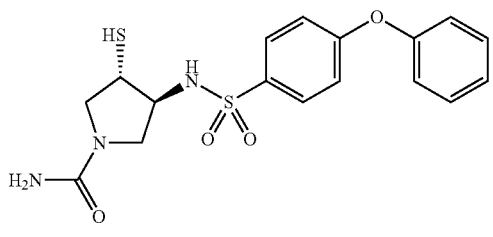

YHJ-6-286

YHJ-6-286: (±)-N-Carbamoyl-trans-3-(4-phenoxybenzenesulfonamido)-4-mercaptopyrrolidine. To a stirred solution of 1.5 M HCl in ethyl acetate (5 mL) was added (±)-N-Boc-trans-3-(4-phenoxybenzenesulfonamido)-4-tert-butylmercaptopyrrolidine (155 mg, 0.3 mmol) and stirring was continued at room temperature until no starting material was detected by TLC (50% ethyl acetate in hexane). The solvent was evaporated under reduced pressure and the residue was dissolved in $CH_2Cl_2$. The solution was cooled to 0° C. and triethylamine (46 µl, 33 mmol) and N-trimethylsilyl isocyanate (TMSNCO) (100 µL, 0.74 mmol) were added successively. The solution was stirred at room temperature overnight. The reaction mixture was extracted with water and sat. brine, and was dried over $Na_2SO_4$ and filtered. The solvent was evaporated and the residue was purified by flash chromatography (5% MeOH in ethyl acetate) to give (±)-N-carbamoyl-trans-3-(4-phenoxybenzenesulfonamido)-4-tert-butylmercaptopyrrolidine (130 mg, 96%): mp 132-133° C.; $^1$H NMR (300 MHz, $CD_3OD$) δ 7.85 (d, J=9, 2H), 7.44 (t, J=8, 2H), 7.24 (t, J=8, 1H), 7.10 (m, 2H), 7.09 (d, J=9, 2H), 3.86 (m, 1H), 3.59 (m, 2H) 3.27 (m, 2H), 3.15 (m, 1H), 1.29 (s, 9H); MS (ESI) m/e 449.2 (M+); HRMS (ESI) calcd for $C_{21}H_{27}N_3O_4S_2Na+$ 472.1322. found 472.1326.

To a solution of (±)-N-carbamoyl-trans-3-(4-phenoxybenzenesulfonamido)-4-tert-butylmercaptopyrrolidine (110 mg, 0.245 mmol) in AcOH (1 mL) was added 2-nitrobenzenesulfenyl chloride (51 mg, 0.269 mmol) and the mixture was stirred at room temperature for 2 hr. The AcOH was evaporated under vacuum, and to the residue was added THF (4 mL), 1 N NaOH (0.3 mL) and tris(2-carboxyethyl)phosphine (TCEP) (77 mg, 0.269 mmol) with stirring under argon. Stirring under argon was continued for 3 hr at room temperature, then the mixture was concentrated under vacuum. To the residue was added ethyl acetate and it was dried over $Na_2SO_4$ and filtered. The solvent was evaporated and the residue was purified by flash chromatography (5% MeOH in ethyl acetate) to give the mercaptan as a white solid (89 mg, 96%) (YHJ-6-286): mp 170-171° C.; $^1$H NMR (300 MHz, $CD_3OD$) δ 7.87 (m, 2H), 7.44 (m, 2H), 7.24 (m, 1H), 7.10 (m, 4H), 3.78 (m, 1H), 3.68 (m, 1H), 3.59 (m, 1H) 3.20 (m, 2H), 3.08 (m, 1H); MS (ESI) m/e 393.1 (M+); HRMS (ESI) calcd for $C_{17}H_{19}N_3O_4S_2Na+$ 416.0701. found 416.0699.

Example 2

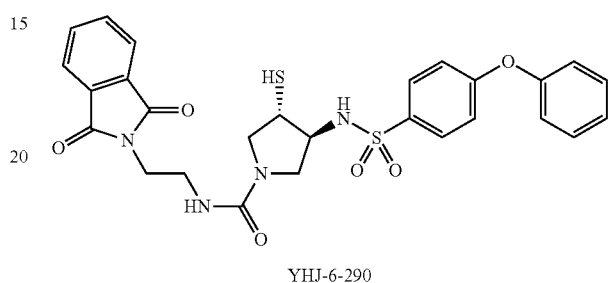

YHJ-6-290

YHJ-6-290: (±)-N-(2-Phthalimidoethylaminocarbonyl)-trans-3-(4-phenoxybenzenesulfonamido)-4-mercaptopyrrolidine. To a stirred solution of 1.5 M HCl in ethyl acetate (3 mL) was added (±)-N-Boc-trans-3-(4-phenoxybenzenesulfonamido)-4-tertbutylmercaptopyrrolidine (77.5 mg, 0.15 mmol) and stirring was continued at room temperature until no starting material was detected by TLC (50% ethyl acetate in hexane). The solvent was evaporated under reduced pressure and the residue was dissolved in $CH_2Cl_2$ (3 mL). The solution was cooled to −10° C. and diisopropylethylamine (63 µL, 0.36 mmol) and triphosgene (14.9 mg, 0.05 mmol) in $CH_2Cl_2$ (3 mL) were added. The mixture was stirred at −10° C. for 20 min, then diisopropylethylamine (63 µL, 0.36 mmol) and 2-phthalimidoethylamine hydrochloride (34 mg, 0.15 mmol) were added successively. The solution was warmed to room temperature and was stirred for 4 hr. The reaction mixture was extracted with water, dried over $Na_2SO_4$, and evaporated under reduced pressure. The residue was purified by flash chromatography (5% MeOH in ethyl acetate) to give (±)-N-(2-phthalimidoethylaminocarbonyl)-trans-3-(4-phenoxybenzenesulfonamido)-4-tert-butylmercaptopyrrolidine as a white solid (79 mg, 84%): mp 105-106° C.; $^1$H NMR (300 MHz, $CDCl_3$) δ 7.92 (m, 2H), 7.85 (m, 2H), 7.72 (m, 2H), 7.42 (m, 2H), 7.24 (m, 1H), 7.10 (m, 4H), 5.62 (d, J=9, 1H), 4.62 (m, 1H), 3.98-3.70 (m, 3H), 3.62 (m, 1H), 3.48 (m, 3H), 3.24 (m, 2H) 3.14 (m, 1H), 1.32 (s, 9H);); MS (ESI) m/e 622.2 (M+); HRMS (ESI) calcd for $C_{31}H_{34}N_4O_6S_2Na+$ 645.1812. found 645.1814.

To a solution of (±)-N-(2-phthalimidoethylaminocarbonyl)-trans-3-(4-phenoxybenzenesulfonamido)-4-tert-butylmercaptopyrrolidine (62.3 mg, 0.10 mmol) in AcOH (1 mL) was added 2-nitrobenzenesulfenyl chloride (21 mg, 0.11 mmol) and the mixture was stirred at room temperature for 2 hr. The AcOH was evaporated under vacuum, and to the residue was added THF (2 mL), 1 N NaOH (0.2 mL) and TCEP (34 mg, 0.12 mmol). The mixture was stirred at room temperature under argon for 3 hr, then it was condensed under vacuum. To the residue was added ethyl acetate and it was dried over $Na_2SO_4$ and filtered. The solvent was evaporated and the residue was purified by flash chromatography (ethyl acetate) to give the mercaptan as a white solid (48 mg, 87%)

(YHJ-6-290): mp 140-141.5° C.; $^1$H NMR (300 MHz, CDCl$_3$) δ 7.93-7.80 (m, 4H), 7.73 (m, 2H), 7.41 (m, 2H), 7.23 (t, J=8, 1H), 7.15-7.00 (m, 4H), 5.73 (br, 1H), 4.73 (m, 1H), 3.87 (m, 2H), 3.71 (m, 2H), 3.55 (m, 1H), 3.47 (m, 2H), 3.37 (m, 1H), 3.24 (m, 1H), 3.13 (m, 1H), 1.74 (d, J=7, 1H); MS (ESI) m/e 566.2 (M+); HRMS (ESI) calcd for C$_{27}$H$_{26}$N$_4$O$_6$S$_2$Na+ 589.1191. found 589.1190.

Example 3

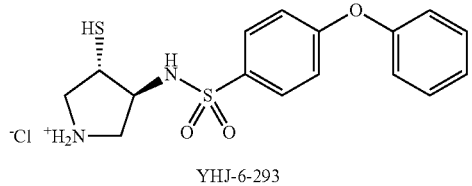

YHJ-6-293

YHJ-6-293: (±)-trans-3-(4-Phenoxybenzenesulfonamido)-4-mercaptopyrrolidine Hydrochloride. To a solution of (±)-N-Boc-trans-3-(4-phenoxybenzenesulfonamido)-4-tertbutylmercaptopyrrolidine (117 mg, 0.226 mmol) in AcOH (1 mL) was added 2-nitrobenzenesulfenyl chloride (46.0 mg, 0.243 mmol) and the mixture was stirred at room temperature for 2 h. The AcOH was evaporated under vacuum, and to the residue was added THF (4 mL), 1N NaOH (0.25 mL) and TCEP (67 mg, 0.234 mmol). The mixture was stirred at room temperature under argon for 3 hr, then it was condensed under vacuum. To the residue was added ethyl acetate and it was dried over Na$_2$SO$_4$ and filtered. The solvent was evaporated and the residue was purified by flash chromatography (ethyl acetate) to give(±)-N-Boc-trans-3-(4-phenoxybenzenesulfonamido)-4-mercaptopyrrolidine as a white solid (82 mg, 81%): 78-79° C.; $^1$H NMR (300 MHz, CD$_3$OD) δ 7.88 (m, 2H), 7.45 (m, 2H), 7.25 (t, J=7, 1H), 7.10 (m, 4H), 3.74 (m, 1H), 3.55 (m, 2H), 3.17 (m, 2H), 3.00 (m, 1H), 1.44 (s, 9H); MS (ESI) m/e 450.2 (M+); HRMS (ESI) calcd for C$_{21}$H$_{26}$N$_2$O$_5$S$_2$Na+ 473.1172. found 473.1170.

To a solution of 2.5 M HCl in AcOH (1 mL) was added (±)-N-Boc-trans-3-(4-phenoxybenzenesulfonamido)-4-mercaptopyrrolidine (45 mg, 0.10 mmol) and the mixture was stirred at room temperature for 3 hr. Lyophylization of the solution gave the product as a white powder (38.7 mg, 100%) (YHJ-6-293): $^1$H NMR (300 MHz, CD$_3$OD) δ 7.87 (d, J=12, 2H), 7.44 (m, 2H), 7.24 (t, J=7, 1H), 7.12 (m, 4H), 3.72 (m, 1H), 3.62 (m, 2H), 3.37 (m, 1H), 3.19 (m, 2H); MS (ESI) m/e 351.1 (MH+); HRMS (ESI) calcd for C$_{16}$H-19N$_2$O$_3$S$_2$+ 351.0837. found 351.0837.

Example 4

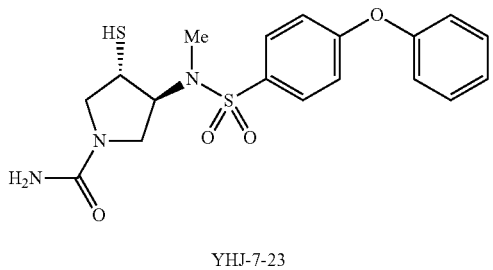 [SMILES: CN([C@H]1CN(C(N)=O)C[C@@H]1S)S(=O)(=O)c1ccc(Oc2ccccc2)cc1]

YHJ-7-23

YHJ-7-23: (±)-N-Carbamoyl-trans-3-(N-methyl-4-phenoxybenzenesulfonamido)-4-mercaptopyrrolidine. To a solution of (±)-N-Boc-trans-3-(4-phenoxybenzenesulfonamido)-4-tert-butylmercaptopyrrolidine (236 mg, 0.466 mmol) in DMF (2 mL) at 0° C. was added tBuOK (0.69 mmol). The mixture was stirred at 0° C. for 10 min, then MeI (0.69 mmol) was added. The solution was stirred at 0° C. until TLC analysis showed no starting material remained. Ethyl acetate (20 mL) was added and the solution was extracted with water, then was dried over Na$_2$SO$_4$ and filtered. The solvent was evaporated and the residue was purified by flash chromatography (ethyl acetate) to give (±)-N-Boc-trans-3-(N-methyl-4-phenoxybenzenesulfonamido)-4-tertbutylmercaptopyrrolidine as a white powder (240 mg, 99%): $^1$H NMR (300 MHz, CD$_3$OD) δ 7.84 (d, J=8, 2H), 7.44 (t, J=8, 2H), 7.24 (t, J=8, 1H), 7.10 (m, 2H), 7.09 (d, J=9, 2H), 4.22 (m, 1H), 3.90 (m, 1H), 3.37 (m, 2H), 3.08 (m, 2H) 2.86 (s, 3H), 1.44 (s, 9H), 1.28 (s, 9H); MS (ESI) m/e 520.2 (M+); HRMS (ESI) calculated for C$_{26}$H$_{36}$N$_2$O$_5$S$_2$Na+ 543.1950. found 543.1950.

To a stirred solution of 1.5 M HCl in ethyl acetate (5 mL) was added (±)-N-Boc-trans-3-(N-methyl-4-phenoxybenzenesulfonamido)-4-tertbutylmercaptopyrrolidine (130 mg, 0.25 mmol) and stirring was continued at room temperature until no starting material was detected by TLC. The solvent was evaporated under reduced pressure and the residue was dissolved in CH$_2$Cl$_2$. The solution was cooled to 0° C. and triethylamine (46 µL, 0.33 mmol) and TMSNCO (100 µL, 0.74 mmol) were added successively. The solution was stirred at room temperature overnight. The reaction mixture was extracted with water and saturated brine, and was dried over Na$_2$SO$_4$ and filtered. The solvent was evaporated and the residue was purified by flash chromatography (5% MeOH in ethyl acetate) to give (±)-N-carbamoyl-trans-3-(N-methyl-4-phenoxybenzenesulfonamido)-4-tert-butylmercaptopyrrolidine as a white powder (110 mg, 95%): $^1$H NMR (300 MHz, CD$_3$OD) δ 7.85 (m, 2H), 7.42 (m, 2H), 7.22 (m, 1H), 7.10 (m, 4H), 4.24 (m, 1H), 3.96 (m, 1H), 3.42 (m, 2H), 3.08 (m, 2H), 2.87 (s, 3H), 1.28 (s, 9H); MS (ESI) m/e 463.2 (M+); HRMS (ESI) calcd for C$_{22}$H$_{29}$N$_3$O$_4$S$_2$Na+ 486.1479. found 486.1481.

To a solution of (±)-N-carbamoyl-trans-3-(N-methyl-4-phenoxybenzenesulfonamido)-4-tert-butylmercaptopyrrolidine (90 mg, 0.194 mmol) in AcOH (1 mL) was added 2-nitrobenzenesulfenyl chloride (38.6 mg, 0.204 mmol) and the mixture was stirred at room temperature for 2 hr. The AcOH was evaporated under vacuum, and to the residue was added THF (4 mL), 1N NaOH (0.25 mL) and TCEP (67 mg, 0.234 mmol). The mixture was stirred at room temperature under argon for 3 hr, then it was condensed under vacuum. To the residue was added ethyl acetate and it was dried over Na$_2$SO$_4$. The solvent was evaporated and the residue was purified by flash chromatography (5% MeOH in ethyl acetate) to give the product as a white powder (75.1 mg, 95%) (YHJ-7-23): $^1$H NMR (300 MHz, CD$_3$OD) δ7.87 (m, 2H), 7.44 (m, 2H), 7.24 (m, 1H), 7.10 (m, 4H), 4.32 (q, J=9, 1H), 3.83 (dd, J=10, 8 Hz, 1H), 3.42 (m, 2H), 3.13 (q, J=10, 2H), 2.83 (s, 3H); MS (ESI) m/e 407.2 (M+); HRMS (ESI) calcd for C$_{22}$H$_{29}$N$_3$O$_4$S$_2$Na+ 430.0864. found 430.0867.

Example 5

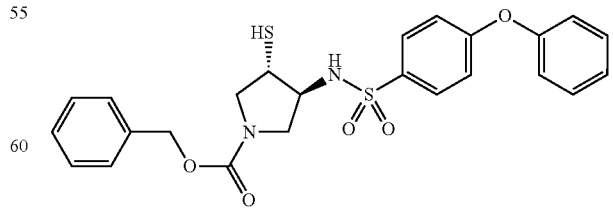

YHJ-6-90

YHJ-6-90: (±)-N-(Benzyloxycarbonyl)-trans-3-(4-phenoxybenzenesulfonamido)-4-mercaptopyrrolidine. To a stirred solution of 1.5 M HCl in ethyl acetate (10 mL) was added (±)-N-Boc-trans-3-(4-phenoxybenzenesulfonamido)-4-tert-butylmercaptopyrrolidine (103.2 mg, 0.2 mmol) and stirring was continued at room temperature until no starting material was detected by TLC (50% ethyl acetate in hexane). The solvent was evaporated under reduced pressure and the residue was dissolved in $CH_2Cl_2$ (10 mL) and cooled to 0° C. To the solution was added triethylamine (62 μL, 0.44 mmol) and benzyl chloroformate (31.4 μL, 0.22 mmol) successively. The solution was warmed to room temperature and was stirred for 2 hr. The reaction mixture was extracted with water, dried over $Na_2SO_4$, and evaporated under reduced pressure. The residue was purified by flash chromatography (25% ethyl acetate in hexane) to give (±)-N-(benzyloxycarbonyl)-trans-3-(4-phenoxybenzenesulfonamido)-4-tert-butylmercaptopyrrolidine as a white solid (105.0 mg, 95%): mp 125-126° C.; $^1$H NMR (300 MHz, CDCl$_3$) δ 7.80 (m, 2H), 7.40-7.30 (m, 7H), 7.22 (m, 1H), 7.12-7.10 (m, 4H), 5.10 (s, 2H), 4.85 (m, 1H), 4.00-3.75 (m, 2H), 3.40-3.00 (m, 4H), 1.32 (s, 9H); MS (ESI) m/e 540.2 (M+); HRMS (ESI) calcd for $C_{28}H_{32}N_2O_5S_2Na+$ 563.1645. found 563.1646.

To a solution of (±)-N-(benzyloxycarbonyl)-trans-3-(4-phenoxybenzenesulfonamido)-4-tert-butylmercaptopyrrolidine (151 mg, 0.28 mmol) in AcOH (2 mL) was added 2-nitrobenzenesulfenyl chloride (53 mg, 0.28 mmol) and the mixture was stirred at room temperature for 2 hr. The AcOH was evaporated under vacuum, and to the residue was added THF (5 mL), 1 N NaOH (0.52 mL) and TCEP (82 mg, 0.29 mmol). The mixture was stirred at room temperature under argon for 3 hr, then it was condensed under vacuum. To the residue was added ethyl acetate and it was dried over $Na_2SO_4$ and filtered. The solvent was evaporated and the residue was purified by flash chromatography (ethyl acetate) to give the mercaptan as a white solid (121 mg, 96%) (YHJ-6-90): mp 142-143° C.; $^1$H NMR (300 MHz, CD$_3$OD) δ 7.88 (d, J=8, 2H), 7.40 (m, 2H), 7.32 (m, 5H), 7.22 (t, J=8, 1H), 7.15 (m, 4H), 5.08 (s, 2H), 3.81 (m, 1H), 3.72-3.50 (m, 2H), 3.20 (m, 2H), 3.07 (m, 1H); MS (ESI) m/e 484.1 (M+); HRMS (ESI) calcd for $C_{22}H_{29}N_2O_5S_2Na+$ 507.1017. found 507.1020.

Example 6

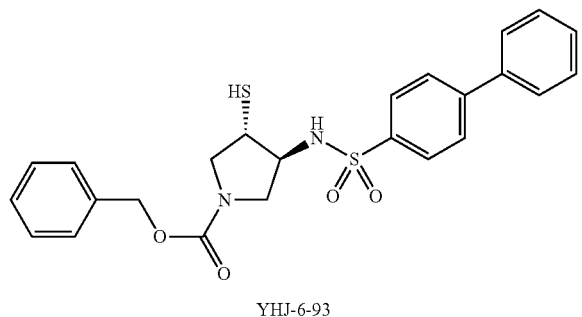 [SMILES: O=C(OCc1ccccc1)N1C[C@H](NS(=O)(=O)c2ccc(-c3ccccc3)cc2)[C@@H](S)C1]

YHJ-6-93

YHJ-6-93: (±)-N-(Benzyloxycarbonyl)-trans-3-(4-phenylbenzenesulfonamido)-4-mercaptopyrrolidine. Following the same synthetic procedures as described above (Scheme 1), N-(benzyloxycarbonyl)-3-pyrroline oxide was used to prepare (±)-N-(benzyloxycarbonyl)-trans-3-(4-phenylbenzenesulfonamido)-4-tert-butylmercaptopyrrolidine as a white solid: mp 99-100° C.; $^1$H NMR (300 MHz, CDCl$_3$) δ 7.92 (d, J=8, 2H), 7.40 (d, J=8, 2H), 7.60 (m, 2H), 7.53-7.40 (m, 3H), 7.33 (m, 5H), 5.11 (s, 2H), 4.89 (m, 1H), 4.00-3.80 (m, 2H), 3.40-3.00 (m, 4H), 1.31 (s, 9H); MS (ESI) m/e 524.2 (M+); HRMS (ESI) calcd for $C_{28}H_{32}N_2O_4S_2Na+$ 547.1688. found 547.1687.

To a solution of (±)-N-(benzyloxycarbonyl)-trans-3-(4-phenylbenzenesulfonamido)-4-tert-butylmercaptopyrrolidine (130 mg, 0.25 mmol) in AcOH (1 mL) was added 2-nitrobenzenesulfenyl chloride (52 mg, 0.27 mmol) and the mixture was stirred at room temperature for 2 hr. The AcOH was evaporated under vacuum, and to the residue was added THF (5 mL), 1 N NaOH (0.50 mL) and TCEP (82 mg, 0.29 mmol). The mixture was stirred at room temperature under argon for 3 hr, then it was condensed under vacuum. To the residue was added ethyl acetate and it was dried over $Na_2SO_4$ and filtered. The solvent was evaporated and the residue was purified by flash chromatography (ethyl acetate) to give the mercaptan as a white solid (110 mg, 94%) (YHJ-6-93): mp 151-152.5° C.; $^1$H NMR (300 MHz, CDCl$_3$) δ 7.94 (d, J=8, 2H), 7.74 (d, J=8, 2H), 7.60 (m, 2H), 7.52-7.40 (m, 3H), 7.32 (m, 5H), 5.10 (s, 2H), 5.06 (m, 1H), 3.89 (m, 2H), 3.53 (m, 1H), 3.38-3.10 (m, 3H), 1.70 (d, J=7, 0.5H), 1.61 (d, J=7, 0.5H); MS (ESI) m/e 468.1 (M+); HRMS (ESI) calcd for $C_{24}H_{24}N_2O_4S_2Na+$ 491.1067. found 491.1064.

Example 7

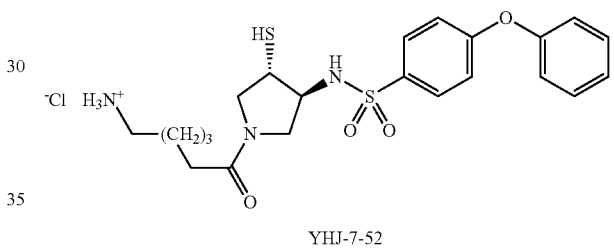

YHJ-7-52

YHJ-7-52: (±)-N-(6-Aminohexanoyl)-trans-3-(4-phenoxybenzene-sulfonamido)-4-mercaptopyrrolidine Hydrochloride. To a stirred solution of 1.5 M HCl in ethyl acetate (1 mL) was added (±)-N-Boc-trans-3-(4-phenoxybenzenesulfonamido)-4-tert-butylmercaptopyrrolidine (200 mg, 0.39 mmol) and stirring was continued at room temperature until no starting material was detected by TLC (50% ethyl acetate in hexane). The solvent was evaporated under reduced pressure and the residue was dissolved in $CH_2Cl_2$. The solution was cooled to 0° C. and triethylamine (60 μL, 0.43 mmol), HOBt.H$_2$O (54 mg, 0.40 mmol), 6-(tert-butoxycarbonylamino)hexanoic acid (90 mg, 0.39 mmol) and DCC (80 mg, 0.39 mmol) were added. The mixture was stirred at room temperature overnight. The solvent was evaporated under reduced pressure and the residue was dissolved in ethyl acetate (10 mL) and the organic layer was washed with 10% citric acid and sat. aq NaHCO$_3$, then it was dried over $Na_2SO_4$ and evaporated. The residue was purified by flash chromatography (50% ethyl acetate in hexane) to give (±)-N-(6-(tert-butoxycarbonylamino)hexanoyl)-trans-3-(4-phenoxybenzenesulfonamido)-4-tert-butylmercaptopyrrolidine (201 mg, 84%): $^1$H NMR (300 MHz, CDCl$_3$) δ 7.82 (dd, J=9, 3, 2H), 7.43 (t, J=8, 2H), 7.24 (t, J=7, 1H), 7.08 (m, 4H), 5.13 (br m, 1H, NH), 4.57 (br s, 1H, NH), 3.72-4.10 (m, 2H), 3.00-3.45 (m, 6H), 2.21 (t, J=7, 2H), 1.64 (m, 2H), 1.48 (m, 2H), 1.44 (s, 9H), 1.36 & 1.30 (s, 9H), 1.26 (m, 2H); HRMS (ESI) calculated for $C_{31}H_{45}N_3O_6S_2Na^+$ 642.2642. found 642.2654.

To a solution of (±)-N-(6-(tert-butoxycarbonylamino)hexanoyl)-trans-3-(4-phenoxybenzenesulfonamido)-4-tert-butylmercaptopyrrolidine (130 mg, 0.21 mmol) in AcOH—CH₂Cl₂ (1:1, 1 mL) was added 2-nitrobenzenesulfenyl chloride (42 mg, 0.22 mmol) and the mixture was stirred at room temperature for 2 hr. The solvents were evaporated under vacuum and the residue was purified by flash chromatography (50% ethyl acetate in hexane) to give (±)-N-(6-(tert-butoxycarbonylamino)hexanoyl)-trans-3-(4-phenoxybenzenesulfonamido)-4-(2-nitrobenzenedisulfido)pyrrolidine (110 mg, 73%): ¹H NMR (300 MHz, CDCl₃) δ 8.28 (m, 1H), 8.22 & 8.11 (d, J=8, 1H), 7.75 (m, 3H), 7.42 (m, 3H), 7.24 (m, 1H), 7.10 (m, 2H), 7.02 (m, 2H), 5.40 & 5.12 (br s, 1H, NH), 4.57 (br s, 1H, NH), 3.75-4.00 (m, 3H), 3.21-3.53 (m, 3H), 2.95-3.14 (m, 2H), 2.19 (m, 2H), 1.61 (m, 2H), 1.47 (m, 2H), 1.43 (s, 9H), 1.33 (m, 2H).

To a solution of the 2-nitrobenzenedisulfide (50 mg, 0.7 mmol) in THF—H₂O (4:1, 1 mL) was added TCEP (23 mg, 0.8 mmol) and 1 N NaOH (100 μL). The mixture was stirred until no starting material was detected by TLC (50% ethyl acetate in hexane). The solution was evaporated under reduced pressure and the residue was purified by short flash column chromatography (50% ethyl acetate in hexane) to give the mercaptan. The latter was dissolved in 2M HCl in acetic acid (1 mL) and the mixture was stirred at room temperature for 1 hr. Liophylization of the solution gave the mercaptan as white hydroscopic solid (33 mg, 94%) (YHJ-7-52): ¹H NMR (300 MHz, CD₃OD) δ 7.88 (m, 2H), 7.45 (t, J=8, 2H), 7.25 (t, J=8, 1H), 7.10 (m, 4H), 3.84-3.97 (m, 2H), 3.71 (dd, J=12, 7, 1H), 3.52-3.64 (m, 2H), 3.06-3.18 (m, 1H), 2.93 (br m, 2H), 2.31 (q, J=7, 2H), 1.66 (br m, 4H), 1.42 (br m, 2H); HRMS (ESI) calculated for $C_{22}H_{30}N_3O_4S_2^+$ 464.1672. found 464.1672.

Example 8

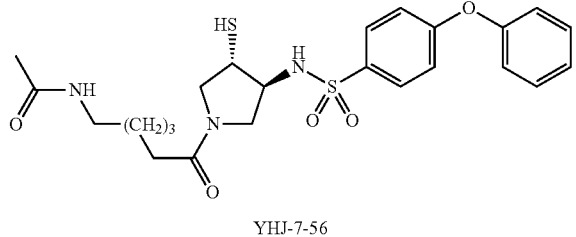

YHJ-7-56

YHJ-7-56: (±)-N-(6-Acetamidohexanoyl)-trans-3-(4-phenoxy-benzenesulfonamido)-4-mercaptopyrrolidine. A solution of (±)-N-(6-(tert-butoxy-carbonylamino)hexanoyl)-trans-3-(4-phenoxybenzenesulfonamido)-4-(2-nitrobenzene-disulfido)pyrrolidine (78 mg, 0.11 mmol) in trifluoroacetic acid (1 mL) was stirred at room temperature for 1 hr. The trifluoroacetic acid was evaporated under vacuum and the residue was dissolved in CH₂Cl₂ (1 mL). The solution was cooled to 0° C. and triethylamine (34 μL, 0.244 mmol) and acetyl chloride (8.6 μL, 0.12 mmol) were added, and the mixture was stirred for 2 hr. The solution was evaporated; the residue was dissolved in ethyl acetate (5 mL), washed with water, dried over Na₂SO₄, and the solvent was evaporated. The residue was purified by flash chromatography (100% ethyl acetate) to give (±)-N-(6-acetamidohexanoyl)-trans-3-(4-phenoxybenzene-sulfonamido)-4-(2-nitrobenzenedisulfido)pyrrolidine (68 mg, 94%): ¹H NMR (300 MHz, CD₃OD) δ 8.20-8.33 (m, 2H), 7.76 (m, 3H), 7.47 (m, 3H), 7.25 (t, J=8, 1H), 7.10 (d, J=9, 2H), 6.99 (m, 2H), 3.92 (m, 2H), 3.68-3.86 (m, 2H), 3.52 (m, 1H), 3.39 (m, 1H), 3.14 (m, 2H), 2.24 (m, 2H), 1.93 & 1.92 (s, 3H), 1.54 (m, 4H), 1.34 (m, 2H).

To a solution of the 2-nitrobenzenedisulfide (10 mg, 0.015 mmol) in THF—H₂O (4:1, 1 mL) was added TCEP (5 mg, 0.017 mmol) and 1N NaOH (20 μL). The mixture was stirred until no starting material was detected on TLC (100% ethyl acetate). The solvent was evaporated under reduced pressure and the residue was purified by short flash column chromatography (100% ethyl acetate) to give the mercaptan (7 mg, 91%) (YHJ-7-56): ¹H NMR (300 MHz, CD₃OD) δ 7.88 (m, 2H), 7.45 (t, J=8, 2H), 7.25 (t, J=8, 1H), 7.10 (m, 4H), 3.81-3.98 (m, 2H), 3.53-3.72 (m, 2H), 3.05-3.40 (m, 4H), 2.26 (m, 2H), 1.92 (s, 3H), 1.46-1.65 (m, 4H), 1.30-1.41 (m, 2H); HRMS (ESI) calculated for $C_{24}H_{32}N_3O_5S_2^+$ 506.1778. found 506.1786.

Example 9

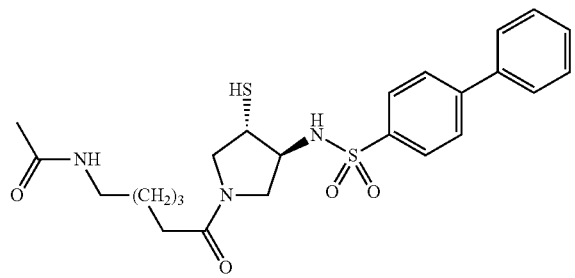

YHJ-7-75

YHJ-7-75: (±)-N-(6-Acetamidohexanoyl)-trans-3-(4-phenylbenzene-sulfonamido)-4-mercaptopyrrolidine. To a solution of (±)-N-Boc-trans-3-azido-4-hydroxypyrrolidine (228 mg, 1.0 mmol) in THF—H₂O (10:1, 5 mL) was added Ph₃P (275 mg, 1.05 mmol), and the mixture was stirred at room temperature for 2 hr and at 65° C. until no starting material was detected on TLC (25% ethyl acetate in hexane). The solution was cooled with stirring to 0° C., and triethylamine (167 μL, 1.2 mmol) was added, then a solution of 4-phenyl-benzenesulfonyl chloride (256 mg, 1.1 mmol) in THF (2 mL) was added dropwise. The reaction mixture was warmed to room temperature and was stirred for 3 hr. The mixture was concentrated under reduced pressure, ethyl acetate was added to the residue and the organic layer was washed with 10% aq citric acid and sat. aq NaHCO₃, then it was dried over Na₂SO₄ and evaporated. The residue was purified by flash chromatography (50% ethyl acetate in hexane) to give (±)-N-Boc-trans-3-(4-phenylbenzenesulfonamido)-4-hydroxypyrrolidine (337 mg, 73.5%): ¹H NMR (300 MHz, CDCl₃+CD₃OD) δ 7.88 (d, J=8, 2H), 7.69 (d, J=8, 2H), 7.56 (d, J=8, 2H), 7.41 (m, 3H), 4.06 & 4.20 (br m, 1H), 3.52 (br m, 3H), 3.12 (m, 2H), 1.36 & 1.38 (s, 9H); HRMS (ESI) calculated for $C_{21}H_{26}N_2O_5SNa^+$ 441.1460. found 441.1469.

To a stirred solution of Ph₃P (242 mg, 0.92 mmol) and (±)-N-Boc-trans-3-(4-phenylbenzenesulfonamido)-4-hydroxypyrrolidine (350 mg, 0.84 mmol) in THF (20 mL) at 0° C. was added diethyl azodicarboxylate (DEAD) (160 μL, 1.0 mmol) dropwise. The reaction mixture was stirred at room temperature overnight, then it was evaporated under reduced pressure. The residue was purified by flash chromatography (30% ethyl acetate in hexane) to give the N-(4-phenylbenzenesulfonyl)aziridine (317 mg, 95%): ¹H NMR (300 MHz, CDCl$_3$) δ 8.01 (d, J=8, 2H), 7.76 (d, J=8, 2H), 7.62 (d, J=7, 2H), 7.48 (m, 3H), 3.73 (dd, J=12, 2, 2H), 3.64 (dd, J=6, 2, 1H), 3.53 (dd, J=6, 2, 1H), 3.40 (m, 2H), 1.42 (s, 9H); HRMS (ESI) calculated for C$_{21}$H$_{24}$N$_2$O$_4$SNa$^+$ 423.1355. found 423.1355.

To a solution of the aziridine (300 mg, 0.75 mmol) and tert-butyl mercaptan (100 mL, 1.4 mmol) in anhydrous methanol (5 mL) at 0° C. was added t-BuOK (10 mg, 0.09 mmol). The mixture was stirred at room temperature for 4 hr, then it was evaporated under reduced pressure. Ethyl acetate was added to the residue and the solution was extracted with water and with sat. brine, then it was dried over Na$_2$SO$_4$ and evaporated. The residue was purified by flash chromatography (20% ethyl acetate in hexane) to give (±)-N-Boc-trans-3-(4-phenylbenzenesulfonamido)-4-tert-butylmercaptopyrrolidine (361 mg, 98%): $^1$H NMR (300 MHz, CDCl$_3$) δ 7.94 (d, J=8, 2H), 7.75 (d, J=8, 2H), 7.61 (d, J=7, 2H), 7.47 (m, 3H), 4.92 (br, 1H, NH), 3.71-3.95 (br m, 2H), 3.00-3.45 (br m, 4H), 1.44 (s, 9H), 1.31 (br s, 9H); HRMS (ESI) calculated for C$_{25}$H$_{34}$N$_2$O$_4$S$_2$Na$^+$ 513.1864. found 513.1864.

To a solution of 1.5 M HCl in ethyl acetate (1 mL) was added (±)-N-Boc-trans-3-(4-phenylbenzenesulfonamido)-4-tert-butylmercaptopyrrolidine (220 mg, 0.45 mmol) and the mixture was stirred until no starting material could be detected by TLC (50% ethyl acetate). The solvent was evaporated under reduced pressure and the residue was dissolved in CH$_2$Cl$_2$ (2 mL) and cooled to 0° C. To the solution was added triethylamine (69 μL, 0.50 mmol), HOBt.H$_2$O (61 mg, 0.45 mmol), and 6-(tert-butoxy-carbonylamino)hexanoic acid (104 mg, 0.39 mmol) and DCC (92 mg, 0.45 mmol). The mixture was stirred overnight, then it was concentrated under reduced pressure. The residue was dissolved in ethyl acetate (10 mL) and the organic layer was washed with 10% citric acid and sat. aq NaHCO$_3$, then it was dried over Na$_2$SO$_4$ and evaporated. The residue was purified by flash chromatography (50% ethyl acetate in hexane) to give (±)-N-(6-(tert-butoxycarbonylamino)hexanoyl)-trans-3-(4-phenylbenzenesulfonamido)-4-tert-butylmercaptopyrrolidine (220 mg, 81%): $^1$H NMR (300 MHz, CDCl$_3$) δ 7.94 (dd, J=9, 4, 2H), 7.75 (t, J=8, 2H), 7.61 (m, 2H), 7.46 (m, 3H), 5.21 (br s, 1H, NH), 4.56 (br s, 1H, NH), 3.77-4.11 (m, 2H), 3.02-3.49 (m, 6H), 2.22 (t, J=7, 2H), 1.63 (m, 2H), 1.49 (m, 2H), 1.44 (s, 9H), 1.36 & 1.29 (s, 9H), 1.25 (m, 2H); HRMS (ESI) calculated for C$_{31}$H$_{45}$N$_3$O$_5$S$_2$Na$^+$ 626.2698. found 626.2699.

The N-(6-(tert-butoxycarbonylamino)hexanoyl)-substituted pyrrolidine (92 mg, 0.15 mmol) was dissolved in 1.5 M HCl in ethyl acetate (1 mL) and the resulting solution was stirred for 1 hr. The mixture was evaporated under vacuum and the residue was dissolved in CH$_2$Cl$_2$ (1 mL) and was cooled to 0° C. To the solution was added triethylamine (46 μL, 0.33 mmol) and acetyl chloride (11 μL, 0.16 mmol), and the mixture was stirred for 2 hr. The solution was evaporated under vacuum; the residue was dissolved in ethyl acetate (5 mL) and was washed with water, then dried over Na$_2$SO$_4$ and evaporated. The residue was purified by flash chromatography (100% ethyl acetate) to give (±)-N-(6-acetamidohexanoyl)-trans-3-(4-phenylbenzenesulfonamido)-4-tert-butylmercaptopyrrolidine (75 mg, 92%): $^1$H NMR (300 MHz, CDCl$_3$) δ 7.96 & 7.95 (d, J=8, 2H), 7.74 & 7.72 (d, J=8, 2H), 7.60 (m, 2H), 7.47 (m, 3H), 6.69 (br s, 0.5H, NH), 6.45 (br s, 0.5H, NH), 5.82 (br s, 1H, NH), 4.06 (m, 1H), 3.68-3.86 (m, 1H), 3.28-3.65 (m, 4H), 3.18 (m, 2H), 2.24 (m, 2H), 2.00 & 1.98 (s, 3H), 1.64 (m, 2H), 1.51 (m, 2H), 1.22-1.41 (m, 2H), 1.34 & 1.29 (s, 9H); HRMS (ESI) calculated for C$_{28}$H$_{39}$N$_3$O$_4$S$_2$Na$^+$ 568.2286. found 568.2284.

To a solution of (±)-N-(6-acetamidohexanoyl)-trans-3-(4-phenyl-benzenesulfonamido)-4-tert-butylmercaptopyrrolidine (59 mg, 0.11 mmol) in acetic acid (1 mL) was added 2-nitrobenzenesulfenyl chloride (23 mg, 0.12 mmol) and the mixture was stirred at room temperature for 2 hr. The solvent was evaporated under vacuum and the residue was purified by flash chromatography (100% ethyl acetate) to give the 2-nitrobenzenedisulfide (65 mg, 94%): $^1$H NMR (300 MHz, CDCl$_3$) δ 8.25 (d, J=8, 1H), 8.15 (dd, J=5, 7, 1H), 7.85 (t, J=9, 2H), 7.55-7.70 (m, 5H), 7.38-7.53 (m, 3H), 7.33 (t, J=8, 1H), 7.18 (br d, J=5, 1H, NH), 5.67 (br s, 1H, NH), 3.83-4.07 (m, 3H), 3.32-3.48 (m, 4H), 2.98-3.16 (m, 1H), 2.29 (m, 1H), 2.16 (m, 1H), 2.00 (s, 3H), 1.69 (m, 2H), 1.50 (m, 2H), 1.35 (m, 2H); HRMS (ESI) calculated for C$_{30}$H$_{34}$N$_4$O$_6$S$_3$Na$^+$ 665.1560. found 665.1556.

To a solution of the 2-nitrobenzenedisulfide (64 mg, 0.1 mmol) in THF—H$_2$O (4:1, 1 mL) was added TCEP (32 mg, 0.11 mmol) and 1N NaOH (200 μL). The mixture was stirred until no starting material was detected on TLC (50% ethyl acetate in hexane). The solution was evaporated under reduced pressure and the residue was purified by short flash column chromatography (5% MeOH in ethyl acetate) to give the mercaptan (45 mg, 92%) (YHJ-7-75): $^1$H NMR (300 MHz, CDCl$_3$) δ 7.98 & 7.95 (d, J=8, 2H), 7.75 & 7.73 (d, J=8, 2H), 7.62 (m, 2H), 7.45 (m, 3H), 6.91 (d, J=6, 1H, NH), 5.87 (br d, J=5, 1H, NH), 3.83-4.08 (m, 2H), 3.63 (m, 1H), 3.25-3.51 (m, 4H), 3.14 (m, 1H), 2.13-2.37 (m, 2H), 2.02 & 1.99 (s, 3H), 1.81 & 1.68 (d, J=7, 1H, SH), 1.65 (m, 2H), 1.51 (m, 2H), 1.35 (m, 2H); HRMS (ESI) calculated for C$_{24}$H$_{31}$N$_3$O$_4$S$_2$Na$^+$ 512.1684. found 512.1684.

Enzymatic Resolution of (±)-N-Boc-trans-3-Azido-4-hydroxy-pyrrolidine. To a solution of (±)-N-Boc-trans-3-azido-4-hydroxypyrrolidine (2.28 g, 10 mmol) in tert-butyl methyl ether (50 mL) was added isopropenyl acetate (3 g, 3 mmol) and lipase Amano AK-20 (3 g), and the mixture was stirred at room temperature for 72 hr. The mixture was filtered, the filtrate was evaporated under reduced pressure, and the product was separated by flash chromatography (25% ethyl acetate in hexane). First eluted was (3R,4R)-N-Boc-3-azido-4-acetoxypyrrolidine (1.30 g): $^1$H NMR (300 MHz, CDCl$_3$) δ 5.09 (br s, 1H), 4.04 (m, 1H), 3.57-3.74 (m, 2H), 3.34-3.55 (m, 2H), 2.09 (s, 3H), 1.47 (s, 9H); [α]$_{20}^D$=−30.4° (c=1.0, CHCl$_3$).

Second to be eluted was (3S,4S)—N-Boc-3-azido-4-hydroxypyrrolidine (1.07 g): $^1$H NMR (300 MHz, CDCl$_3$) δ 4.25 (br s, 1H), 3.93 (br s, 1H), 3.55-3.75 (m, 2H), 3.30-3.50 (m, 2H), 2.05 (br s, 1H), 1.46 (s, 9H); [α]$_{20}^D$=+26.8° (c=0.5, CHCl$_3$).

To a stirred solution of (3R,4R)—N-Boc-3-azido-4-acetoxypyrrolidine (1.0 g, 3.4 mmol) in THF-MeOH (3:1, 8 mL) at 0° C. was added 1N LiOH (4 mL) dropwise. The reaction mixture was stirred at room temperature overnight, then it was evaporated under reduced pressure. Ethyl acetate (20 mL) was added to the residue and the solution was washed with brine, dried over Na$_2$SO$_4$ and evaporated. The residue was purified by flash column (50% ethyl acetate in hexane) to give (3R,4R)—N-Boc-3-azido-4-hydroxypyrrolidine: $^1$H NMR (300 MHz, CDCl$_3$) identical to that of the (3S,4S) isomer; [α]$_{20}^D$=−26.8° (c=1.0, CHCl$_3$).

A sample of the (3S,4S)—N-Boc-3-azido-4-hydroxypyrrolidine (80 mg, 0.35 mmol) was dissolved in trifluoroacetic acid (1 mL) and was stirred until no starting material was detected on TLC (25% ethyl acetate in hexane). The solution was evaporated under reduce pressure and the residue was dissolved in CH$_2$Cl$_2$ (2 mL). The solution was cooled to 0° C., triethylamine (117 μL, 0.84 mmol) and Cbz-Cl (60 mg, 0.35 mmol) were added, and the resulting solution was stirred for 2 hr at room temperature. The reaction mixture was washed with water, dried over Na$_2$SO$_4$, and evaporated. The residue was purified by flash chromatography (25% ethyl acetate in hexane) to give (3S,4S)—N-Cbz-3-azido-4-hydroxypyrrolidine (89 mg, 97%): $[\alpha]_{20}^D = +16.1°$ (c=1.00, CHCl$_3$). Lit. [Kamal, A.; Shaik, A. A.; Sandbhor, M.; Malik, M. S.; Kaga, H. *Tetrahedron Lett.* 2004, 45, 8057-8059] for (3S,4S)—N-Cbz-3-azido-4-hydroxypyrrolidine: $[0]_{25}^D = +14.3°$ (c=1.06, CHCl$_3$).

Example 10

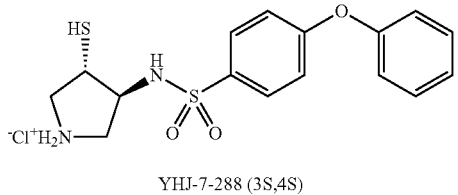

YHJ-7-288 (3S,4S)

YHJ-7-288: (3S,4S)-3-(4-Phenoxybenzenesulfonamido)-4-mercaptopyrrolidine Hydrochloride. A solution of (3S,4S)—N-Boc-3-azido-4-hydroxypyrrolidine (850 mg, 3.72 mmol) and triethylamine (622 μL, 4.46 mmol) in CH$_2$Cl$_2$ (10 mL) was cooled with stirring to 0° C., and methanesulfonyl chloride (331 μl, 4.28 mmol) was added dropwise. The solution was stirred at room temperature until no starting material was detected by TLC (25% ethyl acetate in hexane). The reaction mixture was washed with 10% aq. citric acid, water, dried over Na$_2$SO$_4$ and evaporated. The residual crude methanesulfonate was dissolved in anhydrous DMF (20 mL), potassium acetate (1.10 g, 11.2 mmol) was added, and the mixture was stirred at 105° C. under nitrogen for 6 hr. The reaction mixture was poured into ice water and was extracted with ethyl acetate (20 ml×3). The organic layer was washed with brine, dried over Na$_2$SO$_4$ and evaporated. The residue was purified by flash chromatography (25% ethyl acetate in hexane) to give (3S,4R)—N-Boc-3-azido-4-acetoxypyrrolidine (860 mg, 86%): $^1$H NMR (300 MHz, CDCl$_3$) δ 5.31 (br m, 1H), 4.07 (m, 1H), 3.60-3.71 (m, 2H), 3.36-3.50 (m, 2H), 2.16 (s, 3H), 1.46 (s, 9H); $[\alpha]_{20}^D = -34.5°$ (c=1.00, CHCl$_3$).

To a stirred solution of the (3S,4R)-azidoacetate (560 mg, 2.07 mmol) in THF-MeOH (3:1, 8 mL) at 0° C. was added 1N LiOH (3 mL) dropwise. The reaction mixture was stirred at room temperature overnight, then it was evaporated under reduced pressure. Ethyl acetate (20 mL) was added to the residue and the solution was washed with brine, dried over Na$_2$SO$_4$ and evaporated. The residue was purified by flash chromatography (50% ethyl acetate in hexane) to give (3S,4R)—N-Boc-3-azido-4-hydroxypyrrolidine (460 mg, 97%): $^1$H NMR (300 MHz, CDCl$_3$) δ 4.35 (br m, 1H), 4.02 (br m, 1H), 3.25-3.72 (m, 4H), 2.16 (br s, 1H), 1.46 (s, 9H); $[\alpha]_{20}^D = +32.3°$ (c=0.69, CHCl$_3$).

To a solution of the (3S,4R)-azidoalcohol (470 mg, 2.06 mmol) in THF—H$_2$O (10:1, 10 mL) was added Ph$_3$P (540 mg, 2.06 mmol), and the mixture was stirred at room temperature for 2 hr and at 65° C. until no starting material detected on TLC (25% ethyl acetate in hexane). The solution was cooled with stirring to 0° C. and triethylamine (345 μL, 2.48 mmol) was added, then a solution of 4-phenoxybenzenesulfonyl chloride (529 mg, 2.26 mmol) in THF (2 mL) was added dropwise. The reaction mixture was warmed to room temperature and was stirred for 3 hr. The mixture was concentrated under reduced pressure, ethyl acetate was added to the residue, and the organic layer was washed with 10% aq citric acid and sat. aq NaHCO$_3$, then it was dried over Na$_2$SO$_4$ and evaporated. The residue was purified by flash chromatography (50% ethyl acetate in hexane) to give the product as a solid (670 mg, 75%) to give (3S,4R)—N-Boc-3-(4-phenoxybenzenesulfonamido)-4-hydroxypyrrolidine: $^1$H NMR (300 MHz, CDCl$_3$) δ 7.83 (d, J=7, 2H), 7.42 (t, J=8, 2H), 7.24 (t, J=8, 1H), 7.06 (m, 4H), 5.14 (br s, 1H), 4.25 & 4.11 (br s, 1H), 3.76 (m, 1H), 3.55 (m, 1H), 3.43 (m, 2H), 3.07 (m, 1H), 2.36 & 2.23 (br s, 1H) 1.43 (s, 9H); $[\alpha]_{20}^D = +15.6°$ (c=0.80, CHCl$_3$).

To a stirred solution of PPh$_3$ (525 mg, 2.0 mmol) in THF (3 mL) at 0° C. was added DEAD (315 μL, 2.0 mmol) dropwise. After 10 min, a solution of (3S,4R)—N-Boc-3-(4-phenoxybenzenesulfonamido)-4-hydroxypyrrolidine (435 mg, 1.0 mmol) and thiolacetic acid (228 μL, 2.29 mmol) in THF (3 mL) was added. The resulting reaction mixture was stirred at room temperature for 6 hr, then it was concentrated under reduced pressure. The residue was purified be flash chromatography (15% ethyl acetate in hexane) to give (3S,4S)—N-Boc-3-(4-phenoxybenzenesulfonamido)-4-acetylthiopyrrolidine (400 mg, 81%): $^1$H NMR (300 MHz, CDCl$_3$) δ 7.80 (d, J=9, 2H), 7.42 (m, 2H), 7.23 (t, J=8, 1H), 7.06 (m, 4H), 5.21 & 5.00 (br s, 1H, NH), 3.75 (m, 4H), 3.16 (m, 2H), 2.31 & 2.25 (br s, 3H), 1.44 (s, 9H); $[\alpha]_{20}^D = +22.8°$ (c=0.62, CHCl$_3$).

To a stirred solution of the acetylthiopyrrolidine (60 mg, 0.122 mmol) in MeOH (1 mL) under nitrogen was added 40% aq MeNH$_2$ (100 μL, 1.16 mmol) and the mixture was stirred for 10 min. The solution was concentrated under vacuum and the residue was purified by flash chromatography (50% ethyl acetate in hexane) to give (3S,4S)—N-Boc-3-(4-phenoxybenzenesulfonamido)-4-mercaptopyrrolidine (54 mg, 98%) as an oil: $^1$H NMR (300 MHz, CD$_3$OD) identical to that of the (±)-modification described in Example 3; $[\alpha]_{20}^D = +39.2°$ (c=0.54, MeOH).

To a solution of 2.0 M HCl in AcOH (1 mL) was added (3S,4S)—N-Boc-3-(4-phenoxybenzenesulfonamido)-4-mercaptopyrrolidine (45 mg, 0.10 mmol) and the mixture was stirred at room temperature for 1 hr. Liophylization of the reaction mixture gave the product as a white hygroscopic solid (37 mg, 100%) (YHJ-7-288): $^1$H NMR (300 MHz, CD$_3$OD) identical to that of the racemic inhibitor YHJ-6-293 (Example 3); $[\alpha]_{20}^D = +21.9°$ (c=0.7, MeOH); HRMS (ESI) calculated for C$_{16}$H$_{19}$N$_2$O$_3$S$_2^+$ 351.0832, 351.0824.

Example 11

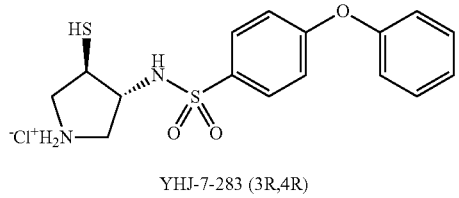

YHJ-7-283 (3R,4R)

YHJ-7-283: (3R,4R)-3-(4-Phenoxybenzenesulfonamido)-4-mercaptopyrrolidine Hydrochloride. By the procedures of Example 10, (3R,4R)—N-Boc-3-azido-4-hydroxypyrrolidine was converted to the title inhibitor as a white hygroscopic solid (YHJ-7-283): $^1$H NMR (300 MHz, CD$_3$OD) identical to that of YHJ-7-288 (Example 10); $[\alpha]_{20}^D = -21.0°$ (c=1.0, MeOH); HRMS (ESI) calculated for C$_{16}$H$_{19}$N$_2$O$_3$S$_2^+$ 351.0832, 351.0820.

Example 12

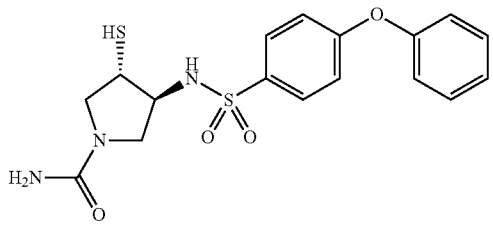

YHJ-7-291 (3S,4S)

YHJ-7-291: (3S,4S)—N-Carbamoyl-3-(4-phenoxybenzene-sulfonamido)-4-mercaptopyrrolidine. To a stirred solution of (3S,4S)—N-Boc-3-(4-phenoxybenzenesulfonamido)-4-acetylthiopyrrolidine (105 mg, 0.214 mmol) in MeOH (2 mL) under nitrogen was added 40% aq MeNH$_2$ (200 µL, 2.32 mmol) and the mixture was stirred for 10 min. The solution was concentrated under vacuum and the residue was dissolved in CH$_2$Cl$_2$ (2 mL). To the solution was added 2-nitrobenzenesulfenyl chloride (42 mg, 0.22 mmol) and the mixture was stirred at room temperature for 2 hr. The solvent was evaporated under vacuum and the residue was purified by flash chromatography (50% ethyl acetate in hexane) to give (3S,4S)—N-Boc-3-(4-phenoxy-benzenesulfonamido)-4-(2-nitrobenzenedisulfido)pyrrolidine (110 mg, 85%): $^1$H NMR (300 MHz, CDCl$_3$) δ 8.28 (d, J=8, 1H), 8.18 (br m, 1H), 7.72 (br m, 3H), 7.41 (m, 3H), 7.24 (t, J=8, 1H), 7.10 (d, J=8, 2H), 7.02 (br m, 2H), 3.68-3.83 (br m, 3H), 3.13-3.53 (br m, 3H), 1.42 (s, 9H); $[α]_{20}^D$=−55.4° (c=0.52, CHCl$_3$).

A solution of the 2-nitrobenzenedisulfide (80 mg, 0.133 mmol) in trifluoroacetic acid (1 mL) was stirred at room temperature until no starting material was detected on TLC (50% ethyl acetate in hexane). The trifluoroacetic acid was evaporated under reduced pressure and the residue was dissolved in CH$_2$Cl$_2$ (1 mL). The solution was cooled to 0° C. and triethylamine (23 µL, 0.17 mmol) and TMSNCO (100 µL, 0.74 mmol) were added successively. The mixture was stirred at room temperature overnight. The reaction mixture was extracted with water and sat. brine, and was dried over Na$_2$SO$_4$ and filtered. The solvent was evaporated and the residue was purified by flash chromatography (5% MeOH in ethyl acetate) to give (3S,4S)—N-carbamoyl-3-(4-phenoxy-benzenesulfonamido)-4-(2-nitrobenzenedisulfido)pyrrolidine (72 mg, 99%): $^1$H NMR (300 MHz, CDCl$_3$) δ 8.29 (d, J=8, 1H), 8.17 (d, J=8, 1H), 7.72 (m, 3H), 7.42 (m, 3H), 7.24 (t, J=8, 1H), 7.09 (d, J=8, 2H), 6.99 (d, J=9, 2H), 6.90 (br s, 1H, NH), 4.74 (s, 2H, NH), 3.91 (dd, J=11, 6, 1H), 3.71 (m, 3H), 3.62 (m, 1H), 3.29 (dd, J=11, 3, 1H); $[α]_{20}^D$=−129° (c=0.50, CHCl$_3$).

To a solution of the carbamoyl derivative (60 mg, 0.11 mmol) in THF (2 mL) was added 1N NaOH (0.15 mL) and TCEP (35 mg, 0.12 mmol). The mixture was stirred at room temperature under argon for 3 hr, then it was condensed under vacuum. To the residue was added ethyl acetate, washed with water and dried over Na$_2$SO$_4$. The solvent was evaporated and the residue was purified by flash chromatography (5% MeOH in ethyl acetate) to give the inhibitor as a white powder after liophylization from AcOH (42 mg, 97%) (YHJ-7-291): $^1$H NMR (300 MHz, CD$_3$OD) identical to that of the racemic inhibitor YHJ-6-286 (Example 1); $[α]_{20}^D$=+39.8 (c=0.54, MeOH); HRMS (ESI) calculated for C$_{17}$H$_{19}$N$_3$O$_4$S$_2$Na$^+$ 416.0714. found 416.0716.

Example 13

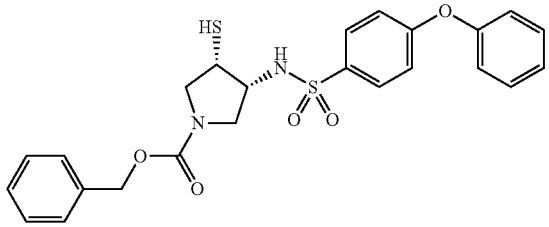

YHJ-7-256 (3R,4S)

YHJ-7-256: (3R,4S)—N-Cbz-3-(4-Phenoxybenzenesulfonamido)-4-mercaptopyrrolidine. By the procedure described above for the synthesis of (±)-N-Boc-trans-3-(4-phenoxybenzenesulfonamido)-4-hydroxypyrrolidine, (3R,4R)—N-Boc-3-azido-4-hydroxypyrrolidine was converted to (3R,4R)—N-Boc-3-(4-phenoxybenzene-sulfonamido)-4-hydroxypyrrolidine: $^1$H NMR (300 MHz, CDCl$_3$) identical to that of the (±)-N-Boc-trans-3-(4-phenoxybenzenesulfonamido)-4-hydroxypyrrolidine; $[α]_{20}^D$=−23.5° (c=0.74, CHCl$_3$).

(3R,4R)—N-Boc-3-(4-Phenoxybenzenesulfonamido)-4-hydroxy-pyrrolidine (100 mg, 0.23 mmol) was dissolved in trifluoroacetic acid (1 mL) and was stirred until no starting material was detected on TLC (50% ethyl acetate in hexane). The reaction mixture was evaporated under reduced pressure and the residue was dissolved in CH$_2$Cl$_2$ (2 mL). The solution was cooled to 0° C. and triethylamine (71 µL, 0.84 mmol) and Cbz-Cl (41 mg, 0.24 mmol) were added, and the mixture was stirred for 2 hr at room temperature. The solution was washed with water, dried over Na$_2$SO$_4$ and evaporated. The residue was purified by flash chromatography (25% ethyl acetate in hexane) to give (3R,4R)—N-Cbz-3-(4-phenoxybenzenesulfonamido)-4-hydroxypyrrolidine (100 mg, 93%): $^1$H NMR (300 MHz, CDCl$_3$) δ 7.80 (d, J=9, 2H), 7.42 (t, J=8, 2H), 7.34 (m, 5H), 7.24 (t, J=7, 1H), 7.08 (m, 4H), 5.10 (s, 2H), 4.85 & 4.76 (br s, 1H), 4.34 & 4.26 (br m, 1H), 3.72 (m, 2H), 3.55 (br m, 1H), 3.32 & 3.19 (m, 2H), 2.65 & 2.53 (br s, 1H); $[°]_{20}^D$=−29.5° (c=0.8, CHCl$_3$).

To a stirred solution of PPh$_3$ (92 mg, 0.35 mmol) in THF (2 mL) at 0° C. was added DEAD (55 µL, 0.35 mmol) dropwise. After 10 min, a solution of (3R,4R)—N-Cbz-3-(4-phenoxybenzenesulfonamido)-4-hydroxypyrrolidine (82 mg, 0.175 mmol) and thiolbenzoic acid (85 µL, 0.53 mmol) in THF (2 mL) was added. The reaction mixture was stirred at room temperature overnight, then it was concentrated under reduced pressure. The residue was purified by flash chromatography (15% ethyl acetate in hexane) to give (3R,4S)—N-Cbz-3-(4-phenoxybenzenesulfonamido)-4-benzoylthio-pyrrolidine (100 mg, 97%): $^1$H NMR (300 MHz, CD$_3$OD) δ 7.89 (d, J=8, 2H), 7.80 (dd, J=9, 3, 2H), 7.66 (t, J=8, 2H), 7.51 (m, 2H), 7.35 (m, 6H), 7.20 (t, J=8, 1H), 6.93 (m, 4H), 5.11 (s, 2H), 4.21 (m, 3H), 3.87 (m, 1H), 3.61 (m, 1H), 3.46 (m, 1H); $[α]_{20}^D$=+35.7° (c=0.70, CHCl$_3$).

To a stirred solution of (3R,4S)—N-Cbz-3-(4-phenoxy-benzenesulfonamido)-4-benzoylthiopyrrolidine (60 mg, 0.102 mmol) in MeOH (1 mL) under nitrogen was added 40% aq MeNH$_2$ (100 µL, 1.16 mmol) and the mixture was stirred for 10 min. The solution was concentrated under vacuum and the residue was purified by flash column (50% ethyl acetate in hexane) to give the inhibitor (49 mg, 97%) (YHJ-7-256): $^1$H NMR (300 MHz, CD$_3$OD) δ 7.84 (m, 2H), 7.41 (m, 2H), 7.33 (m, 4H), 7.22 (t, J=8, 1H), 7.06 (m, 4H), 5.09 (s, 2H), 3.52-3.77 (m 4H), 3.39 (m, 1H), 3.18 (m, 1H); $[\alpha]_{20}^D$=−38.0 (c=0.50, MeOH); HRMS (ESI) calculated for C$_{24}$H$_{24}$N$_2$O$_5$S$_2$Na$^+$ 507.1017. found 507.1014.

Example 14

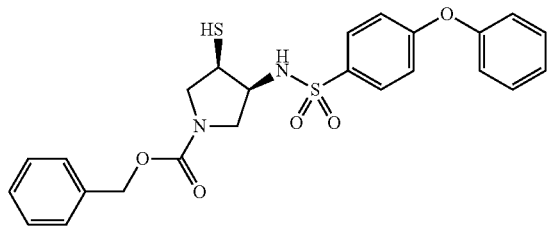

YHJ-7-257 (3S,4R)

YHJ-7-257: (3S,4R)—N-Cbz-3-(4-Phenoxybenzenesulfonamido)-4-mercaptopyrrolidine. By the procedures of Example 13, (3S,4S)—N-Boc-3-azido-4-hydroxypyrrolidine was converted to the title inhibitor (YHJ-7-257): $^1$H NMR (300 MHz, CDCl$_3$) identical to that of YHJ-256 (Example 13); $[\alpha]_{20}^D$=+38.5° (c=0.52, MeOH); HRMS (ESI) calculated for C$_{24}$H$_{24}$N$_2$O$_5$S$_2$Na$^+$ 507.1017. found 507.1020.

Example 15

The following protocol was used to obtain the data found in the following table. Materials: The fluorescent peptide substrates for matrix metalloproteinases (MMPs) used were purchased from Bachem Chem. Co. The metal salts and Brij-35 were purchased from Fisher Scientific Inc. All other chemicals were purchased from Sigma-Aldrich Chem. Co. The sources and biochemical characterizations of multiple MMPs, including MMP-1/human fibroblast collagenase (HFC), MMP-2/human fibroblast gelatinase (HFG), MMP-8/human neutrophil collagenase (HNC), and MMP-9/human neutrophil gelatinase (HNG), MMP-7/human matrilysin (MLN), MMP-3/human fibroblast stromelysin-1 (HFS), human recombinant catalytic domain of membrane-type 1 matrix metalloproteinase (cdMT1-MMP), catalytic domain of MMP-12/metalloelastase (cdMET), and MMP-26/human endometase (EDM) were described previously (Sang, Q. X., Birkedal-Hansen, H., and Van Wart, H. E. Proteolytic and non-proteolytic activation of human neutrophil progelatinase B. Biochim. Biophys. Acta. 1995; 1251, 99-108; Sang, Q. A., Bodden, M. K., and Windsor, L. J. Activation of human progelatinase A by collagenase and matrilysin: activation of procollagenase by matrilysin. J. Protein. Chem. 1996; 15, 243-253; Li, H., Bauzon, D. E., Xu, X., Tschesche, H., Cao, J., and Sang, Q.-X. A. Immunological characterization of cell-surface and soluble forms of membrane type 1 matrix metalloproteinase in human breast cancer cells and in fibroblasts. Molec. Carcinog. 1998; 22, 84-94; Park, H. I., Ni, J., Gerkema, F. E., Liu, D., Belozerov, V. E., and Sang, Q.-X. A. Identification and characterization of human endometase (Matrix metalloproteinase-26) from endometrial tumor. J. Biol. Chem., 2000; 275, 20540-20544). The active concentrations of MMPs were determined by titration with GM6001, a tight-binding MMP inhibitor, as described previously (Park, H. I., Turk, B. E., Gerkema, F. E., Cantley, L. C., and Sang, Q.-X. A. Peptide substrate specificities and protein cleavage sites of human endometase/matrilysin-2/matrix metalloproteinase-26. J. Biol. Chem. 2002; 277, 35168-35175).

Determination of Mercaptosulfonamide Inhibitor Concentration.

The active inhibitor concentrations were estimated by titrating the mercapto group with 5,5'-dithiobis(2-nitrobenzoic acid) (DTNB; Ellman's reagent) as described previously (Ellman, G. L. A colorimetric method for determining low concentrations of mercaptans. Arch. Biochem. Biophys. 1958; 74, 443-450; Ellman, G. L. Tissue sulfhydryl groups. Arch. Biochem. Biophys. 1959; 82, 70-77; Riddles, P. W., Blakeley, R. L., and Zerner, B. Ellman's reagent: 5,5'-dithiobis(2-nitrobenzoic acid)—a reexamination. Anal. Biochem. 1979; 94, 75-81). Briefly, the reaction of DTNB with the mercapto group produces 2-nitro-5-thiobenzoic acid (TNB). The concentration of TNB is then measured by monitoring the absorbance at 412 nm. Cysteine was used to generate the standard curve with a molar extinction coefficient of 14,000±500 M$^{-1}$ cm$^{-1}$, which is close to the value in the literature (Riddles, P. W., Blakeley, R. L., and Zerner, B. Ellman's reagent: 5,5'-dithiobis(2-nitrobenzoic acid)—a reexamination. Anal. Biochem. 1979; 94, 75-81).

Enzyme Kinetic Assays and Inhibition of MMPs.

The substrate Mca-PLGLDpaAR-NH$_2$ was used to measure inhibition constants (Knight, C. G., Willenbrock. F., and Murphy, G. A novel coumarin-labelled peptide for sensitive continuous assays of the matrix metalloproteinases. FEBS Lett. 1992; 296, 263-266). Enzymatic assays were performed at 25° C. in 50 mM HEPES buffer at pH 7.5 in the presence of 10 mM CaCl$_2$, 0.2 M NaCl, and 0.01% or 0.05% Brij-35 with substrate concentrations of 1 μM. The release of product was monitored by measuring fluorescence (excitation and emission wavelengths of 328 nm and 393 nm, respectively) with a Perkin Elmer Luminescence Spectrophotometer LS 50B connected to a temperature controlled water bath. All stock solutions of inhibitors were in dimethyl sulfoxide. For inhibition assays, 10 μl of inhibitor stock solution, 176 μl of assay buffer, and 10 μl of enzyme stock solution were mixed and incubated for 30 to 60 minutes prior to initiation of the assay, which was accomplished by adding and mixing 4 μl of the substrate stock solution. Enzyme concentrations ranged from 0.2 to 7 nM during the assay. Apparent inhibition constant ($K_i^{app}$) values were calculated by fitting the kinetic data to the Morrison equation for tight-binding inhibitors (Morrison, J. F. Kinetics of the reversible inhibition of enzyme-catalysed reactions by tight-binding inhibitors. Biochim. et Biophys. Acta 1969; 185, 269-286.), where $v_i$ and $v_o$ are the initial rates with and without inhibitor respectively, and $[E]_o$ and $[I]_o$ are the initial (total) enzyme and inhibitor concentrations, respectively. More detailed experimental design and methods have been described in previous publications (Park, H. I., Jin, Y., Hurst, D. R., Monroe, C. A., Lee, S., Schwartz, M. A. and Sang, Q.-X. The intermediate S1 pocket of the endometase/matrilysin-2 active site revealed by enzyme inhibition kinetic studies, protein sequence analyses, and homology modeling. J. Biol. Chem. 2003. 278, 51646-51653. Hurst, D. R., Schwartz, M. A., Jin, Y., Ghaffari, M. A. Kozarekar, P., Cao, J., Sang, Q.-X. Inhibition of enzyme activity and cell-mediated substrate cleavage of membrane type 1-matrix metalloproteinase by newly developed mercaptosulfide inhibitors. Biochem. J. 2005. 392, 527-536.)

Inhibition of Selected MMPs

| | \multicolumn{9}{c}{IC$_{50}$ (K$_i$), nM} | | | | | | | | |
|---|---|---|---|---|---|---|---|---|---|
| Inhibitor | cdMT-1 MMP-14 | EDM MMP-26 | cdMET MMP-12 | HFC MMP-1 | HNG MMP-9 | HFG MMP-2 | HFS MMP-3 | MLN MMP-7 | COL-3 MMP-13 |
| Example 1. YHJ-6-286 | (11) | (32) | (250) | (4100) | (15) | (3.9) | (460) | >25000 | (50) |
| Example 2. YHJ-6-290 | (21) | (41) | (2) | (2800) | (2.4) | (35) | (37) | >12500 | (27) |
| Example 3. YHJ-6-293 | (110) | (28) | (38) | ~25000 | (230) | (27) | (2500) | >25000 | (35) |
| Example 4. YHJ-7-23 | (62) | (19) | (160) | (850) | (1.3) | (2.3) | (350) | >25000 | (28) |
| Example 5. YHJ-6-90 | (100) | (72) | (720) | >12500 | (13) | (24) | (4500) | >50000 | (450) |
| Example 6. YHJ-6-93 | (3100) | (650) | (710) | >130000 | (81) | (78) | ~7000 | >12500 | (100) |
| Example 7. YHJ-7-52 | (5) | (4) | (4.8) | >3000 | (2.3) | (2.2) | (2000) | (4000) | (2) |
| Example 8. YHJ-7-56 | (4) | (3) | (2) | >6000 | (1.5) | (3.8) | (810) | (3000) | (1.7) |
| Example 9. YHJ-7-75 | (70) | (270) | (29) | >6000 | (400) | (63) | ~20000 | (2000) | (47) |
| Example 10. YHJ-7-288 | | | | 50000 | (210) | (38) | (5900) | | |
| Example 11. YHJ-7-283 | | | | 6300 | (230) | (49) | (1600) | | |
| Example 12. YHJ-7-291 | | | | | (13) | (10) | (1700) | | |
| Example 13. YHJ-7-256 | | | | ~125000 | (3100) | (1800) | (5400) | | |
| Example 14. YHJ-7-257 | | | | >3000 | (2200) | (800) | (3400) | | |

Example 16

Matrix Metalloproteinase Inhibitor (MMPI) Biological Data

Matrix Metalloproteinase Inhibitor (MMPI) Stability and Cytotoxicity in Human Coronary Artery Smooth Muscle Cells (hCASMC) and Human Mesenchymal Stem Cells (hMSC)

MMPI Stability

Assays were carried out in 50 mM HEPES buffer (pH 7.5) containing 10 mM CaCl$_2$, 0.2 M NaCl, and 0.01% Brij-35 at 25° C. In addition, 5 µM of the reducing agent tris(2-carboxyethyl)-phosphine (TCEP) hydrochloride was included in the assay medium. The enzyme (MMP-9, final concentration 1 nM) was incubated with each MMPI for 30 min before starting the assay by adding the substrate (Mca-PLGLDpaAR-NH$_2$) solution in 1:1 DMSO:H$_2$O (the assays thus contained 6% (v/v) DMSO). Furthermore, MMPI concentrations were obtained by dilution with DMSO and made close to their reported IC$_{50}$ values from previous observations. Before testing, all MMPIs were incubated in HEPES buffer at varies time points from 0 to 24 hours to ascertain their stability at various time points.

Mercaptosulfonamide inhibitors YHJ-7-23, YHJ-6-286, YHJ-6-90, and YHJ-6-293 were used for biological studies. YHJ-7-23 has the formula C$_{18}$H$_{21}$N$_3$O$_4$S$_2$ and has a molecular mass of 407.51. YHJ-6-286 has the formula C$_{17}$H$_{19}$N$_3$O$_4$S$_2$ and a molecular mass of 393.48. YHJ-6-90 has the formula C$_{25}$H$_{26}$N$_2$O$_5$S$_2$ and a molecular mass of 498.62. YHJ-6-293 has the formula C$_{16}$H$_{19}$ClN$_2$O$_3$S$_2$ and a molecular mass of 386.92.

MMPI Stability Data

FIG. 1 shows the stability of three heterocyclic mercaptosulfonamide MMPIs incubated with human MMP-9 in HEPES buffer at various time points. Each are relatively stable in this buffer as there is only about a 10 to 20% loss of inhibition of MMP-9 activity after 8 hours of incubation.

Human Coronary Artery Smooth Muscle Cell (hCASMC) Growth

Passage 7 human coronary artery smooth muscle cells (hCASMCs) were plated in a 10 cm dish containing 20 mL of smooth muscle basal medium (SmBm, Lonza, Cat. No. CC-3182) supplemented with 0.1% insulin, 0.1% epidermal growth factor (rhEGF), 0.2% fibroblast growth factor-B (rhFGF-B), 0.1% gentamicin/amphotericin (antibiotics), and 5% FBS. The cells were incubated for 24 hours at 37° C. and 5% CO$_2$, with 20 mL of fresh SmBm added the following day. Fresh SmBm was added every 2 days until the culture was ~70-80% confluent and contained a minimum of 5 mitotic figures when viewed at 100× magnification. At this time, cells were then trypsinized and seeded into 24-well plates at an initial density of 3,500 cells/cm$^2$ and grown to ~60% confluence prior to MMPI treatment.

Human Mesenchymal Stem Cell (hMSC) Growth

Passage 3 human adult bone marrow-derived mesenchymal stem cells (hMSCs, Tulane Center for Gene Therapy) were plated for a recovery phase of 24 hours at 37° C. and 5% CO$_2$ in Alpha Minimum Essential Medium (αMEM, Sigma Aldrich) containing L-glutamine but without ribonucleosides or deoxyribonucleosides, 16.5% FBS, ~2-4 mM L-glutamine, and penicillin and streptomycin as antibiotics. After the recovery phase, hMSCs were seeded into 6-well plates at a density of ~60 cells/cm$^2$ within each well containing 2 mL of cell culture medium. Fresh cell culture medium was added every 3 days until the cells reached a confluency of approximately ~70% at which media was changed to the conditioned forms necessary for observing MMPI cytotoxicity.

MMPI Treatment

Upon reaching the desired confluency, each cell type was treated with the respective fresh media that was conditioned with a logarithmic panel of MMPI concentrations ranging from 1 nM to 100 µM. Specifically, each of the inhibitors were dissolved in an appropriate amount of 100% EtOH to generate 8 mM stock solutions from which an aliquot was used to produce serial dilutions with either SmBm or αMEM. The conditioned media was added to either hCASMCs or hMSCs and incubated for 24 hours. At the end of the treatment period, the media was removed and the cells were trypsinized after being washed 3× with PBS. In order to quantify the levels of toxicity these inhibitors had on hCASMC and hMSC growth and viability, the cells were treated with trypan blue and counted via a hemocytometer. Each of the treatments, and hemocytometer counts, were performed in triplicate and all error bars represent 95% confidence intervals.

Human Coronary Artery Smooth Muscle Cell (hCASMC) Data

Figure 2:
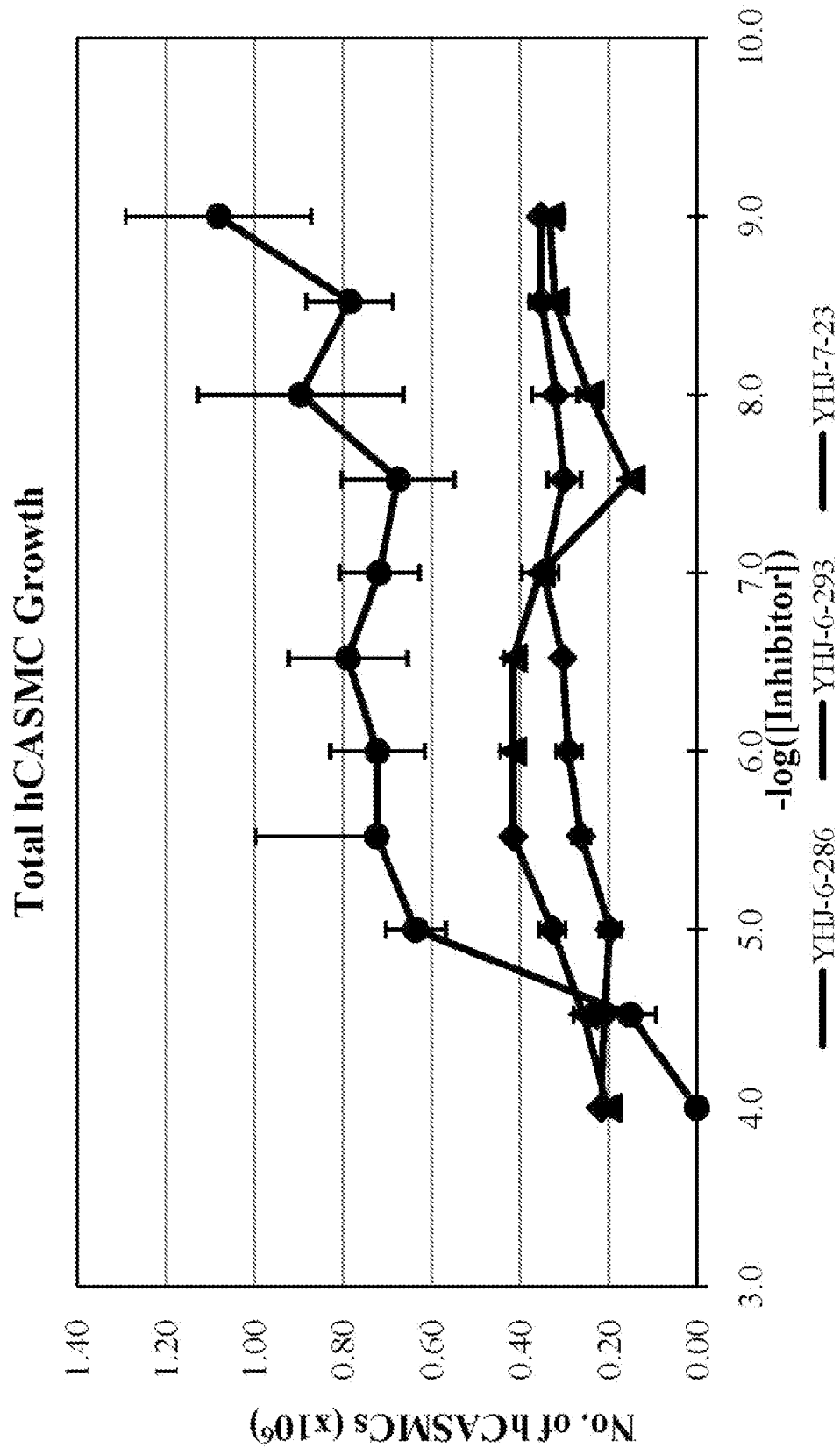
FIG. 2 is a graph showing the total hCASMC growth in the presence of three MMPIs (YHJ-6-286, YHJ-6-293, and YHJ-7-23). MMPI concentration is paneled logarithmically from a concentration of 100 µM to 1 nM, as further described in Example 16.

FIG. 2 shows the hCASMC growth in the presence of three MMPIs (YHJ-6-286, YHJ-6-293, and YHJ-7-23). MMPI concentration was paneled logarithmically from a concentration of 100 µM to 1 nM. Cells were ~60% confluent upon MMPI treatment, which lasted 24 hours. Error bars indicate standard error in the mean with 95% confidence.

Figure 3:
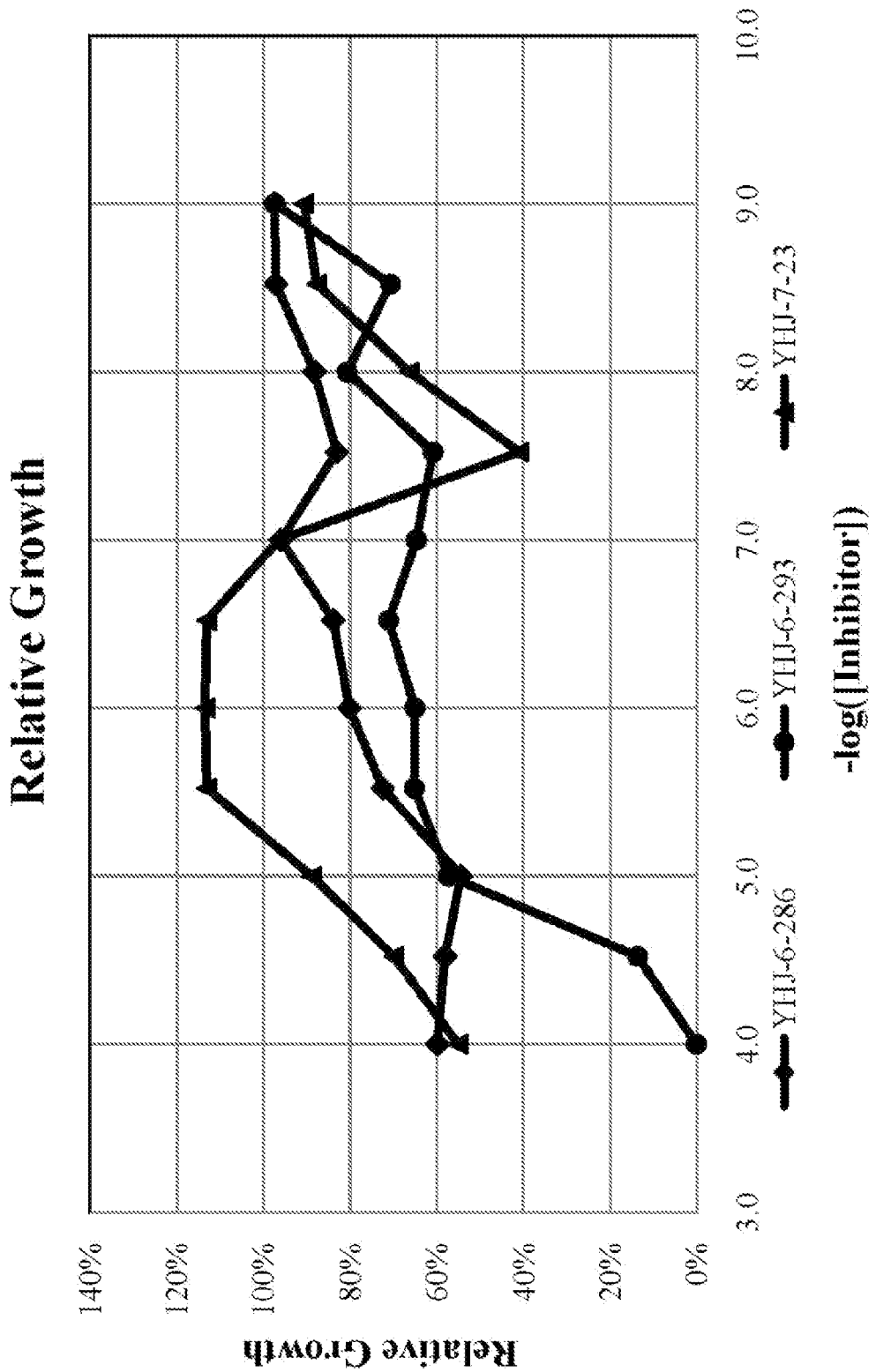
FIG. 3 is a graph showing the total hCASMC growth in the presence of three MMPIs (YHJ-6-286, YHJ-6-293, and YHJ-7-23), defining relative growth as the number of hCASMCs counted under different MMPI concentrations and normalized by the number of hCASMCs observed when no MMPI was present, as further described in Example 16.

FIG. 3 reveals the same data presented in the previous figure with the exception that relative growth (%) was defined as the number of hCASMCs counted under different MMPI concentrations and normalized by the number of hCASMCs observed when no MMPI was present.

Human Mesenchymal Stem Cell (hMSC) Data

Figure 4:
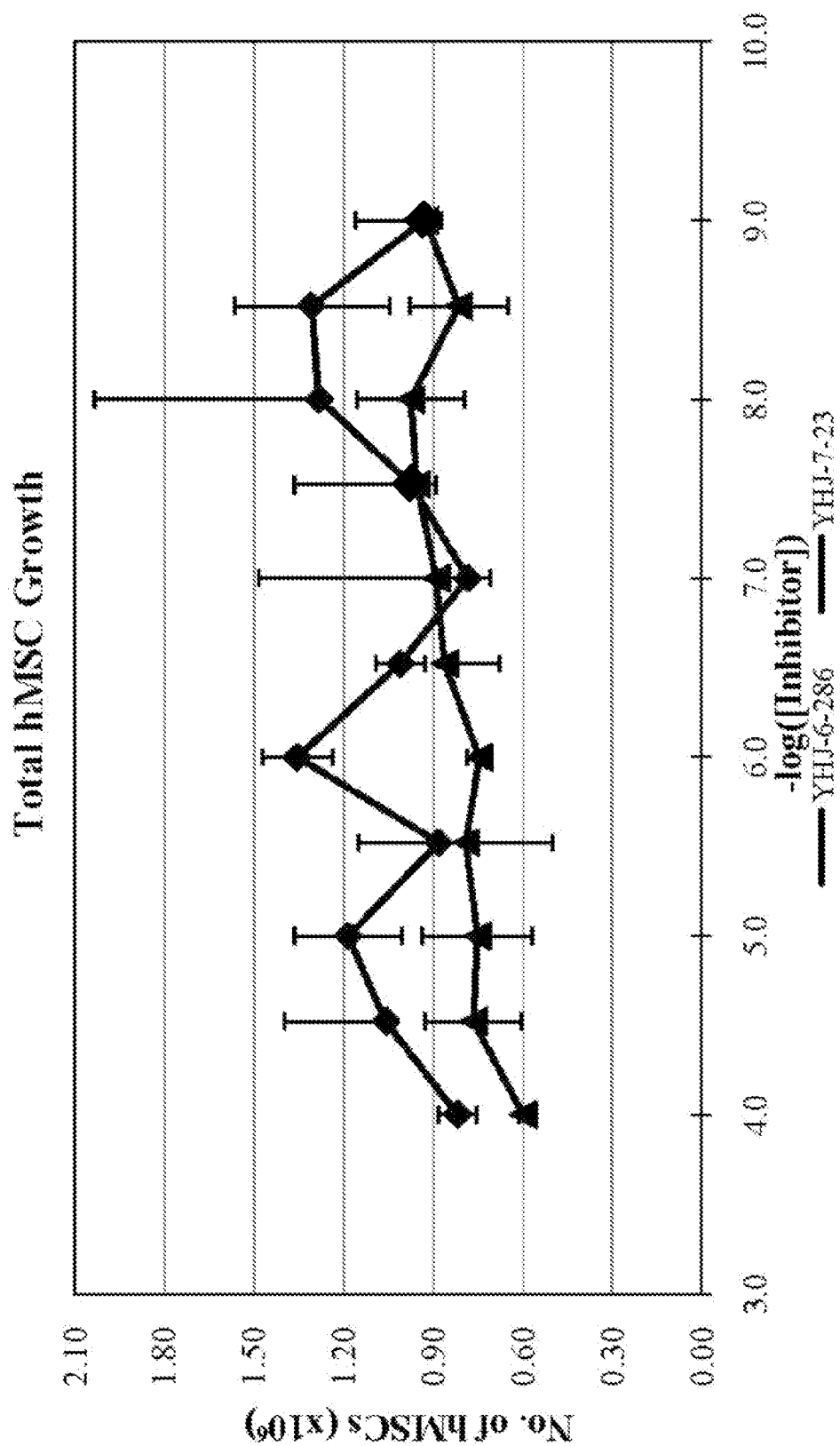
FIG. 4 is a graph showing the total hMSC growth in the presence of two MMPIs (YHJ-6-286 and YHJ-7-23). MMPI concentration was paneled logarithmically from 100 µM to 1 nM, as further described in Example 16.

FIG. 4 shows the total hMSC growth in the presence of two MMPIs (YHJ-6-286 and YHJ-7-23). MMPI concentration was paneled logarithmically from 100 µM to 1 nM. hMSCs were ~70% confluent upon treatment which lasted 24 hours. Error bars indicate standard error in the mean with 95% confidence.

Figure 5:
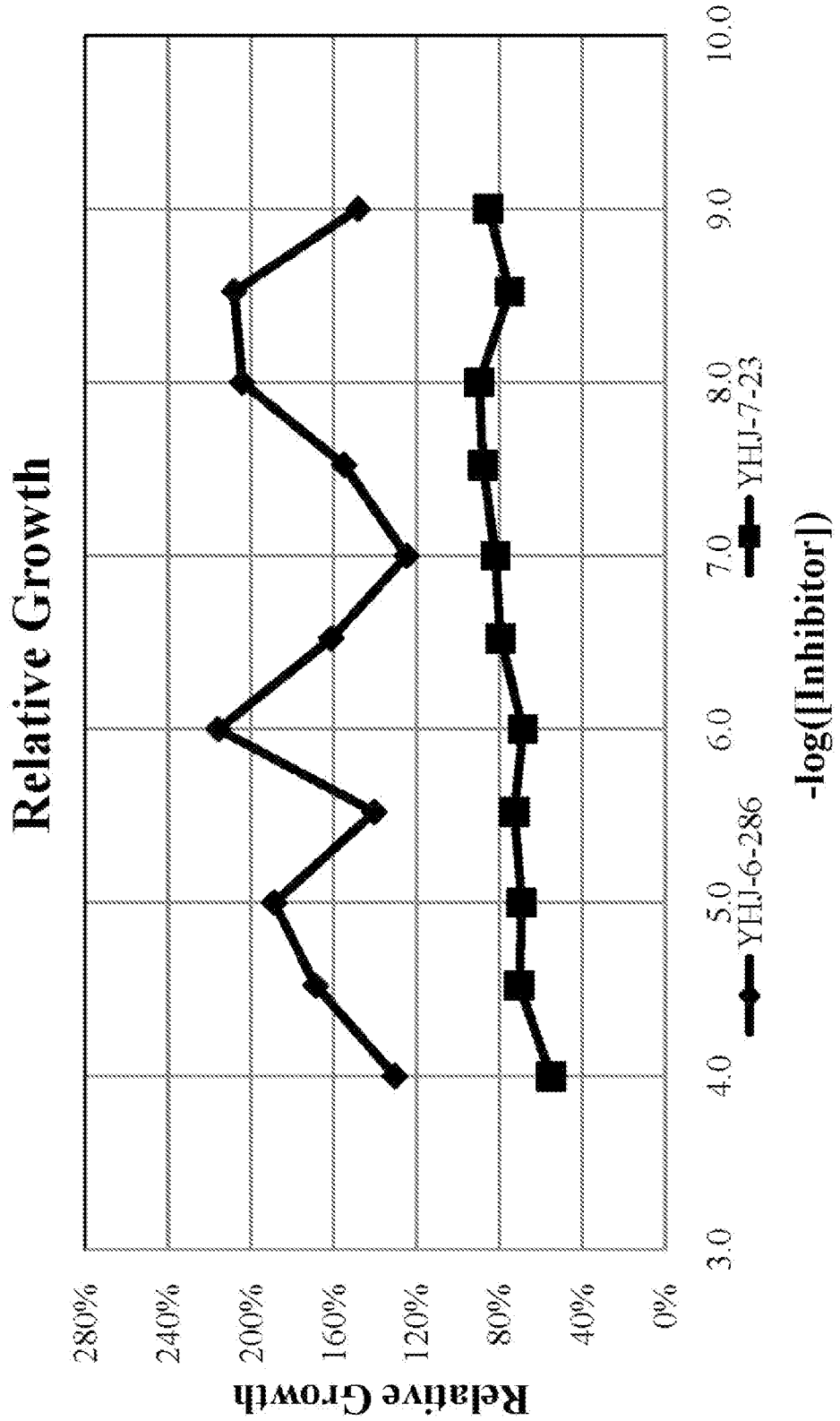
FIG. 5 is a graph showing the total hMSC growth in the presence of two MMPIs (YHJ-6-286 and YHJ-7-23), defining relative growth as the number of hMSCs counted under different MMPI concentrations and normalized by the number of hMSCs observed when no MMPI was present, as further described in Example 16.

FIG. 5 reveals the same data presented in the previous figure with the exception that relative growth (%) was defined as the number of hMSCs counted under different MMPI concentrations and normalized by the number of hMSCs observed when no MMPI was present.

Discussion

The initial selection of promising inhibitors ($K_i$ <50 nM) included three compounds (YHJ-6-286, YHJ-6-293, and YHJ-7-23) targeting MMPs expressed in hCASMCs, hMSCs, or both cell lines. As indicated by the preceding figures, higher dosages of inhibitor affected hCASMCs and hMSCs similarly as viability was minimal from an inhibitor concentration range of 100 µM to ~30 µM. Interestingly, lower concentrations of YHJ-6-293, which targets MMP-2, -12, and -13, increased hCASMC growth nearly two-fold when compared to identical concentrations of YHJ-6-286 and YHJ-7-23, which only differ in their abilities to selectively target MMP-9 and MT1-MMP. Unique to only the hCASMC growth curves, treatment with YHJ-7-23 consistently resulted in a local minimum originating at 300 nM and minimizing at ~30 nM before reversing the trend and slowly increasing once more. In terms of hMSCs, the growth curve steadily increased as the concentration of YHJ-7-23 was decreased, while YHJ-6-286 produced erratic results. Overall on the basis of these results, future experiments inhibiting MMP function in these cell lines will begin with inhibitor concentrations of 10 µM, as concentrations higher than this exhibited a much greater toxicity towards both cell lines and produced erratic trends.

Example 17

Inhibition of Human Brain Microvascular Endothelial Cell Migration and Wound Healing Culture of human brain microvascular endothelial cells: Human brain microvascular endothelial cells (hBMECs) were cultured with EGM-2MV Microvascular Endothelial Cell Medium-2 1 kit Bullet Kit, 5% fetal bovine serum, with or without treatments with synthetic matrix metalloproteinase inhibitors (MMPIs), at 37° C. and 5% $CO_2$.

Endothelial cell migration and wound-healing assays: All experiments for this phase were performed in triplicate, and each consisted of seven wounded cultures utilizing serial concentrations of MMPIs: (1) an untreated control; (2) 100 µM MMPI; (3) 30 µM MMPI; (4) 10 µM MMPI; (5) 3 µM MMPI; (6) 1 µM MMPI; (7) 100 nM MMPI; (8) 10 nM MMPI; and (9) 1 nM MMPI. A 1 mL pipette tip was utilized to create a linear wound in a confluent monolayer of hBMECs. A fine, sterile needle was used to demarcate a cell-free "wounded field". All cultures were photographed at that time. After 24 hours, the wounded cell culture was washed three times with phosphate buffered saline, fixed with 4% paraformaldehyde for 10-20 min, and stained with 0.1% crystal violet for 10-20 min. The stained culture was washed with $ddH_2O$ three times and left overnight to air dry. Stained cultures were photographed under Nikon microscope at 5× objective. The density of the cell coverage in the wounded field was quantified utilizing the integrated morphometry analysis (IMA) (Metamorph System v.4.6r8, University Imaging Corp.). Analysis of Variants or other statistical methods were used for subsequent comparative statistical analyses. The contribution of gelatinases to the migration of hBMECs was concluded based on results.

Figure 6:
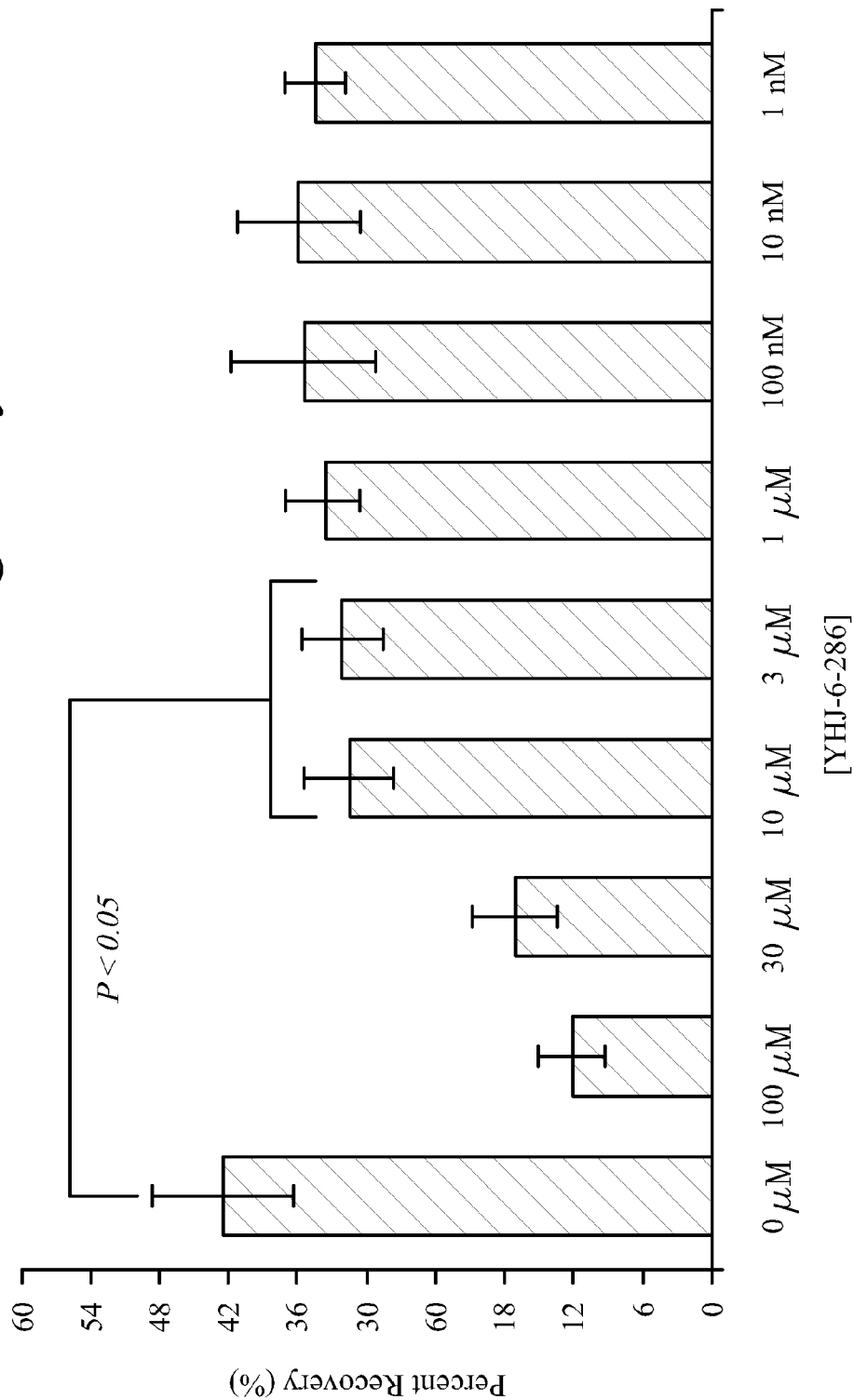
FIG. 6 is a bar graph showing the wound healing assay of YHJ-6-286 on hBMECs, plotting the concentration of YHJ-6-286 and the percent recovery of a wonded confluent monolayer of hBMECs, as further described in Example 17.

FIG. 6 shows the wound healing assay of YHJ-6-286 on hBMECs. This inhibitor has shown pretty good inhibition on hBMEC wound healing at 3 µM and above. Comparing with the control, at 10 µM, the wound healing process was slowed down by showing a decrease of approximately 25% cell recovery rate.

Figure 7:
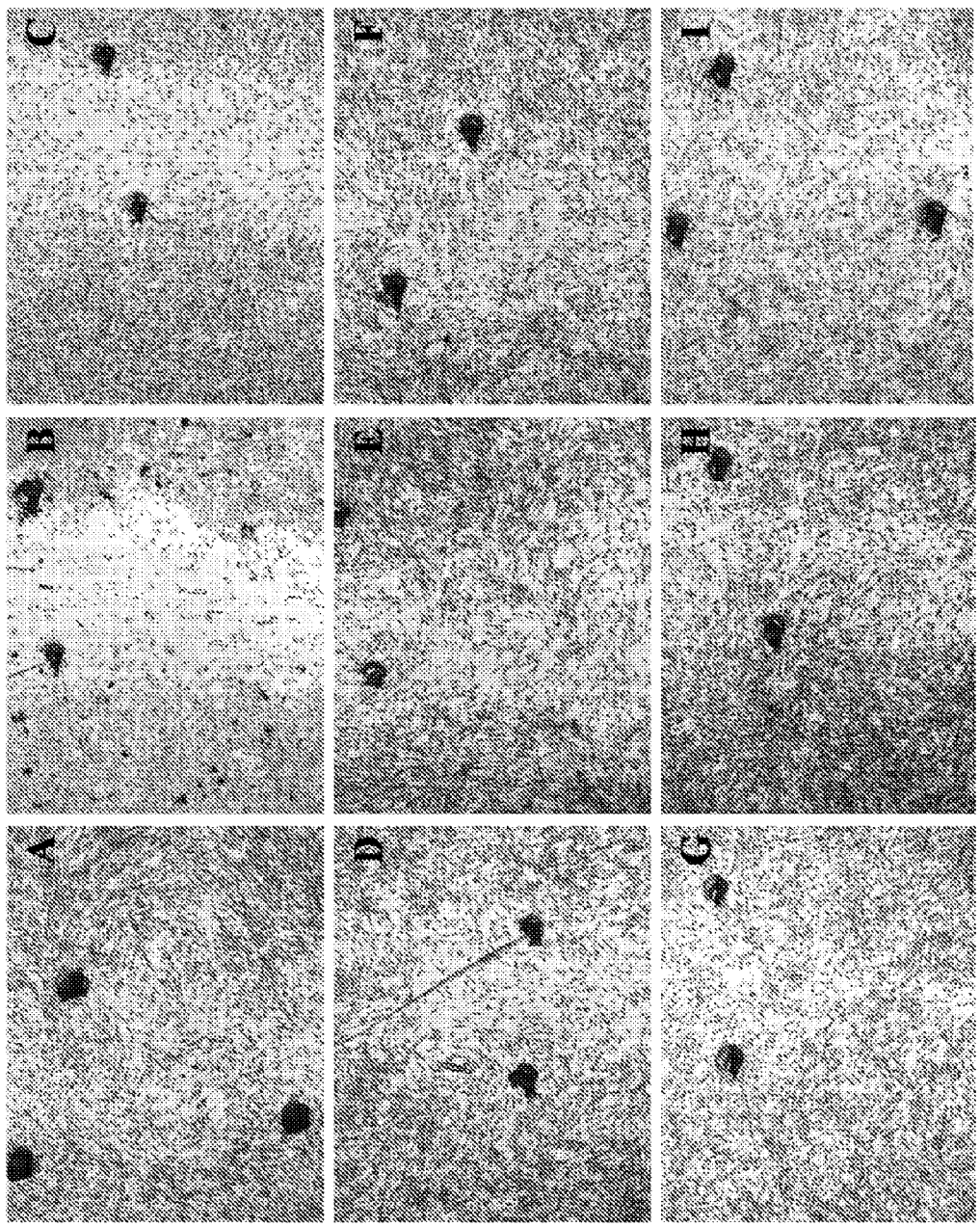
FIG. 7 shows photographs of representative images of wounded human brain microvascular endothelial cells treated with various concentrations of MMPI YHJ-6-286, as further described in Example 17.

FIG. 7 shows representative images (50× Magnification) of wounded human brain microvascular endothelial cells treated with various concentrations of MMPI YHJ-6-286. The concentrations of the MMPI used are: Panel A =0.00 µM; Panel B=100 µM; Panel C=30 µM; Panel D=10 µM; Panel E=3 µM; Panel F=1 µM; Panel G=100 nM; Panel H=10 nM; and Panel I=1 nM.

What is claimed is:

1. A substituted heterocyclic mercaptosulfonamide corresponding to the formula:

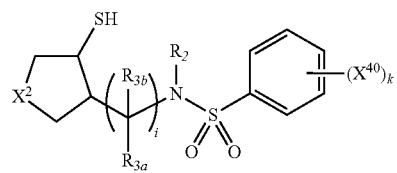

wherein
A⁻ is a counteranion;
i is 0 or 1;
k is an integer from 1 to 5, inclusive;
$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$X^2$ is —N($X^{20}$)— or —N$^+$($X^{26}$)($X^{27}$)—A$^-$;

$X^{20}$ is hydrogen or acyl, $X^{26}$ and $X^{27}$ are independently hydrogen, hydrocarbyl, substituted hydrocarbyl, or, in combination with the nitrogen atom to which they are attached, form a heterocyclo ring; and each $X^{40}$ is independently hydrocarbyl, substituted hydrocarbyl, halo, amino, nitro, hydroxyl, alkoxy, acyl, or heterocyclo;

wherein a substituted hydrocarbyl is a hydrocarbyl group substituted with at least one of a halogen, heterocyclo, alkoxy, alkenoxy, alkynoxy, aryloxy, hydroxy, keto, acyl, acyloxy, nitro, amino, amido, cyano, thiol, ketal, acetal, ester and ether.

2. The substituted heterocyclic mercaptosulfonamide of claim 1 wherein $X^2$ is —N$^+$($X^{26}$)($X^{27}$)—A$^-$.

3. The substituted heterocyclic mercaptosulfonamide of claim 2 wherein $X^{26}$ and $X^{27}$ are hydrogen.

4. The substituted heterocyclic mercaptosulfonamide of claim 3 wherein i is 0.

5. The substituted heterocyclic mercaptosulfonamide of claim 1 wherein i is 0.

6. The substituted heterocyclic mercaptosulfonamide of claim 1 wherein the substituted heterocyclic mercaptosulfonamide corresponds to Formula 5:

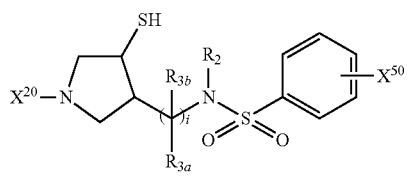

Formula 5 wherein i is 0 or 1;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$X^{20}$ is hydrogen or acyl,; and $X^{50}$ is hydrocarbyl, substituted hydrocarbyl, halo, amino, nitro, hydroxy, alkoxy, acyl, or heterocyclo.

7. The substituted heterocyclic mercaptosulfonamide of claim 6 wherein $R_2$ is hydrogen or alkyl.

8. The substituted heterocyclic mercaptosulfonamide of claim 6 wherein $X^{20}$ is hydrogen.

9. The substituted heterocyclic mercaptosulfonamide of claim 6 wherein i is 0.

10. The substituted heterocyclic mercaptosulfonamide of claim 6 wherein $X^{20}$ is $X^{200}$C(O)—, $X^{200}$ is alkyl, substituted alkyl, $R^1R^2N$—, or $R^1O$—, $R^1$ is hydrogen, hydrocarbyl, substituted hydrocarbyl, or heterocyclo, and $R^2$ is hydrogen, hydrocarbyl, substituted hydrocarbyl or heterocyclo.

11. The substituted heterocyclic mercaptosulfonamide of claim 10 wherein $R_2$ is hydrogen or alkyl.

12. The substituted heterocyclic mercaptosulfonamide of claim 10 wherein i is 0.

13. The substituted heterocyclic mercaptosulfonamide of claim 10 wherein $R_2$ is hydrogen or alkyl and i is 0.

14. The substituted heterocyclic mercaptosulfonamide of claim 6 wherein $X^{20}$ is $X^{200}$C(O)—, and $X^{200}$ is heterocyclo.

15. The substituted heterocyclic mercaptosulfonamide of claim 14 wherein $R_2$ is hydrogen or alkyl and i is 0.

16. The substituted heterocyclic mercaptosulfonamide of claim 6 wherein $X^{50}$ is hydrocarbyl.

17. The substituted heterocyclic mercaptosulfonamide of claim 6 wherein $X^{50}$ is substituted hydrocarbyl.

18. The substituted heterocyclic mercaptosulfonamide of claim 1 wherein the substituted heterocyclic mercaptosulfonamide corresponds to Formula 6:

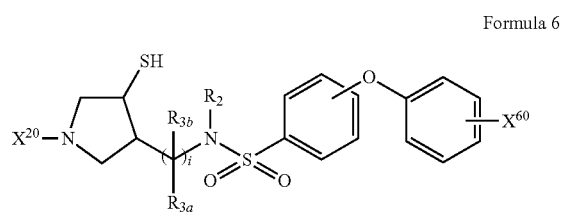

Formula 6 wherein i is 0 or 1;

$R_2$ is hydrogen, hydrocarbyl, substituted hydrocarbyl, or heterocyclo;

$R_{3a}$ and $R_{3b}$, when i is 1, are independently hydrogen, hydrocarbyl, or substituted hydrocarbyl;

$X^{20}$ is hydrogen or acyl,; and $X^{60}$ is hydrocarbyl, substituted hydrocarbyl, halo, amino, nitro, hydroxy, alkoxy, acyl, or —C(O)$X^{61}$; and $X^{61}$ is hydroxy, amino or alkoxy.

19. The substituted heterocyclic mercaptosulfonamide of claim 18 wherein i is 0.

20. The substituted heterocyclic mercaptosulfonamide of claim 18 wherein $R_2$ is hydrogen or alkyl and i is 0.

21. The substituted heterocyclic mercaptosulfonamide of claim 18 wherein $X^{20}$ is $X^{200}$C(O)—, $X^{200}$ is alkyl, substituted alkyl, $R^1R^2N$—, or $R^1O$—, $R^1$ is hydrogen, hydrocarbyl, substituted hydrocarbyl, or heterocyclo, and $R^2$ is hydrogen, hydrocarbyl, substituted hydrocarbyl or heterocyclo.

22. The substituted heterocyclic mercaptosulfonamide of claim 21 wherein $R_2$ is hydrogen or alkyl.

23. The substituted heterocyclic mercaptosulfonamide of claim 21 wherein i is 0.

24. The substituted heterocyclic mercaptosulfonamide of claim 21 wherein $R_2$ is hydrogen or alkyl and i is 0.

25. The substituted heterocyclic mercaptosulfonamide of claim 21 wherein $X^{20}$ is $X^{200}$C(O)—, and $X^{200}$ is heterocyclo.

26. The substituted heterocyclic mercaptosulfonamide of claim 25 wherein $R_2$ is hydrogen or alkyl and i is 0.

27. A substituted heterocyclic mercaptosulfonamide selected from the group consisting of

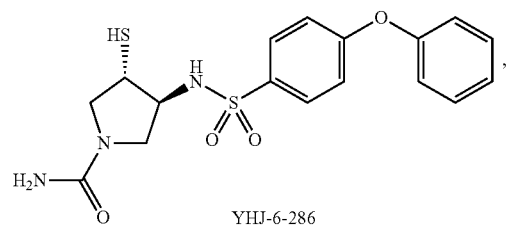

YHJ-6-286

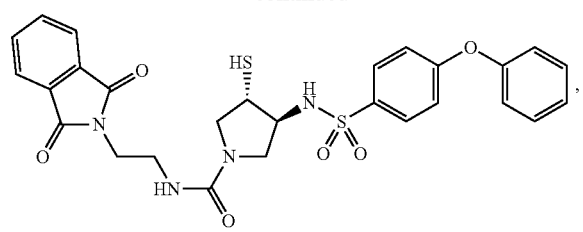
YHJ-6-290
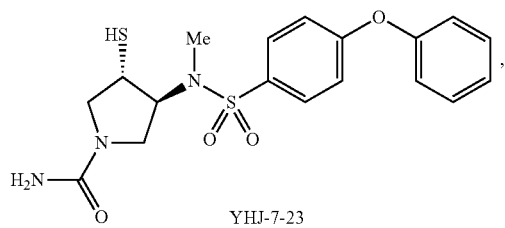
YHJ-7-23
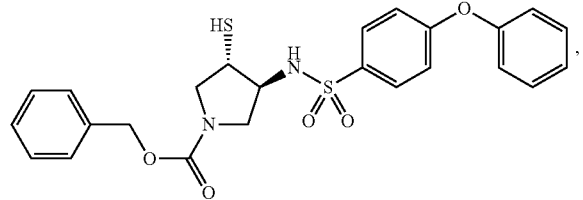
YHJ-6-90
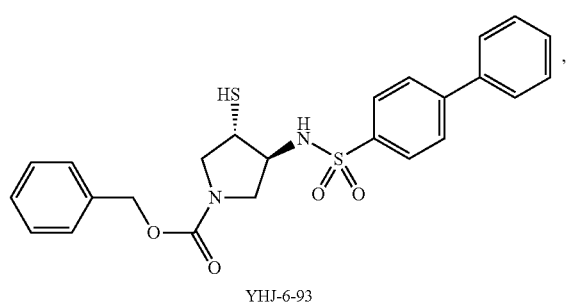
YHJ-6-93
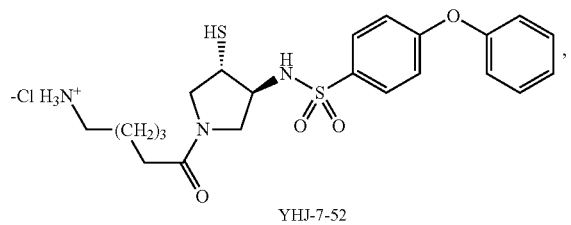
YHJ-7-52
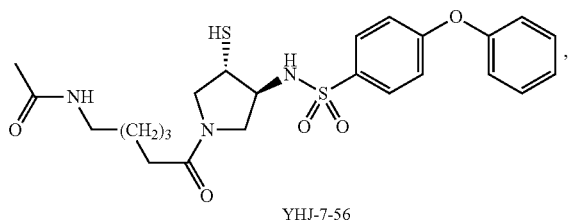
YHJ-7-56
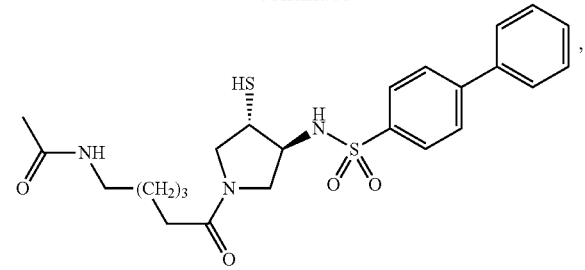
YHJ-7-75
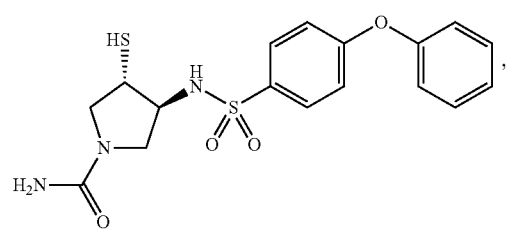
YHJ-7-291 (3S,4S)
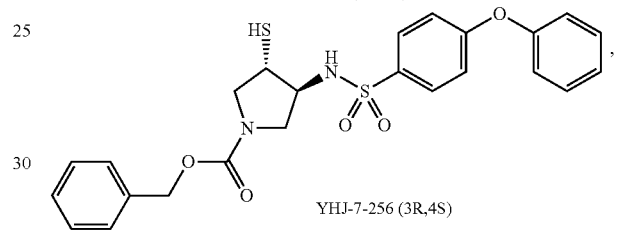
YHJ-7-256 (3R,4S)
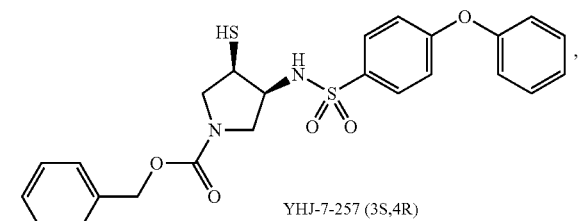
YHJ-7-257 (3S,4R)
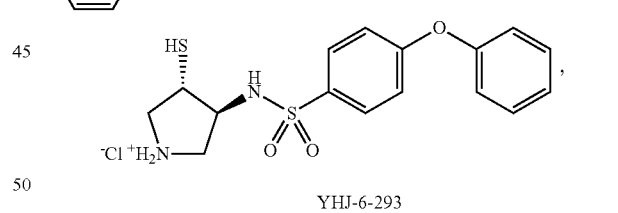
YHJ-6-293
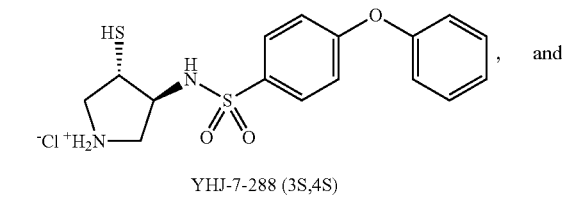
and
YHJ-7-288 (3S,4S)
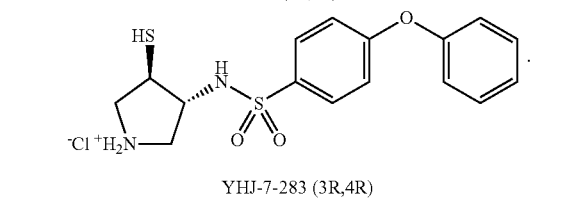
YHJ-7-283 (3R,4R)

28. A substituted heterocyclic mercaptosulfonamide corresponding to Formula YHJ-7-52:
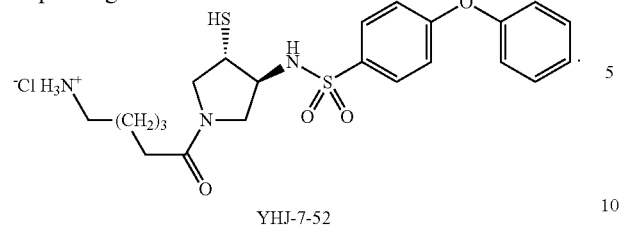
YHJ-7-52
29. A pharmaceutical composition comprising a substituted heterocyclic mercaptosulfonamide inhibitor of claim 1.
* * * * *